(12) United States Patent
Ohsawa et al.

(10) Patent No.: US 7,511,169 B2
(45) Date of Patent: *Mar. 31, 2009

(54) SULFONATE SALTS AND DERIVATIVES, PHOTOACID GENERATORS, RESIST COMPOSITIONS, AND PATTERNING PROCESS

(75) Inventors: Youichi Ohsawa, Joetsu (JP); Takeru Watanabe, Joetsu (JP); Takeshi Kinsho, Joetsu (JP); Katsuhiro Kobayashi, Joetsu (JP)

(73) Assignee: Shin-Etsu Chemical Co., Ltd., Tokyo (JP)

( * ) Notice: Subject to any disclaimer, the term of this patent is extended or adjusted under 35 U.S.C. 154(b) by 254 days.

This patent is subject to a terminal disclaimer.

(21) Appl. No.: 11/397,526

(22) Filed: Apr. 5, 2006

(65) Prior Publication Data

US 2006/0228648 A1  Oct. 12, 2006

(30) Foreign Application Priority Data

Apr. 6, 2005  (JP) ............................. 2005-109903
Oct. 31, 2005  (JP) ............................. 2005-316096

(51) Int. Cl.
  *C07C 309/06* (2006.01)
  *G03F 7/004* (2006.01)

(52) U.S. Cl. .................. 562/30; 562/111; 562/113; 430/270.1; 430/921; 430/925

(58) Field of Classification Search ............... 562/30, 562/111, 113; 430/270.1, 921, 925
See application file for complete search history.

(56) References Cited

U.S. PATENT DOCUMENTS

| | | | |
|---|---|---|---|
| 5,635,332 A | 6/1997 | Nakano et al. | |
| 5,705,702 A | 1/1998 | Osawa et al. | |
| 5,714,625 A | 2/1998 | Hada et al. | |
| 6,004,724 A | 12/1999 | Yamato et al. | |
| 6,048,672 A | 4/2000 | Cameron et al. | |
| 6,063,953 A | 5/2000 | Hada et al. | |
| 6,261,738 B1 | 7/2001 | Asakura et al. | |
| 6,280,898 B1 | 8/2001 | Hasegawa et al. | |
| 6,284,429 B1 | 9/2001 | Kinsho et al. | |
| 6,312,867 B1 | 11/2001 | Kinsho et al. | |
| 6,413,695 B1 | 7/2002 | Nishi et al. | |
| 6,440,634 B1 | 8/2002 | Ohsawa et al. | |
| 6,444,396 B1 | 9/2002 | Watanabe et al. | |
| 6,448,420 B1 | 9/2002 | Kinsho et al. | |
| 6,509,135 B2 | 1/2003 | Nishi et al. | |
| 6,517,994 B2 | 2/2003 | Watanabe | |
| 6,605,408 B2 | 8/2003 | Nishi et al. | |
| 6,673,515 B2 | 1/2004 | Nishi et al. | |
| 6,673,518 B2 | 1/2004 | Nishi et al. | |
| 6,723,483 B1 | 4/2004 | Oono et al. | |
| 6,830,866 B2 | 12/2004 | Kobayashi et al. | |
| 6,858,760 B2 | 2/2005 | Komoriya et al. | |
| 6,875,556 B2 | 4/2005 | Harada et al. | |
| 6,878,508 B2 | 4/2005 | Watanabe et al. | |
| 6,902,772 B2 | 6/2005 | Takeda et al. | |
| 6,908,722 B2 | 6/2005 | Ebata et al. | |
| 6,919,161 B2 | 7/2005 | Hatakeyama et al. | |
| 6,946,233 B2 | 9/2005 | Nishi et al. | |
| 6,949,678 B2 | 9/2005 | Kunimoto et al. | |
| 6,994,946 B2 | 2/2006 | Hatakeyama et al. | |
| 2001/0036591 A1 | 11/2001 | Schulz et al. | |
| 2002/0197558 A1 | 12/2002 | Ferreira et al. | |
| 2003/0113659 A1 | 6/2003 | Hatakeyama et al. | |
| 2003/0224290 A1 | 12/2003 | Kobayashi et al. | |
| 2004/0023176 A1 | 2/2004 | Harada et al. | |
| 2004/0067436 A1 | 4/2004 | Kinsho et al. | |
| 2004/0068124 A1 | 4/2004 | Hasegawa et al. | |
| 2004/0087690 A1 | 5/2004 | Lamanna et al. | |
| 2004/0106755 A1 | 6/2004 | Sumida et al. | |
| 2004/0157155 A1 | 8/2004 | Harada et al. | |
| 2004/0192867 A1 | 9/2004 | Narita et al. | |
| 2004/0241579 A1 | 12/2004 | Hamada et al. | |
| 2005/0130060 A1 | 6/2005 | Kodama et al. | |
| 2005/0142491 A1 | 6/2005 | Hasegawa et al. | |
| 2005/0250924 A1 | 11/2005 | Watanabe et al. | |
| 2007/0264596 A1* | 11/2007 | Ohsawa et al. | 430/311 |
| 2008/0032231 A1* | 2/2008 | Hatakeyama et al. | 430/270.1 |
| 2008/0085469 A1* | 4/2008 | Ohsawa et al. | 430/286.1 |

FOREIGN PATENT DOCUMENTS

| | | | |
|---|---|---|---|
| AT | 410262 B | 7/2002 | |
| DE | 295421 A5 | 10/1991 | |
| EP | 0 473 547 A1 | 4/1992 | |
| GB | 2348644 A | 10/2000 | |
| JP | 4-230645 A | 8/1992 | |
| JP | 7-25846 A | 1/1995 | |
| JP | 7-295222 B2 | 11/1995 | |
| JP | 8-311018 A | 11/1996 | |
| JP | 9-15848 A | 1/1997 | |
| JP | 9-95479 A | 4/1997 | |
| JP | 9-208554 A | 8/1997 | |
| JP | 9-230588 A | 9/1997 | |
| JP | 9-301948 A | 11/1997 | |
| JP | 11-282168 A | 10/1999 | |
| JP | 2000-122296 A | 4/2000 | |

(Continued)

OTHER PUBLICATIONS

Federal Register, Mar. 11, 2002, pp. 11008, vol. 67, No. 47.

(Continued)

*Primary Examiner*—John S Chu
(74) *Attorney, Agent, or Firm*—Birch, Stewart, Kolasch & Birch, LLP

(57) ABSTRACT

Sulfonate salts have the formula: $CF_3$—$CH(OCOR)$—$CF_2SO_3^-M^+$ wherein R is $C_1$-$C_{20}$ alkyl or $C_6$-$C_{14}$ aryl, and $M^+$ is a lithium, sodium, potassium, ammonium or tetramethylammonium ion. Onium salts, oximesulfonates and sulfonyloxyimides and other compounds derived from these sulfonate salts are effective photoacid generators in chemically amplified resist compositions.

4 Claims, 36 Drawing Sheets

FOREIGN PATENT DOCUMENTS

| | | |
|---|---|---|
| JP | 2000-159758 A | 6/2000 |
| JP | 2000-186118 A | 7/2000 |
| JP | 2000-309611 A | 11/2000 |
| JP | 2000-314956 A | 11/2000 |
| JP | 2000-327633 A | 11/2000 |
| JP | 2000-330283 A | 11/2000 |
| JP | 2001-122850 A | 5/2001 |
| JP | 2001-181221 A | 7/2001 |
| JP | 2001-233842 A | 8/2001 |
| JP | 2001-329052 A | 11/2001 |
| JP | 2002-161116 A | 6/2002 |
| JP | 2002-193887 A | 7/2002 |
| JP | 2002-193925 A | 7/2002 |
| JP | 2002-202609 A | 7/2002 |
| JP | 2002-214774 A | 7/2002 |
| JP | 2002-278053 A | 9/2002 |
| JP | 2003-2883 A | 1/2003 |
| JP | 2003-20313 A | 1/2003 |
| JP | 2003-26728 A | 1/2003 |
| JP | 2003-34706 A | 2/2003 |
| JP | 2003-64134 A | 3/2003 |
| JP | 2003-66612 A | 3/2003 |
| JP | 2003-113213 A | 4/2003 |
| JP | 2003-140332 A | 5/2003 |
| JP | 2003-316027 A | 11/2003 |
| JP | 2003-321466 A | 11/2003 |
| JP | 2004-2252 A | 1/2004 |
| JP | 2004-35671 A | 2/2004 |
| JP | 2004-59844 A | 2/2004 |
| JP | 2004-62175 A | 2/2004 |
| JP | 2004-83873 A | 3/2004 |
| JP | 2004-83900 A | 3/2004 |
| JP | 2004-99689 A | 4/2004 |
| JP | 2004-115486 A | 4/2004 |
| JP | 2004-115762 A | 4/2004 |
| JP | 2004-124082 A | 4/2004 |
| JP | 2004-143153 A | 5/2004 |
| JP | 2004-145048 A | 5/2004 |
| JP | 2004-190036 A | 7/2004 |
| JP | 2004-217533 A | 8/2004 |
| JP | 2004-231815 A | 8/2004 |
| JP | 2004-244439 A | 9/2004 |
| JP | 2004-252405 A | 9/2004 |
| JP | 2004-256562 A | 9/2004 |
| JP | 2004-292781 A | 10/2004 |
| JP | 2004-531749 A | 10/2004 |
| JP | 2004-307447 A | 11/2004 |
| JP | 2004-323422 A | 11/2004 |
| JP | 2004-331853 A | 11/2004 |
| JP | 2004-331854 A | 11/2004 |
| JP | 2004-352743 A | 12/2004 |
| JP | 2004-354417 A | 12/2004 |
| JP | 2005-8765 A | 1/2005 |
| JP | 2005-29527 A | 2/2005 |
| JP | 2005-29539 A | 2/2005 |
| JP | 2005-84365 A | 3/2005 |
| WO | WO 02/42845 A2 | 5/2002 |
| WO | WO-2004/41762 A1 | 5/2004 |
| WO | WO-2004/074242 A3 | 9/2004 |
| WO | WO-2004/96786 A1 | 11/2004 |
| WO | WO-2005/05370 A1 | 1/2005 |
| WO | WO-2005/05404 A1 | 1/2005 |

OTHER PUBLICATIONS

Federal Register, Dec. 9, 2002, pp. 72854, vol. 67, No. 236.
Journal of Photopolymer Science and Technology, 2004, pp. 587, vol. 17, No. 4.
Tetrahedron Lett., 1988, pp. 4119, vol. 29, No. 33.
Wagner et al., Synthetic Organic Chemistry, 1965, pp. 813-814, John Wiley & Sons.
The Chemistry of Sulfonium Group Part 1, 1981, John Wiley & Sons, CH. 11, pp. 267.
Advances in Photochemistry, 1992, vol. 17, John Wiley & Sons, pp. 313.
J. Org. Chem., 1988, vol. 53, pp. 5571-5573.
J. Photopolym. Sci. and Tech., (1995), vol. 8, No. 1, pp. 43-46.
J. Photopolym. Sci. and Tech., (1996), vol. 9, pp. 29-30.

* cited by examiner

SULFONATE SALTS AND DERIVATIVES, PHOTOACID GENERATORS, RESIST COMPOSITIONS, AND PATTERNING PROCESS

CROSS-REFERENCE TO RELATED APPLICATION

This non-provisional application claims priority under 35 U.S.C. §119(a) on Patent Application Nos. 2005-109903 and 2005-316096 filed in Japan on Apr. 6, 2005 and Oct. 31, 2005, respectively, the entire contents of which are hereby incorporated by reference.

TECHNICAL FIELD

This invention relates to photoacid generators, resist compositions comprising the same, and a patterning process using the same. Mo[5re particularly, it relates to novel sulfonate salts and derivatives thereof suitable for use as photoacid generators for resist compositions.

BACKGROUND OF THE INVENTION

While a number of recent efforts are being made to achieve a finer pattern rule in the drive for higher integration and operating speeds in LSI devices, DUV and VUV lithography is thought to hold particular promise as the next generation in microfabrication technology. In particular, photolithography using an ArF excimer laser as the light source is thought requisite to the micropatterning technique capable of achieving a feature size of 0.13 µm or less.

In the photolithography using an ArF excimer laser (wavelength 193 nm) as the light source, a high sensitivity resist material capable of achieving a high resolution at a small dose of exposure is needed to prevent the degradation of precise and expensive optical system materials. Among several measures for providing high sensitivity resist material, the most common is to select each component which is highly transparent at the wavelength of 193 nm. For example, poly(meth)acrylic acid and derivatives thereof, norbornene-maleic anhydride alternating copolymers, polynorbornene and metathesis ring-opening polymers have been proposed as the base resin. This choice is effective to some extent in that the transparency of a resin alone is increased.

Studies have also been made on photoacid generators. In prior art chemically amplified resist compositions for lithography using KrF excimer laser, photoacid generators capable of generating alkyl- or aryl-sulfonic acid are used. However, the use of these photoacid generators in chemically amplified resist compositions for ArF lithography results in an insufficient acid strength to scissor acid labile groups on the resin, a failure of resolution or a low sensitivity, and is not suited for the microfabrication of microelectronic devices.

For the above reason, photoacid generators capable of generating perfluoroalkylsulfonic acid having a high acid strength are generally used in ArF chemically amplified resist compositions. These photoacid generators capable of generating perfluoroalkylsulfonic acid have already been developed for use in the KrF resist compositions. For instance, JP-A 2000-122296 and U.S. Pat. No. 6,048,672 (or JP-A 11-282168) describe photoacid generators capable of generating perfluorohexanesulfonic acid, perfluorooctanesulfonic acid, perfluoro-4-ethylcyclohexanesulfonic acid, and perfluorobutanesulfonic acid. JP-A 2002-214774, US Patent Application 2003-0113659 A1 (JP-A 2003-140332) and US Patent Application 2002-0197558 A1 describe novel photoacid generators capable of generating perfluoroalkyl ether sulfonic acids.

On the other hand, perfluorooctanesulfonic acid and homologues thereof (collectively referred to as PFOS) are considered problematic with respect to their stability (or non-degradability) due to C—F bonds, and biological concentration and accumulation due to hydrophobic and lipophilic natures. The US EPA adopted Significant New Use Rule, listing 13 PFOS-related chemical substances and further listing 75 chemical substances although their use in the photoresist field is excluded. See Federal Register/Vol. 67, No. 47, page 11008/Monday, Mar. 11, 2002, and Federal Register/Vol. 67, No. 236, page 72854/Monday, Dec. 9, 2002.

Facing the PFOS-related problems, manufacturers made efforts to develop partially fluorinated alkyl sulfonic acids having a reduced degree of fluorine substitution. For instance, JP-A 2004-531749 describes the development of $\alpha,\alpha$-difluoroalkylsulfonic acid salts from $\alpha,\alpha$-difluoroalkene and a sulfur compound and discloses a resist composition comprising a photoacid generator which generates such sulfonic acid upon irradiation, specifically di(4-tert-butylphenyl)iodonium 1,1-difluoro-1-sulfonate-2-(1-naphthyl)ethylene. JP-A 2004-2252 describes the development of $\alpha,\alpha,\beta,\beta$-tetrafluoroalkylsulfonic acid salts from $\alpha,\alpha,\beta,\beta$-tetrafluoro-$\alpha$-iodoalkane and sulfur compound and discloses a photoacid generator capable of generating such a sulfonic acid and a resist composition comprising the same. JP-A 2004-307387 discloses 2-(bicyclo[2.2.1]hept-2-yl)-1,1-difluoroethylsulfonic acid salts and a method of preparing the same.

The substances disclosed in these patents have a reduced degree of fluorine substitution, but suffer from several problems. They are insufficient from the standpoint of decomposition because they do not have decomposable substituent groups such as ester structure. A certain limit is imposed on the molecular design for changing the size of alkylsulfonic acid. The starting materials containing fluorine are expensive.

The ArF lithography started partial use from the fabrication of 130-nm node devices and became the main lithography since 90-nm node devices. Although lithography using $F_2$ laser (157 nm) was initially thought promising as the next lithography for 45-nm node devices, its development was retarded by several problems including the quality of $CaF_2$ single crystal used in projection lens, a need for hard pellicle that requires design changes of the optical system, and low etch resistance of resists. A highlight was suddenly placed on ArF immersion lithography. See Journal of Photopolymer Science and Technology, Vol. 17, No. 4, p587 (2004).

The resolution of a projection lens through which a pattern image is projected onto a wafer increases as its numerical aperture (NA) increases. In the immersion lithography, the intervention of a liquid having a higher refractive index than air between the projection lens and the wafer allows the projection lens to be designed to a NA of 1.0 or higher, achieving a higher resolution. As the liquid, water having a refractive index of 1.4366 is used while alcohols such as ethylene glycol and glycerin are under investigation.

Regrettably, the immersion lithography gives rise to the problem that the resist pattern after development can collapse or deform into a T-top profile. Also, minute water droplets are left on the resist and wafer after the immersion exposure, which can often cause damages and defects to the resist pattern profile. There exists a need for a patterning process which can form a satisfactory resist pattern after development according to the immersion lithography.

DISCLOSURE OF THE INVENTION

The photoacid generator (PAG) produces an acid which must satisfy many requirements including a sufficient acid strength to cleave acid labile groups in a resist material, an adequate diffusion in the resist material, low volatility, minimal dissolution in water, and good degradability in that it is decomposed away after the expiration of its role in lithography without imposing a load to the environment. No acids produced by prior art PAGs satisfy these requirements.

An object of the invention is to provide sulfonate salts and derivatives thereof which have solved the problems of prior art photoacid generators, and especially restrain dissolution in water during ArF immersion exposure, and are effectively used in the immersion lithography and thus suitable as a photoacid generator in resist material or a precursor thereof. Another object is to provide a photoacid generator, a resist composition, and a patterning process.

The inventors have found that by starting with 1,1,1,3,3,3-hexafluoro-2-propanol which is readily available in the industry, and reacting substituted or unsubstituted 1,1,1,3,3,3-hexafluoropropen-2-yl aliphatic carboxylic acid esters or aromatic carboxylic acid esters with sulfur compounds such as sodium sulfite or sodium hydrogen sulfite, there are formed 1,1,3,3,3-pentafluoro-2-acyloxypropane-1-sulfonate salts or 1,1,3,3,3-pentafluoro-2-arylcarbonyloxypropane-1-sulfonate salts; that onium salts, oximesulfonates and sulfonyloxyimides and other compounds derived from these sulfonate salts are effective photoacid generators in chemically amplified resist compositions. The present invention is predicated on this finding.

The present invention provides sulfonate salts, derivatives thereof, photoacid generators, resist compositions and a patterning process, defined below.

[1] A sulfonate salt having the general formula (1):

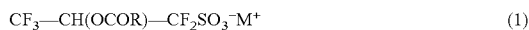

$$CF_3—CH(OCOR)—CF_2SO_3^-M^+ \quad (1)$$

wherein R is a substituted or unsubstituted, straight, branched or cyclic $C_1$-$C_{20}$ alkyl group or a substituted or unsubstituted $C_6$-$C_{14}$ aryl group, and M$^+$ is a lithium, sodium, potassium, ammonium or tetramethylammonium ion.

[2] A photoacid generator for chemically amplified resist compositions which generates a sulfonic acid upon exposure to high-energy radiation selected from UV, deep-UV, electron beam, x-ray, excimer laser, gamma-ray and synchrotron radiation, said sulfonic acid having the general formula (1a):

$$CF_3—CH(OCOR)—CF_2SO_3^-H^+ \quad (1a)$$

wherein R is as defined above.

[3] A sulfonium salt having the general formula (2):

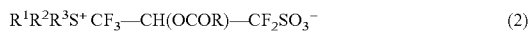

$$R^1R^2R^3S^+ CF_3—CH(OCOR)—CF_2SO_3^- \quad (2)$$

wherein R is as defined above, $R^1$, $R^2$ and $R^3$ are each independently selected from the class consisting of substituted or unsubstituted, straight or branched $C_1$-$C_{10}$ alkyl, alkenyl and oxoalkyl groups, and substituted or unsubstituted $C_6$-$C_{18}$ aryl, aralkyl and aryloxoalkyl groups, or any two or more of $R^1$, $R^2$ and $R^3$ may bond together to form a ring with the sulfur atom.

[4] A sulfonium salt having the general formula (2a):

$$R'—(O)_n—PhS^+Ph_2\ CF_3—CH(OCOR)—CF_2SO_3^- \quad (2a)$$

wherein R is as defined above, R' is a substituted or unsubstituted, straight, branched or cyclic $C_1$-$C_{20}$ alkyl or alkenyl group or a substituted or unsubstituted $C_6$-$C_{14}$ aryl group, Ph is phenyl, and n is 0 or 1.

[5] A iodonium salt having the general formula (2b):

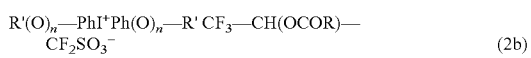

$$R'(O)_n—PhI^+Ph(O)_n—R'\ CF_3—CH(OCOR)—CF_2SO_3^- \quad (2b)$$

wherein R, R', Ph and n are as defined above.

[6] A N-sulfonyloxyimide compound having the general formula (3a):

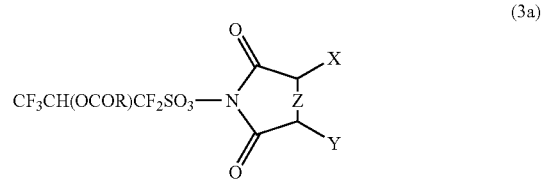

(3a)

wherein R is as defined above, X and Y are each independently hydrogen or a substituted or unsubstituted $C_1$-$C_6$ alkyl group, or X and Y may bond together to form a saturated or unsaturated $C_6$-$C_{12}$ ring with the carbon atoms to which they are attached, and Z is a single bond, double bond, methylene group or oxygen atom.

[7] An oxime sulfonate compound having the general formula (3b):

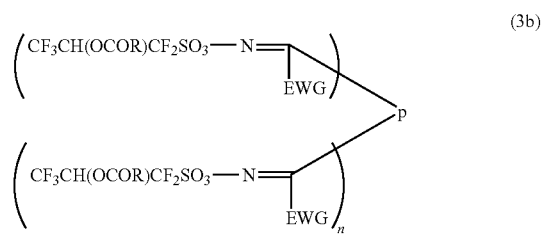

(3b)

wherein R is as defined above; n is 0 or 1; when n is 0, p is a substituted or unsubstituted $C_1$-$C_{20}$ alkyl group or a substituted or unsubstituted $C_6$-$C_{12}$ aryl group; when n is 1, p is a substituted or unsubstituted $C_1$-$C_{20}$ alkylene group or a substituted or unsubstituted $C_6$-$C_{12}$ arylene group; EWG is a cyano, trifluoromethyl, perfluoroethyl, perfluoropropyl, 5H-perfluoropentyl, 6H-perfluorohexyl, nitro or methyl group, and when n is 1, two EWG's may bond together to form a ring of 6 carbon atoms with the carbon atoms to which they are attached.

[8] A resist composition comprising a base resin, an acid generator, and a solvent, said acid generator comprising a photoacid generator which generates a sulfonic acid having formula (1a) as set forth in [2].

[9] The resist composition of [8], wherein said base resin is at least one polymer selected from the group consisting of poly (meth)acrylic acid and derivatives thereof, alternating copolymers of a cycloolefin derivative and maleic anhydride, copolymers of ternary or more components comprising a cycloolefin derivative, maleic anhydride, and polyacrylic acid or derivatives thereof, cycloolefin derivative-α-trifluoromethyl acrylate copolymers, polynorbornene, ring-opening metathesis polymers, and hydrogenated ring-opening metathesis polymers.

[10] The resist composition of [8], wherein said base resin is a polymeric structure containing silicon atoms.

[11] The resist composition of [8], wherein said base resin is a polymeric structure containing fluorine atoms.

[12] A chemically amplified positive resist composition comprising a base resin as set forth in [9], [10] or [11], a photoacid generator which generates a sulfonic acid having formula (1a) as set forth in [2], and a solvent, wherein said base resin is insoluble or substantially insoluble in a liquid developer, and becomes soluble under the action of the acid.

[13] The chemically amplified positive resist composition of [12], further comprising a basic compound.

[14] The chemically amplified positive resist composition of [12] or [13], further comprising a dissolution inhibitor.

[15] A process for forming a pattern comprising the steps of applying the resist composition of any one of [8] to [14] onto a substrate to form a coating; heat treating the coating and exposing it to high-energy radiation having a wavelength of up to 200 nm through a photomask; and optionally heat treating and developing the exposed coating with a developer.

[16] The process of [15], wherein the exposing step relies on immersion lithography comprising directing radiation from an ArF excimer laser having a wavelength of 193 nm through a projection lens, with a liquid such as water, glycerin or ethylene glycol intervening between the coated substrate and the projection lens.

BENEFITS OF THE INVENTION

The sulfonic acids of the invention have a wide spectrum of molecular design because the inclusion of an ester moiety within the molecule allows for easy incorporation of substituent groups including less bulky acyl groups, bulky acyl groups, benzoyl groups, naphthoyl groups and anthranyl groups. The photoacid generators that generate these sulfonic acids perform well without raising problems during the device fabrication process including coating, pre-baking, exposure, post-exposure baking, and developing steps. The dissolution of sulfonic acids in water during the ArF immersion lithography is minimized, and the influence of water droplets left on the wafer is minimized, with few defects being found. In the disposal of resist-containing waste liquid after the device fabrication, ester moieties are subject to alkaline hydrolysis so that the sulfonic acids are transformed into less accumulative compounds of lower molecular weight. In the disposal by combustion, the sulfonic acids are more combustible because of a low degree of fluorine substitution.

DESCRIPTION OF THE PREFERRED EMBODIMENTS

Figure 1:
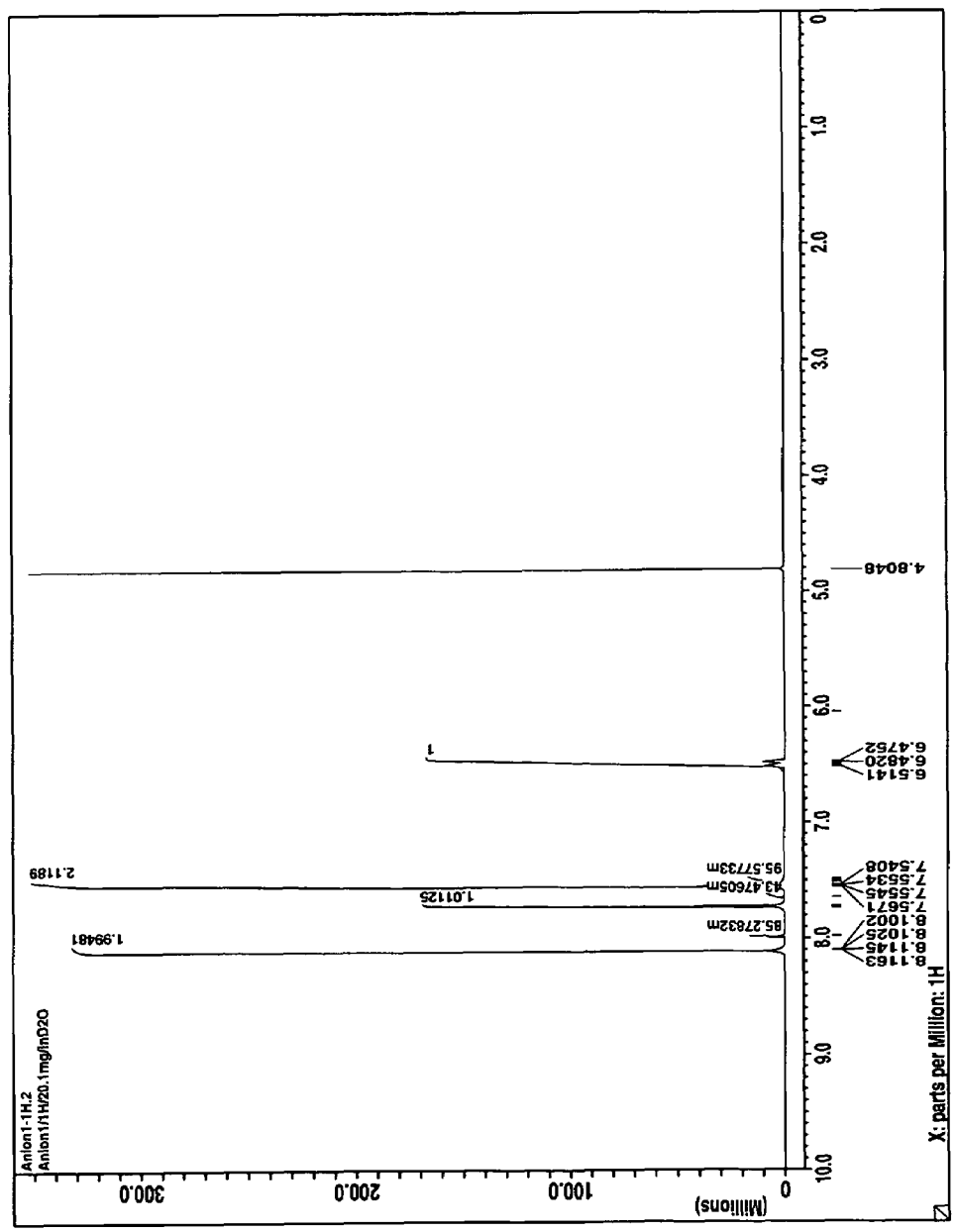
FIG. 1 is a diagram showing the $^1$H-NMR/D$_2$O spectrum of Anion 1 in Synthesis Example 9.

The notation (Cn-Cm) means a group containing from n to m carbon atoms per group.

Sulfonate Salt

The sulfonate salt of the invention has the general formula (1):

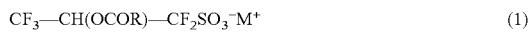

CF$_3$—CH(OCOR)—CF$_2$SO$_3^-$M$^+$ (1)

wherein R is a substituted or unsubstituted, straight, branched or cyclic C$_1$-C$_{20}$ alkyl group or a substituted or unsubstituted C$_6$-C$_{14}$ aryl group, and M$^+$ is a lithium, sodium, potassium, ammonium or tetramethylammonium ion.

In formula (1), R is a substituted or unsubstituted, straight, branched or cyclic C$_1$-C$_{20}$ alkyl group or a substituted or unsubstituted C$_6$-C$_{14}$ aryl group. Examples of suitable alkyl and aryl groups include methyl, ethyl, n-propyl, sec-propyl, cyclopropyl, n-butyl, sec-butyl, iso-butyl, tert-butyl, n-pentyl, cyclopentyl, n-hexyl, cyclohexyl, n-octyl, n-decyl, n-dodecyl, 1-adamantyl, 2-adamantyl, bicyclo[2.2.1]hepten-2-yl, phenyl, 4-methoxyphenyl, 4-tert-butylphenyl, 4-biphenyl, 1-naphthyl, 2-naphthyl, 10-anthranyl and 2-furanyl. M$^+$ is a lithium ion, sodium ion, potassium ion, ammonium ion or tetramethylammonium ion.

For simplicity of synthesis and ease of isolation, only lithium, sodium, potassium, ammonium and tetramethylammonium salts are specified herein as the sulfonate salt. Nevertheless, salts of divalent cations like calcium and magnesium salts are acceptable. No particular limit is imposed on sulfonate salts as long as they can exist as stable salts.

Preferred among R groups are tert-butyl, cyclohexyl, 1-adamantyl, phenyl, 4-tert-butylphenyl, 4-methoxyphenyl, 4-biphenyl, 1-naphthyl and 2-naphthyl. More preferred are tert-butyl, cyclohexyl, phenyl and 4-tert-butylphenyl.

Photoacid Generator

The photoacid generators of the invention are compounds derived from the sulfonate salts having formula (1), typically sulfonium salts, iodonium salts, oximesulfonates and sulfonyloxyimides. These compounds are sensitive to high-energy radiation such as UV, deep-UV, electron beam, x-ray, excimer laser, gamma-ray and synchrotron radiation and generate sulfonic acids having the general formula (1a) so that they are useful as photoacid generators in chemically amplified resist compositions.

CF$_3$—CH(OCOR)—CF$_2$SO$_3^-$H$^+$ (1a)

Herein R is a substituted or unsubstituted, straight, branched or cyclic C$_1$-C$_{20}$ alkyl group or a substituted or unsubstituted C$_6$-C$_{14}$ aryl group.

Examples of R in formula (1a) are the same as described for formula (1). Illustrative examples of the sulfonic acid are given below.

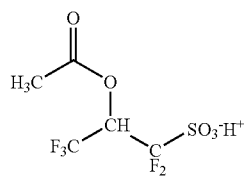

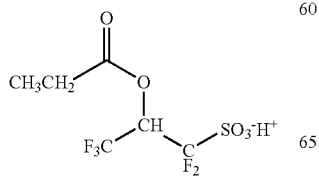

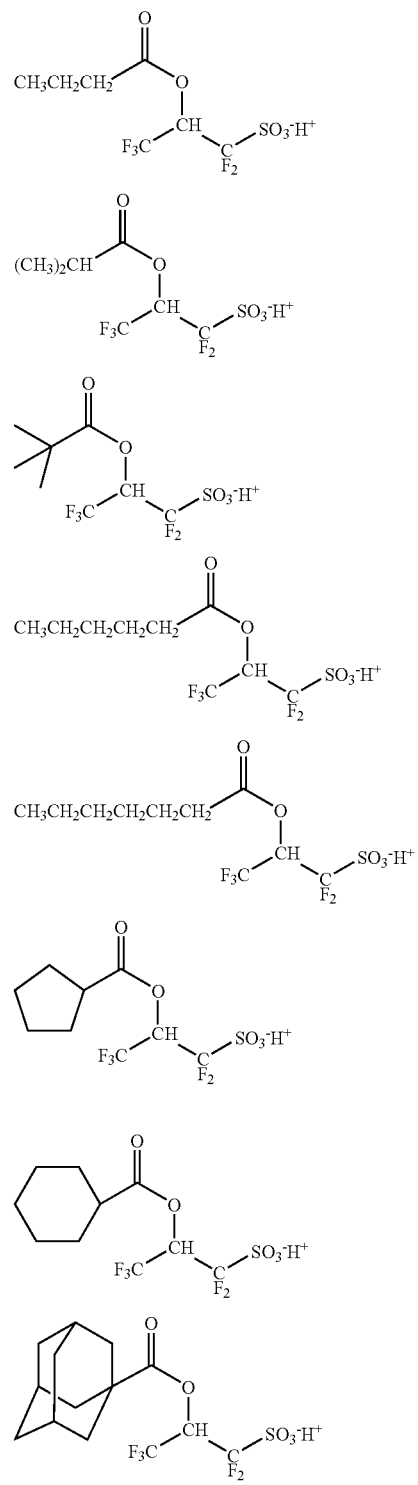

-continued

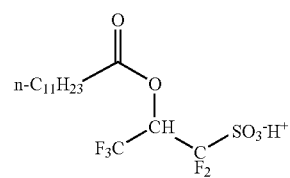

-continued

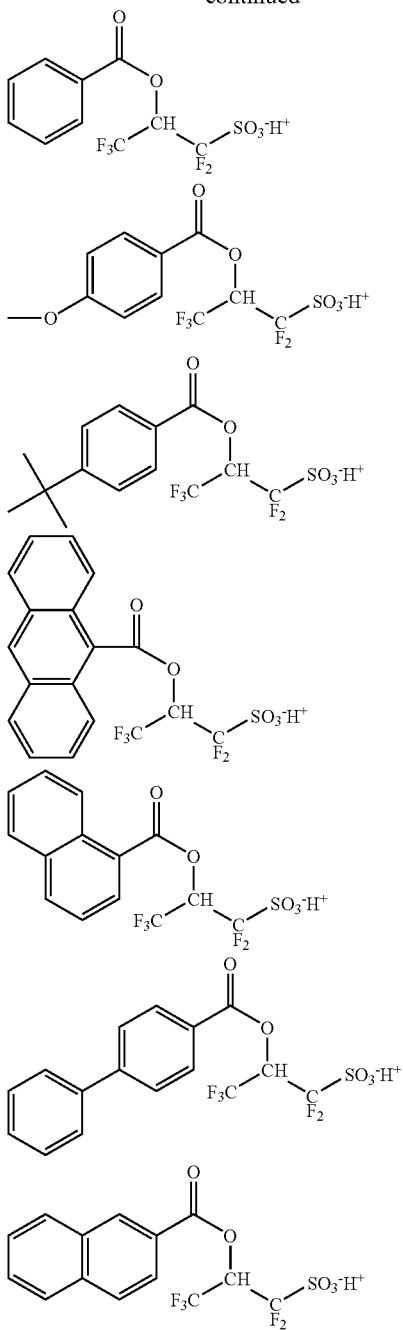

Of the groups represented by R in formula (1a), tert-butyl, cyclohexyl, 1-adamantyl, phenyl, 4-tert-butylphenyl, 4-biphenyl, 1-naphthyl and 2-naphthyl are preferred.

Sulfonium Salt

The sulfonium salt of the invention has the general formula (2):

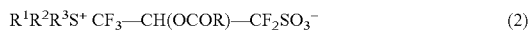

wherein R is a substituted or unsubstituted, straight, branched or cyclic $C_1$-$C_{20}$ alkyl group or a substituted or unsubstituted $C_6$-$C_{14}$ aryl group, $R^1$, $R^2$ and $R^3$ are each independently selected from among substituted or unsubstituted, straight or branched $C_1$-$C_{10}$ alkyl, alkenyl and oxoalkyl groups, and substituted or unsubstituted $C_6$-$C_{18}$ aryl, aralkyl and aryloxoalkyl groups, or any two or more of $R^1$, $R^2$ and $R^3$ may bond together to form a ring with the sulfur atom.

In formula (2), examples of R are the same as described for formula (1). $R^1$, $R^2$ and $R^3$ are each independently selected from among substituted or unsubstituted, straight or branched $C_1$-$C_{10}$ alkyl, alkenyl and oxoalkyl groups, and substituted or unsubstituted $C_6$-$C_{18}$ aryl, aralkyl and aryloxoalkyl groups, or any two or more of $R^1$, $R^2$ and $R^3$ may bond together to form a ring with the sulfur atom. Suitable alkyl groups include methyl, ethyl, propyl, isopropyl, n-butyl, sec-butyl, tert-butyl, pentyl, hexyl, heptyl, octyl, cyclopentyl, cyclohexyl, cycloheptyl, cyclopropylmethyl, 4-methylcyclohexyl, cyclohexylmethyl, norbornyl, and adamantyl. Suitable alkenyl groups include vinyl, allyl, propenyl, butenyl, hexenyl, and cyclohexenyl. Suitable oxoalkyl groups include 2-oxocyclopentyl, 2-oxocyclohexyl, 2-oxopropyl, 2-oxoethyl, 2-cyclopentyl-2-oxoethyl, 2-cyclohexyl-2-oxoethyl, and 2-(4-methyl-cyclohexyl)-2-oxoethyl. Suitable aryl groups include phenyl, naphthyl, and thienyl; 4-hydroxyphenyl; alkoxyphenyl groups such as p-methoxyphenyl, m-methoxyphenyl, o-methoxyphenyl, p-ethoxyphenyl, p-tert-butoxyphenyl, and m-tert-butoxyphenyl; alkylphenyl groups such as 2-methylphenyl, 3-methylphenyl, 4-methylphenyl, ethylphenyl, 4-tert-butylphenyl, 4-butylphenyl, and 2,4-dimethylphenyl; alkylnaphthyl groups such as methylnaphthyl and ethylnaphthyl; alkoxynaphthyl groups such as methoxynaphthyl and ethoxynaphthyl; dialkylnaphthyl groups such as dimethylnaphthyl and diethylnaphthyl; and dialkoxynaphthyl groups such as dimethoxynaphthyl and diethoxynaphthyl. Suitable aralkyl groups include benzyl, 1-phenylethyl and 2-phenylethyl. Suitable aryloxoalkyl groups include 2-aryl-2-oxoethyl groups such as 2-phenyl-2-oxoethyl, 2-(1-naphthyl)-2-oxoethyl, and 2-(2-naphthyl)-2-oxoethyl. When two or more of $R^1$, $R^2$ and $R^3$ bond together to form a ring structure with the sulfur atom, 1,4-butylene and 3-oxa-1,5-pentylene are exemplary of each. Also included are aryl groups having polymerizable substituent radicals such as acryloyloxy and methacryloyloxy radicals, examples of which are 4-(acryloyloxy)phenyl, 4-(methacryloyloxy)phenyl, 4-vinyloxyphenyl, and 4-vinylphenyl groups.

Illustrative examples of the sulfonium cation include triphenylsulfonium, 4-hydroxyphenyldiphenylsulfonium, bis(4-hydroxyphenyl)phenylsulfonium, tris(4-hydroxyphenyl)sulfonium, (4-tert-butoxyphenyl)diphenylsulfonium, bis(4-tert-butoxyphenyl)phenylsulfonium, tris(4-tert-butoxyphenyl)sulfonium, (3-tert-butoxyphenyl)diphenylsulfonium, bis(3-tert-butoxyphenyl)phenylsulfonium, tris(3-tert-butoxyphenyl)sulfonium, (3,4-di-tert-butoxyphenyl)diphenylsulfonium, bis(3,4-di-tert-butoxyphenyl)phenylsulfonium, tris(3,4-di-tert-butoxyphenyl)sulfonium, diphenyl(4-thiophenoxyphenyl)sulfonium, (4-tert-butoxycarbonylmethyloxyphenyl)diphenylsulfonium, tris(4-tert-butoxycarbonylmethyloxyphenyl)sulfonium, (4-tert-butoxyphenyl)bis(4-dimethylaminophenyl)sulfonium, tris(4-dimethylaminophenyl)sulfonium, 2-naphthyldiphenylsulfonium, dimethyl-2-naphthylsulfonium, 4-hydroxyphenyldimethylsulfonium, 4-methoxyphenyldimethylsulfonium, trimethylsulfonium, 2-oxocyclohexylcyclohexylmethylsulfonium, trinaphthylsulfonium, tribenzylsulfonium, diphenylmethylsulfonium, dimethylphenylsulfonium, 2-oxo-2-phenylethylthiacyclopentanium, diphenyl-2-thienylsulfonium, 4-n-butoxynaphthyl-1-thiacyclopentanium, 2-n-butoxynaphthyl-1-thiacyclopentanium, 4-methoxynaphthyl-1-thiacyclopentanium, and 2-methoxynaphthyl-1- thiacyclopentanium. Preferred cations are triphenylsulfonium, 4-tert-butylphenyldiphenylsulfonium, 4-tert-butoxyphenyldiphenylsulfonium, tris(4-tert-butylphenyl)sulfonium, and (4-tert-butoxycarbonylmethyloxyphenyl)diphenylsulfonium.

Also included are 4-(methacryloyloxy)phenyldiphenylsulfonium, 4-(acryloyloxy)phenyldiphenylsulfonium, 4-(methacryloyloxy)phenyldimethylsulfonium, 4-(acryloyloxy)phenyldimethylsulfonium, and the like. For these polymerizable sulfonium cations, reference may be made to JP-A 4-230645 and JP-A 2005-84365. These polymerizable sulfonium salts may be used as a monomer in forming a polymer to be described later.

In one embodiment, the sulfonium salt has the general formula (2a):

R'—(O)$_n$—PhS$^+$Ph$_2$ CF$_3$—CH(OCOR)—CF$_2$SO$_3^-$ (2a)

wherein R is a substituted or unsubstituted, straight, branched or cyclic $C_1$-$C_{20}$ alkyl group or a substituted or unsubstituted $C_6$-$C_{14}$ aryl group, R' is a substituted or unsubstituted, straight, branched or cyclic $C_1$-$C_{20}$ alkyl or alkenyl group or a substituted or unsubstituted $C_6$-$C_{14}$ aryl group, Ph is phenyl, and n is 0 or 1.

In formula (2a), examples of R are the same as described for formula (1). The subscript n is 0 or 1. The substitution position of R'—(O)$_n$— group is not particularly limited, but is preferably 4- or 3-position on the phenyl group, and more preferably 4-position. Examples of groups represented by R' include methyl, ethyl, n-propyl, sec-propyl, cyclopropyl, n-butyl, sec-butyl, iso-butyl, tert-butyl, n-pentyl, cyclopentyl, n-hexyl, cyclohexyl, n-octyl, n-decyl, n-dodecyl, 1-adamantyl, 2-adamantyl, bicyclo[2.2.1]hepten-2-yl, phenyl, 4-methoxyphenyl, 4-tert-butylphenyl, 4-biphenyl, 1-naphthyl, 2-naphthyl, 10-anthranyl, and 2-furanyl. In the case of n=1, acryloyl, methacryloyl, vinyl, and allyl are exemplary of R'.

Illustrative examples of the sulfonium cation include 4-methylphenyldiphenylsulfonium, 4-ethylphenyldiphenylsulfonium, 4-tert-butylphenyldiphenylsulfonium, 4-cyclohexylphenyldiphenylsulfonium, 4-n-hexylphenyldiphenylsulfonium, 4-n-octylphenyldiphenylsulfonium, 4-methoxyphenyldiphenylsulfonium, 4-ethoxyphenyldiphenylsulfonium, 4-tert-butoxyphenyldiphenylsulfonium, 4-cyclohexyloxyphenyldiphenylsulfonium, 4-n-hexyloxyphenyldiphenylsulfonium, 4-n-octyloxyphenyldiphenylsulfonium, 4-dodecyloxyphenyldiphenylsulfonium, 4-trifluoromethylphenyldiphenylsulfonium, 4-trifluoromethyloxyphenyldiphenylsulfonium, 4-tert-butoxycarbonylmethyloxyphenyldiphenylsulfonium, 4-(methacryloyloxy)phenyldiphenylsulfonium, 4-(acryloyloxy)phenyldiphenylsulfonium, 4-(methacryloyloxy)phenyldimethylsulfonium, and 4-(acryloyloxy)phenyldimethylsulfonium.

Iodonium Salt

A further embodiment of the invention is a iodonium salt having the general formula (2b):

R'(O)$_n$—PhI$^+$Ph(O)$_n$—R' CF$_3$—CH(OCOR)—
CF$_2$SO$_3^-$ (2b)

wherein R is a substituted or unsubstituted, straight, branched or cyclic $C_1$-$C_{20}$ alkyl group or a substituted or unsubstituted $C_6$-$C_{14}$ aryl group, R' is a substituted or unsubstituted, straight, branched or cyclic $C_1$-$C_{20}$ alkyl or alkenyl group or a substituted or unsubstituted $C_6$-$C_{14}$ aryl group, Ph is phenyl, and n is 0 or 1.

R, R', n and Ph in formula (2b) are as defined above. The substitution position of R'—(O)$_n$— group is not particularly limited, but is preferably 4- or 3-position on the phenyl group, and more preferably 4-position.

Illustrative examples of the iodonium cation include bis(4-methylphenyl)iodonium, bis(4-ethylphenyl)iodonium, bis(4-tert-butylphenyl)iodonium, bis(4-(1,1-dimethylpropyl)phenyl)iodonium, 4-methoxyphenylphenyliodonium, 4-tert-butoxyphenylphenyliodonium, 4-acryloyloxyphenylphenyliodonium, and 4-methacryloyloxyphenylphenyliodonium, with the bis(4-tert-butylphenyl)iodonium being preferred.

N-sulfonyloxyimide

A further embodiment of the invention is a N-sulfonyloxyimide compound having the general formula (3a):

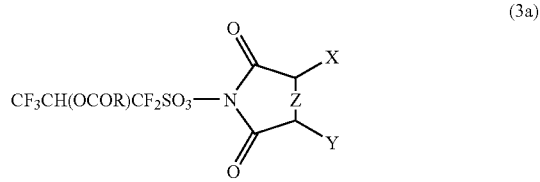

(3a)

wherein R is a substituted or unsubstituted, straight, branched or cyclic $C_1$-$C_{20}$ alkyl group or a substituted or unsubstituted $C_6$-$C_{14}$ aryl group; X and Y are each independently hydrogen or a substituted or unsubstituted $C_1$-$C_6$ alkyl group, or X and Y may bond together to form a saturated or unsaturated $C_6$-$C_{12}$ ring with the carbon atoms to which they are attached; and Z is a single bond, double bond, methylene group or oxygen atom.

Illustrative examples of the imide skeleton excluding the sulfonate moiety are given below. For the imide skeleton, reference may be made to JP-A 2003-252855.

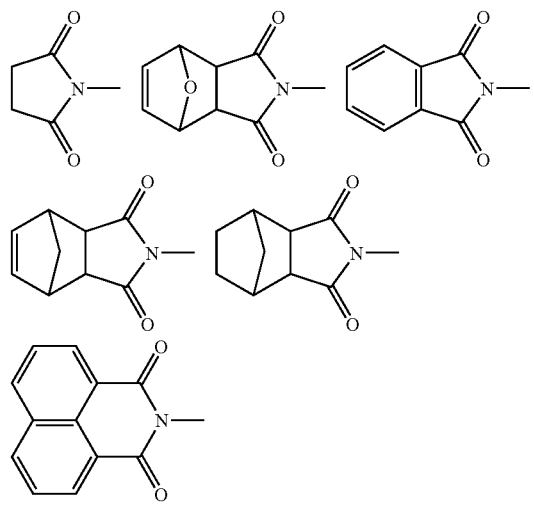

Oxime Sulfonate

A further embodiment of the invention is an oxime sulfonate compound having the general formula (3b):

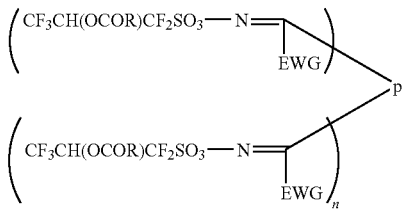
(3b)

wherein R is a substituted or unsubstituted, straight, branched or cyclic $C_1$-$C_{20}$ alkyl group or a substituted or unsubstituted $C_6$-$C_{14}$ aryl group, and n is 0 or 1; when n is 0, p is a substituted or unsubstituted $C_1$-$C_{20}$ alkyl group or a substituted or unsubstituted $C_6$-$C_{12}$ aryl group; when n is 1, p is a substituted or unsubstituted $C_1$-$C_{20}$ alkylene group or a substituted or unsubstituted $C_6$-$C_{12}$ arylene group; and EWG is a cyano, trifluoromethyl, perfluoroethyl, perfluoropropyl, 5H-perfluoropentyl, 6H-perfluorohexyl, nitro or methyl group, and when n is 1, two EWG's may bond together to form a ring of 6 carbon atoms with the carbon atoms to which they are attached.

The skeletons of these oxime sulfonates are described in U.S. Pat. No. 6,261,738, JP-A 9-95479, JP-A 9-208554, JP-A 9-230588, Japanese Patent No. 2,906,999, JP-A 9-301948, JP-A 2000-314956, JP-A 2001-233842, and International Publication 2004-074242.

Exemplary skeletons of oxime sulfonates excluding the sulfonate moiety are given below.

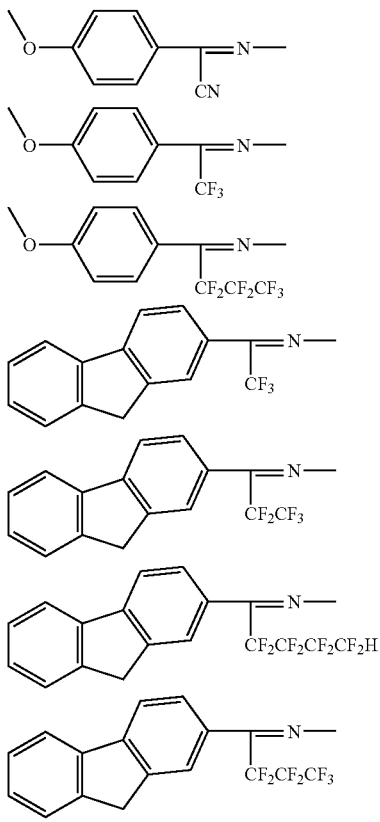

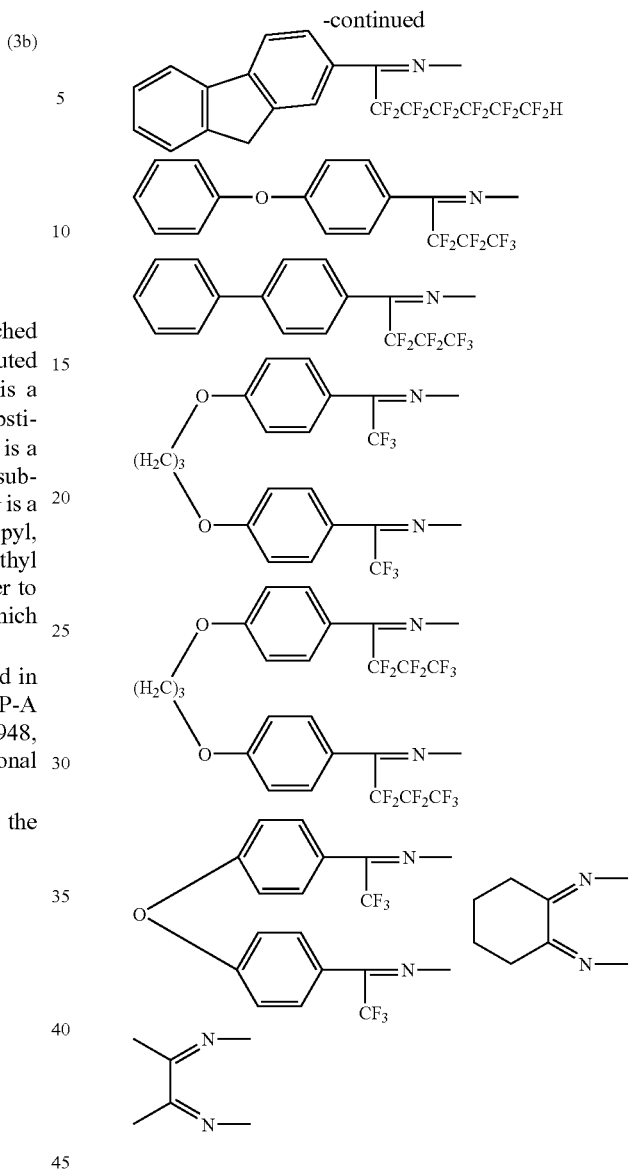

Described below is how to synthesize the sulfonate salt having formula (1).

Synthesis may be carried out by reacting 1,1,3,3,3-pentafluoropropen-2-yl aliphatic carboxylate or aromatic carboxylate, typically 1,1,3,3,3-pentaflubropropen-2-yl benzoate which was developed by Nakai et al. using 1,1,1,3,3,3-hexafluoro-2-propanol as the starting reactant (see Tetrahedron Lett., Vol. 29, 4119 (1988)), with sodium hydrogen sulfite or sodium sulfite in the presence of a radical initiator such as azobisisobutyronitrile or benzoyl peroxide in a solvent which is water or alcohol or a mixture thereof. See R. B. Wagner et al., Synthetic Organic Chemistry, pp. 813-814, John Wiley & Sons, Inc. (1965). More specifically, the carboxylic acid ester moiety of a sulfonate salt having formula (1) obtained by the above method or a sulfonate salt having formula (2), (2a), (2b), (3a) or (3b) is subjected to hydrolysis using alkali such as sodium hydroxide or potassium hydroxide or solvolysis using alcohol and base, and then reacted with any appropriate one of aliphatic carboxylic halides, aliphatic carboxylic anhydrides, aromatic carboxylic halides, and aromatic carboxylic anhydrides, whereby a sulfonate salt having formula (1) or a photoacid generator having formula (2), (2a), (2b), (3a) or (3b) having a different carboxylic acid ester structure from the original carboxylic acid ester structure.

In preparing the sulfonate salt described above, a sulfonate salt of the following general formula (1') or (1") corresponding to the sulfonate salt of formula (1) with hydrogen fluoride being eliminated can sometimes form as well.

$$CF_3-C(OCOR)=CFSO_3^- M^+ \quad (1')$$

$$CF_2=C(OCOR)CF_2SO_3^- M^+ \quad (1'')$$

Herein, R is a substituted or unsubstituted, straight, branched or cyclic $C_1$-$C_{20}$ alkyl group or a substituted or unsubstituted $C_6$-$C_{14}$ aryl group, and $M^+$ is a lithium, sodium, potassium, ammonium or tetramethylammonium ion.

When the sulfonate salt preparing method yields a mixture of such sulfonate salts, the molar ratio of the sulfonate salt of formula (1) to the sulfonate salt of formula (1') or (1") is often in a range from 100:0 to 100:10, although the exact ratio varies with the type of substituent group R and reaction conditions.

The sulfonate salt of formula (1') or (1") may be used alone or in admixture with the sulfonate salt of formula (1) to synthesize a photoacid generator, sulfonium salt, iodonium salt, N-sulfonyloxyimide compound or oxime sulfonate compound. The photoacid generator synthesized using the sulfonate salt of formula (1') or (1") may be included in resist compositions, especially chemically amplified positive resist compositions, or applied to a patterning process.

Specifically, still further embodiments of the invention include a photoacid generator for chemically amplified resist compositions which generates a sulfonic acid having the general formula (1'a) or (1"a) upon exposure to high-energy radiation selected from UV, deep-UV, electron beam, x-ray, excimer laser, gamma-ray and synchrotron radiation, $$CF_3-C(OCOR)=CFSO_3^- H^+ \quad (1'a)$$

$$CF_2=C(OCOR)CF_2SO_3^- H^+ \quad (1''a)$$

wherein R is as defined above;

a sulfonium salt having the general formula (2') or (2"):

$$R^1R^2R^3S^+ \; CF_3-C(OCOR)=CFSO_3^- \quad (2')$$

$$R^1R^2R^3S^+ \; CF_2=C(OCOR)CF_2SO_3^- \quad (2'')$$

wherein R is as defined above, $R^1$, $R^2$ and $R^3$ are each independently selected from among substituted or unsubstituted, straight or branched $C_1$-$C_{10}$ alkyl, alkenyl and oxoalkyl groups, and substituted or unsubstituted $C_6$-$C_{18}$ aryl, aralkyl and aryloxoalkyl groups, or any two or more of $R^1$, $R^2$ and $R^3$ may bond together to form a ring with the sulfur atom;

a sulfonium salt having the general formula (2'a) or (2"a):

$$R'-(O)_n-PhS^+Ph_2 \; CF_3-C(OCOR)=CFSO_3^- \quad (2'a)$$

$$R'-(O)_n-PhS^+Ph_2 \; CF_2=C(OCOR)CF_2SO_3^- \quad (2''a)$$

wherein R is as defined above, R' is a substituted or unsubstituted, straight, branched or cyclic $C_1$-$C_{20}$ alkyl or alkenyl group or a substituted or unsubstituted $C_6$-$C_{14}$ aryl group, Ph is phenyl, and n is 0 or 1;

a iodonium salt having the general formula (2'b) or (2"b):

$$R'(O)_n-PhI^+Ph(O)_n-R' \; CF_3-C(OCOR)=CFSO_3^- \quad (2'b)$$

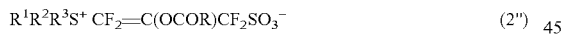
$$R'(O)_n-PhI^+Ph(O)_n-R' \; CF_2=C(OCOR)CF_2SO_3^- \quad (2''b)$$

wherein R, R', Ph and n are as defined above;

a N-sulfonyloxyimide compound having the general formula (3'a) or (3"a):

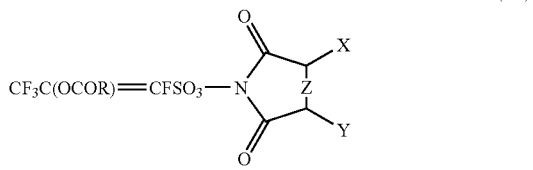

(3'a)

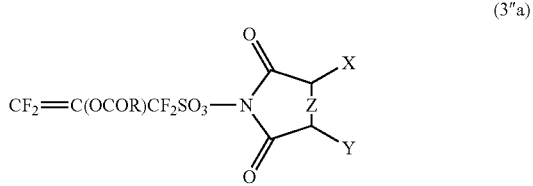

(3"a)

wherein R is as defined above, X and Y are each independently hydrogen or a substituted or unsubstituted $C_1$-$C_6$ alkyl group, or X and Y may bond together to form a saturated or unsaturated $C_6$-$C_{12}$ ring with the carbon atoms to which they are attached, and Z is a single bond, double bond, methylene group or oxygen atom; and an oxime sulfonate compound having the general formula (3'b) or (3"b):

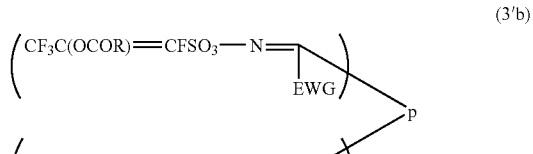

(3'b)

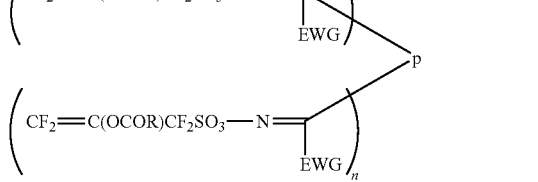

(3"b)

wherein R is as defined above, n is 0 or 1, when n is 0, p is a substituted or unsubstituted $C_1$-$C_{20}$ alkyl group or a substituted or unsubstituted $C_6$-$C_{12}$ aryl group, when n is 1, p is a substituted or unsubstituted $C_1$-$C_{20}$ alkylene group or a substituted or unsubstituted $C_6$-$C_{12}$ arylene group, EWG is a cyano, trifluoromethyl, perfluoroethyl, perfluoropropyl, 5H-perfluoropentyl, 6H-perfluorohexyl, nitro or methyl group, and when n is 1, two EWG's may bond together to form a ring of 6 carbon atoms with the carbon atoms to which they are attached.

The compounds of the still further embodiments serve as photoacid generators and may be included in resist compositions or applied to patterning processes in the same manner as the preceding embodiments of the invention.

It is understood that the sulfonate salts of formula (1') or (1") or homologues can be identified by analyzing a mixture thereof with a sulfonate salt of formula (1) by $^{19}$F-NMR spectroscopy as will be demonstrated in Synthesis Examples later. From the minute peaks of doublet near −66 ppm and quartet near −125 ppm which are observed in addition to the peaks of the major component, the presence of (1') type sulfonate anion is presumed. These chemical shifts are inherent to the example of PAG2 in FIG. 6 while chemical shifts differ with a particular compound, measuring solvent and measuring conditions. On time-of-flight mass spectrometry, aside from the major anion, an anion having a mass number smaller by 20 than the major anion is sometimes observed on the negative side as a minute peak although a chance of observation depends on an existence ratio and sensitivity.

In converting the sulfonate salts of formula (1) to the sulfonium and iodonium salts of formulae (2), (2a) and (2b), the reaction may be performed by a conventional anion exchange method. The sulfonium and iodonium salts can be synthesized in accordance with the teachings of The Chemistry of Sulfonium Group Part 1, 267-312, John-Wiley & Sons (1981), Advances in Photochemistry, Vol. 17, 313-320, John-Wiley & Sons (1992), J. Org. Chem., 53, 5571-5573, 1988, JP-A 8-311018, JP-A 9-15848, JP-A 2001-122850, JP-A 7-25846, JP-A 2001-181221, JP-A 2002-193887, and JP-A 2002-193925.

The onium cation having an acryloyloxy or methacryloyloxy group as the polymerizable substituent group can be synthesized by reacting (currently available) hydroxyphenyldiphenylsulfonium halide with acryloyl chloride or methacryloyl chloride under basic conditions according to the methods described in JP-A 4-230645 and JP-A 2005-84365.

Anion exchange may be performed in an alcohol solvent such as methanol or ethanol or a two-layer system of dichloromethane and water or the like. Alternatively, anion exchange may be performed by another recipe of reacting a corresponding methyl sulfonate with sulfonyl halide or iodonium halide, and removing the halide ion as methyl halide, as described in JP-A 2002-167340.

Also, the compounds of formula (3a) and (3b) can be synthesized by reacting the sulfonate salt with a chlorinating agent such as thionyl chloride, phosphorus oxychloride or phosphorus pentachloride to form a corresponding sulfonyl chloride or sulfonic acid anhydride, and further reacting with N-hydroxydicarboxylimide or oximes in a conventional way. For the synthesis of imide sulfonate or oxime sulfonate, reference should be made to the above-cited JP-A 2003-252855, U.S. Pat. No. 6,261,738, JP-A 9-95479, JP-A 9-208554, JP-A 9-230588, Japanese Patent No. 2,906,999, JP-A 9-301948, JP-A 2000-314956, JP-A 2001-233842, and International Publication 2004-074242.

As described above, a first embodiment of the present invention provides a sulfonate salt having formula (1). A second embodiment of the present invention provides a photoacid generator for chemically amplified resist compositions which generates a sulfonic acid having formula (1a) upon exposure to high-energy radiation. A third embodiment of the present invention provides a sulfonium salt, iodonium salt, dicarboxylimide sulfonate, and oxime sulfonate serving as photoacid generators in chemically amplified resist compositions. A fourth embodiment of the present invention provides a resist composition comprising a photoacid generator which generates a sulfonic acid having formula (1a) upon exposure to high-energy radiation and a resin which changes its solubility in an alkaline developer liquid under the action of acid.

The resist composition of the invention is typically embodied as (i) a chemically amplified positive resist composition comprising (A) a photoacid generator which generates a sulfonic acid having formula (1a) upon exposure to high-energy radiation,
(B) an organic solvent,
(C) a base resin which changes its solubility in an alkaline developer liquid under the action of acid, and one or more optional components including (D) a basic compound, (E) a photoacid generator other than (A), (F) an organic acid derivative and/or fluorinated alcohol, and (G) a dissolution inhibitor having a molecular weight of up to 3,000; and (ii) a chemically amplified negative resist composition comprising (A) a photoacid generator which generates a sulfonic acid having formula (1a) upon exposure to high-energy radiation,
(B) an organic solvent,
(C') a base resin which is normally alkali soluble, but becomes substantially alkali insoluble under the action of a crosslinker,
(H) a crosslinker which induces crosslinkage under the action of acid, and one or more optional components including (D) a basic compound and (E) a photoacid generator other than (A).

The PAG which generates a sulfonic acid having formula (1a) as component (A) is as described above. More specifically, it is a compound having formula (2), (2a), (2b), (3a) or (3b). In the resist composition, the PAG is compounded in an amount of 0.1 to 10 parts, more preferably 1 to 5 parts by weight per 100 parts by weight of the base resin.

Component B

The organic solvent used herein may be any organic solvent in which the base resin, photoacid generator, and other components are soluble. Illustrative, non-limiting, examples of the organic solvent include ketones such as cyclohexanone and methyl amyl ketone; alcohols such as 3-methoxybutanol, 3-methyl-3-methoxybutanol, 1-methoxy-2-propanol, and 1-ethoxy-2-propanol; ethers such as propylene glycol monomethyl ether, ethylene glycol monomethyl ether, propylene glycol monoethyl ether, ethylene glycol monoethyl ether, propylene glycol dimethyl ether, and diethylene glycol dimethyl ether; esters such as propylene glycol monomethyl ether acetate, propylene glycol monoethyl ether acetate, ethyl lactate, ethyl pyruvate, butyl acetate, methyl 3-methoxypropionate, ethyl 3-ethoxypropionate, tert-butyl acetate, tert-butyl propionate, and propylene glycol mono-tert-butyl ether acetate; and lactones such as γ-butyrolactone. These solvents may be used alone or in combinations of two or more thereof. Of the above organic solvents, it is recommended to use diethylene glycol dimethyl ether, 1-ethoxy-2-propanol, propylene glycol monomethyl ether acetate (PGMEA), cyclohexanone and mixtures thereof because the photoacid generator is most soluble therein.

An appropriate amount of the organic solvent used is about 200 to 3,000 parts, especially about 400 to 2,000 parts by weight per 100 parts by weight of the base resin.

Component C

The base resins used as component (C) or (C') in the inventive compositions include polyhydroxystyrene (PHS), and copolymers of PHS with styrene, (meth)acrylic acid esters or other polymerizable olefinic compounds, for KrF excimer laser resist use; (meth)acrylic acid ester polymers, alternating copolymers of cycloolefin with maleic anhydride, copolymers further containing vinyl ethers or (meth)acrylic acid esters, polynorbornene, ring-opening metathesis polymerized cycloolefins, and hydrogenated ring-opening metathesis polymerized cycloolefins, for ArF excimer laser resist use; and fluorinated forms of the foregoing polymers (for both KrF and ArF laser uses) for $F_2$ excimer laser resist use, although the base resins are not limited to these polymers.

Understandably, the sulfonium salts and iodonium salts having polymerizable substituent groups according to the invention may be used as a monomer component in forming the base resin. Typical sulfonium and iodonium salts for such use are combinations of onium cations such as 4-(acryloyloxy)phenyldiphenylsulfonium, 4-(methacryloyloxy)phenyldiphenylsulfonium, 4-(acryloyloxy)phenylphenyliodonium, and 4-(methacryloyloxy)phenylphenyliodonium cations with anions such as 1,1,3,3,3-pentafluoro-2-benzoyloxypropane-1-sulfonate, 1,1,3,3,3-pentafluoro-2-pivaloyloxypropane-1-sulfonate, and 1,1,3,3,3-pentafluoro-2-cyclohexanecarbonyloxypropane-1-sulfonate anions.

The base resins may be used alone or in admixture of two or more. In the case of positive resist compositions, it is a common practice to substitute acid labile groups for hydroxyl groups on phenol, carboxyl groups or fluorinated alkyl alcohols for reducing the rate of dissolution in unexposed regions.

The base resins are not limited to the foregoing resins. Use may also be made of the resins described in the following patents.

| | |
|---|---|
| JP-A 2000-159758 | JP-A 2000-186118 |
| JP-A 2000-309611 | JP-A 2000-327633 |
| JP-A 2000-330283 | JP-A 2001-329052 |
| JP-A 2002-202609 | JP-A 2002-161116 |
| JP-A 2003-2883 | JP-A 2003-20313 |
| JP-A 2003-26728 | JP-A 2003-34706 |
| JP-A 2003-64134 | JP-A 2003-66612 |
| JP-A 2003-113213 | JP-A 2003-316027 |
| JP-A 2003-321466 | JP-A 2004-143153 |
| JP-A 2004-124082 | JP-A 2004-115486 |
| JP-A 2004-62175 | |

In a preferred embodiment, the base resin is at least one polymer selected from among poly(meth)acrylic acid and derivatives thereof, alternating copolymers of a cycloolefin derivative and maleic anhydride, copolymers of three or more components comprising a cycloolefin derivative, maleic anhydride, and polyacrylic acid or derivatives thereof, cycloolefin derivative-α-trifluoromethyl acrylate copolymers, polynorbornene, ring-opening metathesis polymers, and hydrogenated ring-opening metathesis polymers.

In another preferred embodiment, the base resin is a polymeric structure containing silicon atoms or a polymeric structure containing fluorine atoms. Such polymers include those described in the following patents.

| | |
|---|---|
| JP-A 2005-8765 | JP-A 2004-354417 |
| JP-A 2004-352743 | JP-A 2004-331854 |
| JP-A 2004-331853 | JP-A 2004-292781 |
| JP-A 2004-252405 | JP-A 2004-190036 |
| JP-A 2004-115762 | JP-A 2004-83873 |
| JP-A 2004-59844 | JP-A 2004-35671 |
| JP-A 2004-83900 | JP-A 2004-99689 |
| JP-A 2004-145048 | JP-A 2004-217533 |
| JP-A 2004-231815 | JP-A 2004-244439 |
| JP-A 2004-256562 | JP-A 2004-307447 |
| JP-A 2004-323422 | JP-A 2005-29527 |
| JP-A 2005-29539 | |

Included in the chemically amplified positive resist composition is a base resin having acid labile groups which is normally insoluble or substantially insoluble in developer, but becomes soluble in developer as a result of the acid labile groups being eliminated under the action of acid.

The acid labile groups to be introduced into the base resin may be selected from a variety of such groups, preferably from $C_2$-$C_{30}$ acetal groups and tertiary $C_4$-$C_{30}$ alkyl groups having the formulae (C1) and (C2), respectively.

In formulae (C1) and (C2), $R^4$ and $R^5$ each are hydrogen or a straight, branched or cyclic $C_1$-$C_{20}$ alkyl group, which may contain a hetero atom such as oxygen, sulfur, nitrogen or fluorine, $R^6$, $R^7$, $R^8$ and $R^9$ each are a straight, branched or cyclic $C_1$-$C_{20}$ alkyl group, a $C_6$-$C_{10}$ aryl group or a $C_7$-$C_{11}$ aralkyl group, which may contain a hetero atom such as oxygen, sulfur, nitrogen or fluorine. A pair of $R^4$ and $R^5$, a pair of $R^4$ and $R^6$, a pair of $R^5$ and $R^6$, a pair of $R^7$ and $R^8$, a pair of $R^7$ and $R^9$, or a pair of $R^8$ and $R^9$, taken together, may form a ring of 3 to 30 carbon atoms with the carbon atom to which they are attached.

Illustrative examples of the acetal group of formula (C1) include, but are not limited to, methoxymethyl, ethoxymethyl, propoxymethyl, butoxymethyl, isopropoxymethyl, t-butoxymethyl, 1-methoxyethyl, 1-methoxypropyl, 1-methoxybutyl, 1-ethoxyethyl, 1-ethoxypropyl, 1-ethoxybutyl, 1-propoxyethyl, 1-propoxypropyl, 1-propoxybutyl, 1-cyclopentyloxyethyl, 1-cyclohexyloxyethyl, 2-methoxyisopropyl, 2-ethoxyisopropyl, 1-phenoxyethyl, 1-benzyloxyethyl, 1-phenoxypropyl, 1-benzyloxypropyl, 1-adamantyloxyethyl, 1-adamantyloxypropyl, 2-tetrahydrofuryl, 2-tetrahydro-2H-pyranyl, 1-(2-cyclohexanecarbonyloxyethoxy)ethyl, 1-(2-cyclohexanecarbonyloxyethoxy)propyl, 1-[2-(1-adamantylcarbonyloxy)ethoxy]ethyl, and 1-[2-(1-adamantylcarbonyloxy)ethoxy]propyl.

Illustrative examples of the tertiary alkyl group of formula (C2) include, but are not limited to, t-butyl, t-pentyl, 1-ethyl-1-methylpropyl, 1,1-diethylpropyl, 1,1,2-trimethylpropyl, 1-adamantyl-1-methylethyl, 1-methyl-1-(2-norbornyl)ethyl, 1-methyl-1-(tetrahydrofuran-2-yl)ethyl, 1-methyl-1-(7-oxanorbornan-2-yl)ethyl, 1-methylcyclopentyl, 1-ethylcyclopentyl, 1-propylcyclopentyl, 1-cyclopentylcyclopentyl, 1-cyclohexylcyclopentyl, 1-(2-tetrahydrofuryl)cyclopentyl, 1-(7-oxanorbornan-2-yl)cyclopentyl, 1-methylcyclohexyl, 1-ethylcyclohexyl, 1-cyclopentylcyclohexyl, 1-cyclohexylcyclohexyl, 2-methyl-2-norbornyl, 2-ethyl-2-norbornyl, 8-methyl-8-tricyclo[5.2.1.0$^{2,6}$]decyl, 8-ethyl-8-tricyclo[5.2.1.0$^{2,6}$]decyl, 3-methyl-3-tetracyclo[4.4.0.1$^{2,5}$.1$^{7,10}$]dodecyl, 3-ethyl-3-tetracyclo[4.4.0.1$^{2,5}$.1$^{7,0}$]dodecyl, 2-methyl-2-adamantyl, 2-ethyl-2-adamantyl, 1-methyl-3-oxo-1-cyclohexyl, 1-methyl-1-(tetrahydrofuran-2-yl)ethyl, 5-hydroxy-2-methyl-2-adamantyl, and 5-hydroxy-2-ethyl-2-adamantyl.

In the base resin, at least 1 mol % of hydrogen atoms of hydroxyl groups may be substituted by acid labile groups of the following general formula (C3a) or (C3b) for crosslinkage between molecules or within a molecule.

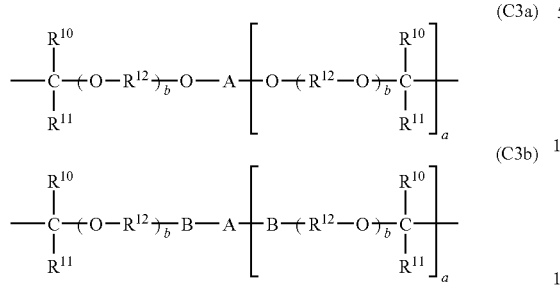

Herein, $R^{10}$ and $R^{11}$ each are hydrogen or a straight, branched or cyclic alkyl group of 1 to 8 carbon atoms, or $R^{10}$ and $R^{11}$, taken together, may form a ring, with the proviso that each of $R^{10}$ and $R^{11}$ is a straight or branched alkylene group of 1 to 8 carbon atoms when they form a ring. $R^{12}$ is a straight, branched or cyclic alkylene group of 1 to 10 carbon atoms. Letter "a" is an integer of 1 to 7 and "b" is 0 or an integer of 1 to 10. "A" is a (a+1)-valent aliphatic or alicyclic saturated hydrocarbon group, aromatic hydrocarbon group or heterocyclic group of 1 to 50 carbon atoms, which may have an intervening hetero atom and in which the hydrogen atom attached to a carbon atom may be partially replaced by a hydroxyl group, carboxyl group, carbonyl group or fluorine atom. B is —CO—O—, —NHCO—O— or —NHCONH—.

Illustrative examples of the crosslinking acetal linkages represented by formulae (C3a) and (C3b) are given below as (C3)-1 through (C3)-8, but not limited thereto.

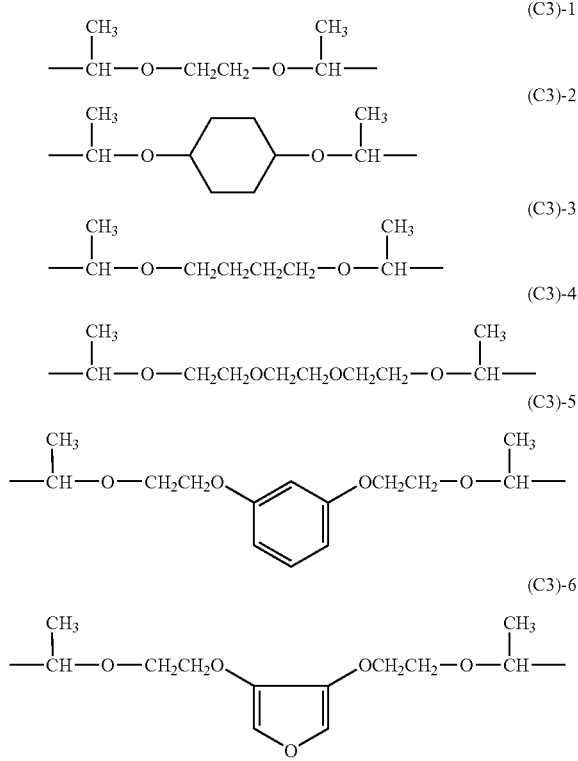

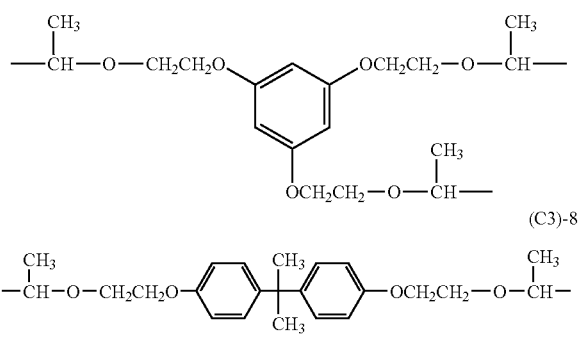

Preferably the base resin has a weight average molecular weight (Mw) of 2,000 to 100,000, as measured by gel permeation chromatography (GPC) versus polystyrene standards. With Mw below 2,000, film formation and resolution may become poor. With Mw beyond 100,000, resolution may become poor or foreign matter may generate during pattern formation.

In the base resin, the proportion of acid labile group-containing monomer units relative to the other monomer units (constituent units) is typically in a range of 10 to 70%, preferably 20 to 60%, in case intended for ArF excimer laser resist compositions; and typically in a range of 10 to 50%, preferably 20 to 40%, in case intended for KrF excimer laser resist compositions.

The monomer units other than the acid labile group-containing monomer units are preferably monomer units containing polar groups such as alcohols, fluorinated alcohols, and ether, lactone, ester, acid anhydride, and carboxylic acid in the case of the base resins for ArF excimer laser resist compositions. The base resins for KrF excimer laser resist compositions may comprise units of styrene, indene and 4-acetoxystyrene in addition to 4-hydroxystyrene units having no acid labile groups incorporated. These monomer units may be of one type or of two or more different types.

Component D

The basic compound used as component (D) is preferably a compound capable of suppressing the rate of diffusion when the acid generated by the photoacid generator diffuses within the resist film. The inclusion of this type of basic compound holds down the rate of acid diffusion within the resist film, resulting in better resolution. In addition, it suppresses changes in sensitivity following exposure and reduces substrate and environment dependence, as well as improving the exposure latitude and the pattern profile.

Examples of basic compounds include primary, secondary, and tertiary aliphatic amines, mixed amines, aromatic amines, heterocyclic amines, nitrogen-containing compounds with carboxyl group, nitrogen-containing compounds with sulfonyl group, nitrogen-containing compounds with hydroxyl group, nitrogen-containing compounds with hydroxyphenyl group, alcoholic nitrogen-containing compounds, amide derivatives, and imide derivatives.

Examples of suitable primary aliphatic amines include ammonia, methylamine, ethylamine, n-propylamine, isopropylamine, n-butylamine, isobutylamine, sec-butylamine, tert-butylamine, pentylamine, tert-amylamine, cyclopentylamine, hexylamine, cyclohexylamine, heptylamine, octylamine, nonylamine, decylamine, dodecylamine, cetylamine, methylenediamine, ethylenediamine, and tetraethylenepentamine. Examples of suitable secondary aliphatic amines include dimethylamine, diethylamine, di-n-propylamine, diisopropylamine, di-n-butylamine, diisobutylamine, di-sec-butylamine, dipentylamine, dicyclopentylamine, dihexylamine, dicyclohexylamine, diheptylamine, dioctylamine, dinonylamine, didecylamine, didodecylamine, dicetylamine, N,N-dimethylmethylenediamine, N,N-dimethylethylenediamine, and N,N-dimethyltetraethylenepentamine. Examples of suitable tertiary aliphatic amines include trimethylamine, triethylamine, tri-n-propylamine, triisopropylamine, tri-n-butylamine, triisobutylamine, tri-sec-butylamine, tripentylamine, tricyclopentylamine, trihexylamine, tricyclohexylamine, triheptylamine, trioctylamine, trinonylamine, tridecylamine, tridodecylamine, tricetylamine, N,N,N',N'-tetramethylmethylenediamine, N,N,N',N'-tetramethylethylenediamine, and N,N,N',N'-tetramethyltetraethylenepentamine.

Examples of suitable mixed amines include dimethylethylamine, methylethylpropylamine, benzylamine, phenethylamine, and benzyldimethylamine. Examples of suitable aromatic and heterocyclic amines include aniline derivatives (e.g., aniline, N-methylaniline, N-ethylaniline, N-propylaniline, N,N-dimethylaniline, 2-methylaniline, 3-methylaniline, 4-methylaniline, ethylaniline, propylaniline, trimethylaniline, 2-nitroaniline, 3-nitroaniline, 4-nitroaniline, 2,4-dinitroaniline, 2,6-dinitroaniline, 3,5-dinitroaniline, and N,N-dimethyltoluidine), diphenyl(p-tolyl)amine, methyldiphenylamine, triphenylamine, phenylenediamine, naphthylamine, diaminonaphthalene, pyrrole derivatives (e.g., pyrrole, 2H-pyrrole, 1-methylpyrrole, 2,4-dimethylpyrrole, 2,5-dimethylpyrrole, and N-methylpyrrole), oxazole derivatives (e.g., oxazole and isooxazole), thiazole derivatives (e.g., thiazole and isothiazole), imidazole derivatives (e.g., imidazole, 4-methylimidazole, and 4-methyl-2-phenylimidazole), pyrazole derivatives, furazan derivatives, pyrroline derivatives (e.g., pyrroline and 2-methyl-1-pyrroline), pyrrolidine derivatives (e.g., pyrrolidine, N-methylpyrrolidine, pyrrolidinone, and N-methylpyrrolidone), imidazoline derivatives, imidazolidine derivatives, pyridine derivatives (e.g., pyridine, methylpyridine, ethylpyridine, propylpyridine, butylpyridine, 4-(1-butylpentyl)pyridine, dimethylpyridine, trimethylpyridine, triethylpyridine, phenylpyridine, 3-methyl-2-phenylpyridine, 4-tert-butylpyridine, diphenylpyridine, benzylpyridine, methoxypyridine, butoxypyridine, dimethoxypyridine, 1-methyl-2-pyridine, 4-pyrrolidinopyridine, 1-methyl-4-phenylpyridine, 2-(1-ethylpropyl)pyridine, aminopyridine, and dimethylaminopyridine), pyridazine derivatives, pyrimidine derivatives, pyrazine derivatives, pyrazoline derivatives, pyrazolidine derivatives, piperidine derivatives, piperazine derivatives, morpholine derivatives, indole derivatives, isoindole derivatives, 1H-indazole derivatives, indoline derivatives, quinoline derivatives (e.g., quinoline and 3-quinolinecarbonitrile), isoquinoline derivatives, cinnoline derivatives, quinazoline derivatives, quinoxaline derivatives, phthalazine derivatives, purine derivatives, pteridine derivatives, carbazole derivatives, phenanthridine derivatives, acridine derivatives, phenazine derivatives, 1,10-phenanthroline derivatives, adenine derivatives, adenosine derivatives, guanine derivatives, guanosine derivatives, uracil derivatives, and uridine derivatives.

Examples of suitable nitrogen-containing compounds with carboxyl group include aminobenzoic acid, indolecarboxylic acid, and amino acid derivatives (e.g. nicotinic acid, alanine, alginine, aspartic acid, glutamic acid, glycine, histidine, isoleucine, glycylleucine, leucine, methionine, phenylalanine, threonine, lysine, 3-aminopyrazine-2-carboxylic acid, and methoxyalanine). Examples of suitable nitrogen-containing compounds with sulfonyl group include 3-pyridinesulfonic acid and pyridinium p-toluenesulfonate. Examples of suitable nitrogen-containing compounds with hydroxyl group, nitrogen-containing compounds with hydroxyphenyl group, and alcoholic nitrogen-containing compounds include 2-hydroxypyridine, aminocresol, 2,4-quinolinediol, 3-indolemethanol hydrate, monoethanolamine, diethanolamine, triethanolamine, N-ethyldiethanolamine, N,N-diethylethanolamine, triisopropanolamine, 2,2'-iminodiethanol, 2-aminoethanol, 3-amino-1-propanol, 4-amino-1-butanol, 4-(2-hydroxyethyl)morpholine, 2-(2-hydroxyethyl)pyridine, 1-(2-hydroxyethyl)piperazine, 1-[2-(2-hydroxyethoxy)ethyl]piperazine, piperidine ethanol, 1-(2-hydroxyethyl)pyrrolidine, 1-(2-hydroxyethyl)-2-pyrrolidinone, 3-piperidino-1,2-propanediol, 3-pyrrolidino-1,2-propanediol, 8-hydroxyjulolidine, 3-quinuclidinol, 3-tropanol, 1-methyl-2-pyrrolidine ethanol, 1-aziridine ethanol, N-(2-hydroxyethyl)phthalimide, and N-(2-hydroxyethyl)isonicotinamide. Examples of suitable amide derivatives include formamide, N-methylformamide, N,N-dimethylformamide, acetamide, N-methylacetamide, N,N-dimethylacetamide, propionamide, and benzamide. Suitable imide derivatives include phthalimide, succinimide, and maleimide.

In addition, basic compounds of the following general formula (B)-1 may also be included alone or in admixture.

$N(X')_{n'}(Y')_{3-n'}$        (B)-1

In the formula, n' is equal to 1, 2 or 3; the side chain Y' is independently hydrogen or a straight, branched or cyclic $C_1$-$C_{20}$ alkyl group which may contain a hydroxyl or ether group; and the side chain X' is independently selected from groups of the following general formulas (X')-1 to (X')-3, and two or three X' may bond together to form a ring.

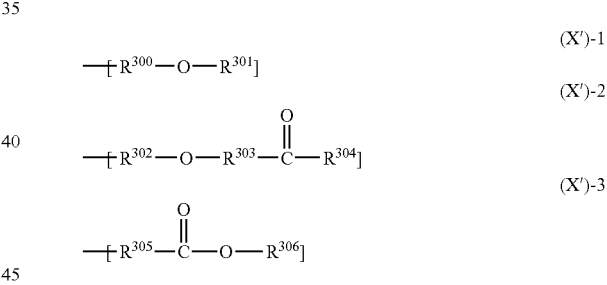

In the formulas, $R^{300}$, $R^{302}$ and $R^{305}$ are independently straight or branched $C_1$-$C_4$ alkylene groups; $R^{301}$ and $R^{304}$ are independently hydrogen or straight, branched or cyclic $C_1$-$C_{20}$ alkyl groups, which may contain at least one hydroxyl group, ether group, ester group or lactone ring; $R^{303}$ is a single bond or a straight or branched $C_1$-$C_4$ alkylene group; $R^{306}$ is a straight, branched or cyclic $C_1$-$C_{20}$ alkyl group, which may contain at least one hydroxyl group, ether group, ester group or lactone ring.

Illustrative examples of the basic compounds of formula (B)-1 include tris(2-methoxymethoxyethyl)amine, tris{2-(2-methoxyethoxy)ethyl}amine, tris{2-(2-methoxyethoxymethoxy)ethyl}amine, tris{2-(1-methoxyethoxy)ethyl}amine, tris{2-(1-ethoxyethoxy)ethyl}amine, tris{2-(1-ethoxypropoxy)ethyl}amine, tris[2-{2-(2-hydroxyethoxy)ethoxy}ethyl]amine, 4,7,13,16,21,24-hexaoxa-1,10-diazabicyclo[8.8.8]hexacosane, 4,7,13,18-tetraoxa-1,10-diazabicyclo[8.5.5]eicosane, 1,4,10,13-tetraoxa-7,16-diazabicyclooctadecane, 1-aza-12-crown-4,1-aza-15-crown-5,1-aza-18-crown-6, tris(2-formyloxyethyl)amine, tris(2-acetoxyethyl)amine, tris(2-propionyloxyethyl)amine, tris(2- butyryloxyethyl)amine, tris(2-isobutyryloxyethyl)amine, tris (2-valeryloxyethyl)amine, tris(2-pivaloyloxyethyl)amine, N,N-bis(2-acetoxyethyl)-2-(acetoxyacetoxy)ethylamine, tris (2-methoxycarbonyloxyethyl)amine, tris(2-tert-butoxycarbonyloxyethyl)amine, tris[2-(2-oxopropoxy)ethyl]amine, tris[2-(methoxycarbonylmethyl)oxyethyl]amine, tris[2-(tert-butoxycarbonylmethyloxy)ethyl]amine, tris[2-(cyclohexyloxycarbonylmethyloxy)ethyl]amine, tris(2-methoxycarbonylethyl)amine, tris(2-ethoxycarbonylethyl)amine, N,N-bis (2-hydroxyethyl)-2-(methoxycarbonyl)ethylamine, N,N-bis (2-acetoxyethyl)-2-(methoxycarbonyl)ethylamine, N,N-bis (2-hydroxyethyl)-2-(ethoxycarbonyl)ethylamine, N,N-bis (2-acetoxyethyl)-2-(ethoxycarbonyl)ethylamine, N,N-bis(2-hydroxyethyl)-2-(2-methoxyethoxycarbonyl)ethylamine, N,N-bis(2-acetoxyethyl)-2-(2-methoxyethoxycarbonyl) ethylamine, N,N-bis(2-hydroxyethyl)-2-(2-hydroxyethoxycarbonyl)ethylamine, N,N-bis(2-acetoxyethyl)-2-(2-acetoxyethoxycarbonyl)ethylamine, N,N-bis(2-hydroxyethyl)-2-[(methoxycarbonyl)methoxycarbonyl]-ethylamine, N,N-bis(2-acetoxyethyl)-2-[(methoxycarbonyl)methoxycarbonyl]-ethylamine, N,N-bis(2-hydroxyethyl)-2-(2-oxopropoxycarbonyl)ethylamine, N,N-bis(2-acetoxyethyl)-2-(2-oxopropoxycarbonyl)ethylamine, N,N-bis(2-hydroxyethyl)-2-(tetrahydrofurfuryloxycarbonyl)-ethylamine, N,N-bis(2-acetoxyethyl)-2-(tetrahydrofurfuryloxycarbonyl)-ethylamine, N,N-bis(2-hydroxyethyl)-2-[(2-oxotetrahydrofuran-3-yl)oxy-carbonyl]ethylamine, N,N-bis(2-acetoxyethyl)-2-[(2-oxotetrahydrofuran-3-yl)oxy-carbonyl]ethylamine, N,N-bis (2-hydroxyethyl)-2-(4-hydroxybutoxycarbonyl)ethylamine, N,N-bis(2-formyloxyethyl)-2-(4-formyloxybutoxycarbonyl)-ethylamine, N,N-bis(2-formyloxyethyl)-2-(2-formyloxyethoxycarbonyl)-ethylamine, N,N-bis(2-methoxyethyl)-2-(methoxycarbonyl)ethylamine, N-(2-hydroxyethyl)-bis[2-(methoxycarbonyl)ethyl]amine, N-(2-acetoxyethyl)-bis[2-(methoxycarbonyl)ethyl]amine, N-(2-hydroxyethyl)-bis[2-(ethoxycarbonyl)ethyl]amine, N-(2-acetoxyethyl)-bis[2-(ethoxycarbonyl)ethyl]amine, N-(3-hydroxy-1-propyl)-bis[2-(methoxycarbonyl)ethyl]amine, N-(3-acetoxy-1-propyl)-bis[2-(methoxycarbonyl)ethyl] amine, N-(2-methoxyethyl)-bis[2-(methoxycarbonyl)ethyl] amine, N-butyl-bis[2-(methoxycarbonyl)ethyl]amine, N-butyl-bis[2-(2-methoxyethoxycarbonyl)ethyl]amine, N-methyl-bis(2-acetoxyethyl)amine, N-ethyl-bis(2-acetoxyethyl)amine, N-methyl-bis(2-pivaloyloxyethyl)amine, N-ethyl-bis[2-(methoxycarbonyloxy)ethyl]amine, N-ethyl-bis[2-(tert-butoxycarbonyloxy)ethyl]amine, tris(methoxycarbonylmethyl)amine, tris(ethoxycarbonylmethyl)amine, N-butyl-bis(methoxycarbonylmethyl)amine, N-hexyl-bis (methoxycarbonylmethyl)amine, and β-(diethylamino)-δ-valerolactone.

Also useful are one or more of cyclic structure-bearing basic compounds having the following general formula (B)-2.

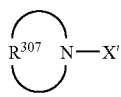
(B)-2

Herein X' is as defined above, and $R^{307}$ is a straight or branched $C_2$-$C_{20}$ alkylene group which may contain one or more carbonyl, ether, ester or sulfide groups.

Illustrative examples of the cyclic structure-bearing basic compounds having formula (B)-2 include 1-[2-(methoxymethoxy)ethyl]pyrrolidine, 1-[2-(methoxymethoxy) ethyl]piperidine, 4-[2-(methoxymethoxy)ethyl]morpholine, 1-[2-[(2-methoxyethoxy)methoxy]ethyl]pyrrolidine, 1-[2-[(2-methoxyethoxy)methoxy]ethyl]piperidine, 4-[2-[(2-methoxyethoxy)methoxy]ethyl]morpholine, 2-(1-pyrrolidinyl)ethyl acetate, 2-piperidinoethyl acetate, 2-morpholinoethyl acetate, 2-(1-pyrrolidinyl)ethyl formate, 2-piperidinoethyl propionate, 2-morpholinoethyl acetoxyacetate, 2-(1-pyrrolidinyl)ethyl methoxyacetate, 4-[2-(methoxycarbonyloxy)ethyl]morpholine, 1-[2-(t-butoxycarbonyloxy)ethyl]piperidine, 4-[2-(2-methoxyethoxycarbonyloxy) ethyl]morpholine, methyl 3-(1-pyrrolidinyl)propionate, methyl 3-piperidinopropionate, methyl 3-morpholinopropionate, methyl 3-(thiomorpholino)propionate, methyl 2-methyl-3-(1-pyrrolidinyl)propionate, ethyl 3-morpholinopropionate, methoxycarbonylmethyl 3-piperidinopropionate, 2-hydroxyethyl 3-(1-pyrrolidinyl)propionate, 2-acetoxyethyl 3-morpholinopropionate, 2-oxotetrahydrofuran-3-yl 3-(1-pyrrolidinyl)propionate, tetrahydrofurfuryl 3-morpholinopropionate, glycidyl 3-piperidinopropionate, 2-methoxyethyl 3-morpholinopropionate, 2-(2-methoxyethoxy)ethyl 3-(1-pyrrolidinyl)propionate, butyl 3-morpholinopropionate, cyclohexyl 3-piperidinopropionate, α-(1-pyrrolidinyl)methyl-γ-butyrolactone, β-piperidino-γ-butyrolactone, β-morpholino-δ-valerolactone, methyl 1-pyrrolidinylacetate, methyl piperidinoacetate, methyl morpholinoacetate, methyl thiomorpholinoacetate, ethyl 1-pyrrolidinylacetate, and 2-methoxyethyl morpholinoacetate.

Also, one or more of cyano-bearing basic compounds having the following general formulae (B)-3 to (B)-6 may be blended.

(B)-3

(B)-4

(B)-5

(B)-6

Herein, X', $R^{307}$ and n' are as defined above, and $R^{308}$ and $R^{309}$ each are independently a straight or branched $C_1$-$C_4$ alkylene group.

Illustrative examples of the cyano-bearing basic compounds having formulae (B)-3 to (B)-6 include 3-(diethylamino)propiononitrile, N,N-bis(2-hydroxyethyl)-3-aminopropiononitrile, N,N-bis(2-acetoxyethyl)-3-aminopropiononitrile, N,N-bis(2-formyloxyethyl)-3-aminopropiononitrile, N,N-bis(2-methoxyethyl)-3-aminopropiononitrile, N,N-bis[2-(methoxymethoxy)ethyl]-3-aminopropiononitrile, methyl N-(2-cyanoethyl)-N-(2-methoxyethyl)-3-aminopropionate, methyl N-(2-cyanoethyl)-N-(2-hydroxyethyl)-3-aminopropionate, methyl N-(2-acetoxyethyl)-N-(2-cyanoethyl)-3-aminopropionate, N-(2-cyanoethyl)-N-ethyl-3-aminopropiononitrile, N-(2-cyanoethyl)-N-(2-hydroxyethyl)-3-aminopropiononitrile, N-(2-acetoxyethyl)-N-(2-cyanoethyl)-3-aminopropiononitrile, N-(2-cyanoethyl)-N-(2-formyloxyethyl)-3-aminopropiononitrile, N-(2-cyanoethyl)-N-(2-methoxyethyl)-3-aminopropionitrile, N-(2-cyanoethyl)-N-[2-(methoxymethoxy)ethyl]-3-aminopropiono-nitrile, N-(2-cyanoethyl)-N-(3-hydroxy-1-propyl)-3-aminopropiononitrile, N-(3-acetoxy-1-propyl)-N-(2-cyanoethyl)-3-aminopropiononitrile, N-(2-cyanoethyl)-N-(3-formyloxy-1-propyl)-3-aminopropiono-nitrile, N-(2-cyanoethyl)-N-tetrahydrofurfuryl-3-aminopropiononitrile, N,N-bis(2-cyanoethyl)-3-aminopropiononitrile, diethylaminoacetonitrile, N,N-bis(2-hydroxyethyl)aminoacetonitrile, N,N-bis(2-acetoxyethyl)aminoacetonitrile, N,N-bis(2-formyloxyethyl)aminoacetonitrile, N,N-bis(2-methoxyethyl)aminoacetonitrile, N,N-bis[2-(methoxymethoxy)ethyl]aminoacetonitrile, methyl N-cyanomethyl-N-(2-methoxyethyl)-3-aminopropionate, methyl N-cyanomethyl-N-(2-hydroxyethyl)-3-aminopropionate, methyl N-(2-acetoxyethyl)-N-cyanomethyl-3-aminopropionate, N-cyanomethyl-N-(2-hydroxyethyl)aminoacetonitrile, N-(2-acetoxyethyl)-N-(cyanomethyl)aminoacetonitrile, N-cyanomethyl-N-(2-formyloxyethyl)aminoacetonitrile, N-cyanomethyl-N-(2-methoxyethyl)aminoacetonitrile, N-cyanomethyl-N-[2-(methoxymethoxy)ethyl]aminoacetonitrile, N-cyanomethyl-N-(3-hydroxy-1-propyl)aminoacetonitrile, N-(3-acetoxy-1-propyl)-N-(cyanomethyl)aminoacetonitrile, N-cyanomethyl-N-(3-formyloxy-1-propyl)aminoacetonitrile, N,N-bis(cyanomethyl)aminoacetonitrile, 1-pyrrolidinepropiononitrile, 1-piperidinepropiononitrile, 4-morpholinepropiononitrile, 1-pyrrolidineacetonitrile, 1-piperidineacetonitrile, 4-morpholineacetonitrile, cyanomethyl 3-diethylaminopropionate, cyanomethyl N,N-bis(2-hydroxyethyl)-3-aminopropionate, cyanomethyl N,N-bis(2-acetoxyethyl)-3-aminopropionate, cyanomethyl N,N-bis(2-formyloxyethyl)-3-aminopropionate, cyanomethyl N,N-bis(2-methoxyethyl)-3-aminopropionate, cyanomethyl N,N-bis[2-(methoxymethoxy)ethyl]-3-aminopropionate, 2-cyanoethyl 3-diethylaminopropionate, 2-cyanoethyl N,N-bis(2-hydroxyethyl)-3-aminopropionate, 2-cyanoethyl N,N-bis(2-acetoxyethyl)-3-aminopropionate, 2-cyanoethyl N,N-bis(2-formyloxyethyl)-3-aminopropionate, 2-cyanoethyl N,N-bis(2-methoxyethyl)-3-aminopropionate, 2-cyanoethyl N,N-bis[2-(methoxymethoxy)ethyl]-3-aminopropionate, cyanomethyl 1-pyrrolidinepropionate, cyanomethyl 1-piperidinepropionate, cyanomethyl 4-morpholinepropionate, 2-cyanoethyl 1-pyrrolidinepropionate, 2-cyanoethyl 1-piperidinepropionate, and 2-cyanoethyl 4-morpholinepropionate.

Also included are basic compounds as described in JP-A 2004-347736 and JP-A 2004-347738.

The basic compounds may be used alone or in admixture of two or more. The basic compound is preferably formulated in an amount of 0 to 2 parts, and especially 0 to 1 part by weight, per 100 parts by weight of the base resin.

Component E

In one preferred embodiment, the resist composition further contains (E) a compound capable of generating an acid upon exposure to high-energy radiation (e.g., UV, deep UV, electron beam, x-ray, excimer laser beam, gamma-ray or synchrotron radiation), that is, an auxiliary photoacid generator other than component (A). Suitable auxiliary photoacid generators include sulfonium salts, iodonium salts, sulfonyldiazomethane, N-sulfonyloxydicarboxyimide, O-arylsulfonyloxime and O-alkylsulfonyloxime photoacid generators. Exemplary auxiliary photoacid generators are given below while they may be used alone or in admixture of two or more.

Sulfonium salts are salts of sulfonium cations with sulfonates, bis(substituted alkylsulfonyl)imides and tris(substituted alkylsulfonyl)methides. Exemplary sulfonium cations include triphenylsulfonium, (4-tert-butoxyphenyl)diphenylsulfonium, bis(4-tert-butoxyphenyl)phenylsulfonium, tris(4-tert-butoxyphenyl)sulfonium, (3-tert-butoxyphenyl)diphenylsulfonium, bis(3-tert-butoxyphenyl)phenylsulfonium, tris(3-tert-butoxyphenyl)sulfonium, (3,4-di-tert-butoxyphenyl)diphenylsulfonium, bis(3,4-di-tert-butoxyphenyl)phenylsulfonium, tris(3,4-di-tert-butoxyphenyl)sulfonium, diphenyl(4-thiophenoxyphenyl)sulfonium, (4-tert-butoxycarbonylmethyloxyphenyl)diphenylsulfonium, tris(4-tert-butoxycarbonylmethyloxyphenyl)sulfonium, (4-tert-butoxyphenyl)bis(4-dimethylaminophenyl)sulfonium, tris(4-dimethylaminophenyl)sulfonium, 4-methylphenyldiphenylsulfonium, 4-tert-butylphenyldiphenylsulfonium, bis(4-methylphenyl)phenylsulfonium, bis(4-tert-butylphenyl)phenylsulfonium, tris(4-methylphenyl)sulfonium, tris(4-tert-butylphenyl)sulfonium, tris(phenylmethyl)sulfonium, 2-naphthyldiphenylsulfonium, dimethyl-2-naphthylsulfonium, 4-hydroxyphenyldimethylsulfonium, 4-methoxyphenyldimethylsulfonium, trimethylsulfonium, 2-oxocyclohexylcyclohexylmethylsulfonium, trinaphthylsulfonium, tribenzylsulfonium, diphenylmethylsulfonium, dimethylphenylsulfonium, 2-oxopropylthiacyclopentanium, 2-oxobutylthiacyclopentanium, 2-oxo-3,3-dimethylbutylthiacyclopentanium, 2-oxo-2-phenylethylthiacyclopentanium, 4-n-butoxynaphthyl-1-thiacyclopentanium, and 2-n-butoxynaphthyl-1-thiacyclopentanium. Exemplary sulfonates include trifluoromethanesulfonate, pentafluoroethanesulfonate, heptafluoropropanesulfonate, nonafluorobutanesulfonate, dodecafluorohexanesulfonate, pentafluoroethylperfluorocyclohexanesulfonate, heptadecafluorooctanesulfonate, perfluoro-4-ethylcyclohexanesulfonate, 2,2,2-trifluoroethanesulfonate, pentafluorobenzenesulfonate, 4-trifluoromethylbenzenesulfonate, 4-fluorobenzenesulfonate, mesitylenesulfonate, 2,4,6-triisopropylbenzenesulfonate, toluenesulfonate, benzenesulfonate, 4-(4'-toluenesulfonyloxy)benzenesulfonate, 6-(4-toluenesulfonyloxy)naphthalene-2-sulfonate, 4-(4-toluenesulfonyloxy)naphthalene-1-sulfonate, 5-(4-toluenesulfonyloxy)naphthalene-1-sulfonate, 8-(4-toluenesulfonyloxy)naphthalene-1-sulfonate, naphthalenesulfonate, camphorsulfonate, octanesulfonate, dodecylbenzenesulfonate, butanesulfonate, methanesulfonate, 1,1-difluoro-2-naphthyl-ethanesulfonate, 1,1,2,2-tetrafluoro-2-(norbornan-2-yl)ethanesulfonate, and 1,1,2,2-tetrafluoro-2-(tetracyclo[4.4.0.1$^{2,5}$.1$^{7,10}$]dodec-3-en-8-yl)ethanesulfonate. Exemplary bis(substituted alkylsulfonyl)imides include bistrifluoromethylsulfonylimide, bispentafluoroethylsulfonylimide, bisheptafluoropropylsulfonylimide, and 1,3-propylenebissulfonylimide. A typical tris(substituted alkylsulfonyl)methide is tristrifluoromethylsulfonylmethide. Sulfonium salts based on combination of the foregoing examples are included.

Iodonium salts are salts of iodonium cations with sulfonates, bis(substituted alkylsulfonyl)imides and tris(substituted alkylsulfonyl)methides. Exemplary iodonium cations are aryliodonium cations including diphenyliodinium, bis(4-tert-butylphenyl)iodonium, 4-tert-butoxyphenylphenyliodonium, and 4-methoxyphenylphenyliodonium. Exemplary sulfonates include trifluoromethanesulfonate, pentafluoroethanesulfonate, heptafluoropropanesulfonate, nonafluorobutanesulfonate, dodecafluorohexanesulfonate, pentafluoroethylperfluorocyclohexanesulfonate, heptadecafluorooctanesulfonate, perfluoro-4-ethylcyclohexanesulfonate, 2,2,2-trifluoroethanesulfonate, pentafluorobenzenesulfonate, 4-trifluoromethylbenzenesulfonate, 4-fluorobenzenesulfonate, mesitylenesulfonate, 2,4,6-triisopropylbenzenesulfonate, toluenesulfonate, benzenesulfonate, 4-(4'-toluenesulfonyloxy)benzenesulfonate, 6-(4-toluenesulfonyloxy)naphthalene-2-sulfonate, 4-(4-toluenesulfonyloxy)naphthalene-1-sulfonate, 5-(4-toluenesulfonyloxy)naphthalene-1-sulfonate, 8-(4-toluenesulfonyloxy)naphthalene-1-sulfonate, naphthalenesulfonate, camphorsulfonate, octanesulfonate, dodecylbenzenesulfonate, butanesulfonate, methanesulfonate, 1,1-difluoro-2-naphthyl-ethanesulfonate, 1,1,2,2-tetrafluoro-2-(norbornan-2-yl)ethanesulfonate, and 1,1,2,2-tetrafluoro-2-(tetracyclo[4.4.0.1$^{2,5}$.1$^{7,10}$]dodec-3-en-8-yl)ethanesulfonate. Exemplary bis(substituted alkylsulfonyl)imides include bistrifluoromethylsulfonylimide, bispentafluoroethylsulfonylimide, bisheptafluoropropylsulfonylimide, and 1,3-propylenebissulfonylimide. A typical tris(substituted alkylsulfonyl)methide is tristrifluoromethylsulfonylmethide. Iodonium salts based on combination of the foregoing examples are included.

Exemplary sulfonyldiazomethane compounds include bissulfonyldiazomethane compounds and sulfonyl-carbonyldiazomethane compounds such as bis(ethylsulfonyl)diazomethane, bis(1-methylpropylsulfonyl)diazomethane, bis(2-methylpropylsulfonyl)diazomethane, bis(1,1-dimethylethylsulfonyl)diazomethane, bis(cyclohexylsulfonyl)diazomethane, bis(perfluoroisopropylsulfonyl)diazomethane, bis(phenylsulfonyl)diazomethane, bis(4-methylphenylsulfonyl)diazomethane, bis(2,4-dimethylphenylsulfonyl)diazomethane, bis(4-acetyloxyphenylsulfonyl)diazomethane, bis(4-methanesulfonyloxyphenylsulfonyl)diazomethane, bis(4-(4-toluenesulfonyloxy)phenylsulfonyl)diazomethane, bis(2-naphthylsulfonyl)diazomethane, 4-methylphenylsulfonylbenzoyldiazomethane, tert-butylcarbonyl-4-methylphenylsulfonyldiazomethane, 2-naphthylsulfonylbenzoyldiazomethane, 4-methylphenylsulfonyl-2-naphthoyldiazomethane, methylsulfonylbenzoyldiazomethane, and tert-butoxycarbonyl-4-methylphenylsulfonyldiazomethane.

N-sulfonyloxydicarboxyimide photoacid generators include combinations of imide skeletons with sulfonates. Exemplary imide skeletons are succinimide, naphthalenedicarboxyimide, phthalimide, cyclohexyldicarboxyimide, 5-norbornene-2,3-dicarboxyimide, and 7-oxabicyclo[2.2.1]-5-heptene-2,3-dicarboxyimide. Exemplary sulfonates include trifluoromethanesulfonate, pentafluoroethanesulfonate, heptafluoropropanesulfonate, nonafluorobutanesulfonate, dodecafluorohexanesulfonate, pentafluoroethylperfluorocyclohexanesulfonate, heptadecafluorooctanesulfonate, 2,2,2-trifluoroethanesulfonate, pentafluorobenzenesulfonate, 4-trifluoromethylbenzenesulfonate, 4-fluorobenzenesulfonate, mesitylenesulfonate, 2,4,6-triisopropylbenzenesulfonate, toluenesulfonate, benzenesulfonate, naphthalenesulfonate, camphorsulfonate, octanesulfonate, dodecylbenzenesulfonate, butanesulfonate, methanesulfonate, 1,1-difluoro-2-naphthyl-ethanesulfonate, 1,1,2,2-tetrafluoro-2-(norbornan-2-yl)ethanesulfonate, and 1,1,2,2-tetrafluoro-2-(tetracyclo[4.4.0.1$^{2,5}$.1$^{7,10}$]dodec-3-en-8-yl)ethanesulfonate.

Benzoinsulfonate photoacid generators include benzoin tosylate, benzoin mesylate, and benzoin butanesulfonate.

Pyrogallol trisulfonate photoacid generators include pyrogallol, fluoroglycine, catechol, resorcinol, hydroquinone, in which all the hydroxyl groups are substituted by trifluoromethanesulfonate, pentafluoroethanesulfonate, heptafluoropropanesulfonate, nonafluorobutanesulfonate, dodecafluorohexanesulfonate, pentafluoroethylperfluorocyclohexanesulfonate, heptadecafluorooctanesulfonate, 2,2,2-trifluoroethanesulfonate, pentafluorobenzenesulfonate, 4-trifluoromethylbenzenesulfonate, 4-fluorobenzenesulfonate, toluenesulfonate, benzenesulfonate, naphthalenesulfonate, camphorsulfonate, octanesulfonate, dodecylbenzenesulfonate, butanesulfonate, methanesulfonate, 1,1-difluoro-2-naphthyl-ethanesulfonate, 1,1,2,2-tetrafluoro-2-(norbornan-2-yl)ethanesulfonate, 1,1,2,2-tetrafluoro-2-(tetracyclo[4.4.0.1$^{2,5}$.1$^{7,10}$]dodec-3-en-8-yl)ethanesulfonate or the like.

Nitrobenzyl sulfonate photoacid generators include 2,4-dinitrobenzyl sulfonate, 2-nitrobenzyl sulfonate, and 2,6-dinitrobenzyl sulfonate, with exemplary sulfonates including trifluoromethanesulfonate, pentafluoroethanesulfonate, heptafluoropropanesulfonate, nonafluorobutanesulfonate, dodecafluorohexanesulfonate, pentafluoroethylperfluorocyclohexanesulfonate, heptadecafluorooctanesulfonate, 2,2,2-trifluoroethanesulfonate, pentafluorobenzenesulfonate, 4-trifluoromethylbenzenesulfonate, 4-fluorobenzenesulfonate, toluenesulfonate, benzenesulfonate, naphthalenesulfonate, camphorsulfonate, octanesulfonate, dodecylbenzenesulfonate, butanesulfonate, methanesulfonate, 1,1-difluoro-2-naphthyl-ethanesulfonate, 1,1,2,2-tetrafluoro-2-(norbornan-2-yl)ethanesulfonate, 1,1,2,2-tetrafluoro-2-(tetracyclo[4.4.0.1$^{2,5}$.1$^{7,10}$]dodec-3-en-8-yl)ethanesulfonate. Also useful are analogous nitrobenzyl sulfonate compounds in which the nitro group on the benzyl side is substituted by a trifluoromethyl group.

Sulfone photoacid generators include bis(phenylsulfonyl)methane, bis(4-methylphenylsulfonyl)methane, bis(2-naphthylsulfonyl)methane, 2,2-bis(phenylsulfonyl)propane, 2,2-bis(4-methylphenylsulfonyl)propane, 2,2-bis(2-naphthylsulfonyl)propane, 2-methyl-2-(p-toluenesulfonyl)propiophenone, 2-cyclohexylcarbonyl-2-(p-toluenesulfonyl)propane, and 2,4-dimethyl-2-(p-toluenesulfonyl)pentan-3-one.

Suitable O-arylsulfonyloxime compounds and O-alkylsulfonyloxime compounds (oxime sulfonates) include photoacid generators in the form of glyoxime derivatives (as described in Japanese Patent No. 2,906,999 and JP-A 9-301948); photoacid generators in the form of oxime sulfonates with a long conjugated system separated by thiophene or cyclohexadiene (as described in U.S. Pat. No. 6,004,724); oxime sulfonates having an electron withdrawing group such as trifluoromethyl incorporated for increased stability (as described in U.S. Pat. No. 6,261,738, JP-A 2000-314956, International Publication No. 2004-074242); oxime sulfonates using phenylacetonitrile or substituted acetonitrile derivatives (as described in JP-A 9-95479, JP-A 9-230588 and the compounds described in the prior art section thereof); and bisoxime sulfonates (as described in JP-A 9-208554, GB 2348644A, JP-A 2002-278053).

When the photoacid generator (E) is added to the KrF excimer laser resist composition, preference is given to sulfonium salts, bissulfonyldiazomethanes, N-sulfonyloxydicarboxyimides and oxime sulfonates. Illustrative preferred photoacid generators include triphenylsulfonium p-toluenesulfonate, triphenylsulfonium camphorsulfonate, triphenylsulfonium pentafluorobenzenesulfonate, triphenylsulfonium nonafluorobutanesulfonate, triphenylsulfonium 4-(4'-toluenesulfonyloxy)benzenesulfonate, triphenylsulfonium 2,4,6-triisopropylbenzenesulfonate, 4-tert-butoxyphenyldiphenylsulfonium p-toluenesulfonate, 4-tert-butoxyphenyldiphenylsulfonium camphorsulfonate, 4-tert-butoxyphenyldiphenylsulfonium 4-(4'-toluenesulfonyl-oxy)benzenesulfonate, tris(4-methylphenyl)sulfonium camphorsulfonate, tris(4-tert-butylphenyl)sulfonium camphorsulfonate, bis(tert-butylsulfonyl)diazomethane, bis(cyclohexylsulfonyl)diazomethane, bis(2,4-dimethylphenylsulfonyl)diazomethane, bis(4-tert-butylphenylsulfonyl)diazomethane, N-camphorsulfonyloxy-5-norbornene-2,3-carboxylic acid imide, N-p-toluenesulfonyloxy-5-norbornene-2,3-carboxylic acid imide, (5-(10-camphorsulfonyl)oxyimino-5H-thiophen-2-ylidene)(2-methylphenyl)acetonitrile, and (5-(4-toluenesulfonyl)oxyimino-5H-thiophen-2-ylidene)(2-methylphenyl) acetonitrile.

When the photoacid generator (E) is added to the ArF laser resist composition, preference is given to sulfonium salts and oxime sulfonates. Illustrative preferred photoacid generators include triphenylsulfonium trifluoromethanesulfonate, triphenylsulfonium nonafluorobutanesulfonate, diphenyl-4-methylphenylsulfonium nonafluorobutanesulfonate, 2-oxo-2-phenylethylthiacyclopentanium nonafluorobutanesulfonate, triphenylsulfonium perfluoro-4-ethylcyclohexanesulfonate, 4-tert-butylphenyldiphenylsulfonium nonafluorobutanesulfonate, 4-tert-butylphenyldiphenylsulfonium heptadecafluorooctane-sulfonate, and 2,2,3,3,4,4,5,5,6,6,7,7-decafluoro-1-(2-fluorenyl)heptanone-oxime perfluoro-1-butanesulfonate.

When the photoacid generator (E) is added to the ArF immersion lithography resist composition, preference is given to sulfonium salts and oxime sulfonates. Illustrative preferred photoacid generators include triphenylsulfonium nonafluorobutanesulfonate, diphenyl-4-methylphenylsulfonium nonafluorobutanesulfonate, triphenylsulfonium perfluoro-4-ethylcyclohexanesulfonate, 4-tert-butylphenyldiphenylsulfonium nonafluorobutanesulfonate, 4-tert-butylphenyldiphenylsulfonium heptadecafluorooctane-sulfonate, and 2,2,3,3,4,4,5,5,6,6,7,7-decafluoro-1-(2-fluorenyl)heptanone-oxime perfluoro-1-butanesulfonate.

In the chemically amplified resist composition comprising the photoacid generator capable of generating the sulfonic acid of formula (1a) as the first photoacid generator (A) according to the invention, the auxiliary photoacid generator (E) may be used in any desired amount as long as it does not compromise the effects of the invention. An appropriate amount of the auxiliary photoacid generator (E) is 0 to 10 parts, and especially 0 to 5 parts by weight per 100 parts by weight of the base resin in the composition. Too high a proportion of the auxiliary photoacid generator (E) may give rise to problems of degraded resolution and foreign matter upon development and resist film peeling. The auxiliary photoacid generators may be used alone or in admixture of two or more. The transmittance of the resist film can be controlled by using an (auxiliary) photoacid generator having a low transmittance at the exposure wavelength and adjusting the amount of the photoacid generator added.

In the resist composition of the invention, there may be added a compound which is decomposed with an acid to generate another acid, that is, acid amplifier compound. For these compounds, reference should be made to J. Photopolym. Sci. and Tech., 8, 43-44, 45-46 (1995), and ibid., 9, 29-30 (1996).

Examples of the acid amplifier compound include tert-butyl-2-methyl-2-tosyloxymethyl acetoacetate and 2-phenyl-2-(2-tosyloxyethyl)-1,3-dioxolane, but are not limited thereto. Of well-known photoacid generators, many of those compounds having poor stability, especially poor thermal stability exhibit an acid amplifier-like behavior.

In the resist composition of the invention, an appropriate amount of the acid amplifier compound is up to 2 parts, and especially up to 1 part by weight per 100 parts by weight of the base resin. Excessive amounts of the acid amplifier compound make diffusion control difficult, leading to degradation of resolution and pattern profile.

Component F

Component (F) is an organic acid derivative and/or a fluorinated alcohol.

Illustrative, non-limiting, examples of the organic acid derivatives include phenol, cresol, catechol, resorcinol, pyrogallol, fluoroglycin, bis(4-hydroxyphenyl)methane, 2,2-bis(4'-hydroxyphenyl)propane, bis(4-hydroxyphenyl)sulfone, 1,1,1-tris(4'-hydroxyphenyl)ethane, 1,1,2-tris(4'-hydroxyphenyl)ethane, hydroxybenzophenone, 4-hydroxyphenylacetic acid, 3-hydroxyphenylacetic acid, 2-hydroxyphenylacetic acid, 3-(4-hydroxyphenyl)propionic acid, 3-(2-hydroxyphenyl)propionic acid, 2,5-dihydroxyphenylacetic acid, 3,4-dihydroxyphenylacetic acid, 1,2-phenylenediacetic acid, 1,3-phenylenediacetic acid, 1,4-phenylenediacetic acid, 1,2-phenylenedioxydiacetic acid, 1,4-phenylenedipropanoic acid, benzoic acid, salicylic acid, 4,4-bis(4'-hydroxyphenyl) valeric acid, 4-tert-butoxyphenylacetic acid, 4-(4-hydroxyphenyl)butyric acid, 3,4-dihydroxymandelic acid, and 4-hydroxymandelic acid. Of these, salicylic acid and 4,4-bis(4'-hydroxyphenyl)valeric acid are preferred. They may be used alone or in admixture of two or more.

The fluorinated alcohol is an alcohol which is substituted with fluorine atoms except α-position. Those compounds terminated with 1,1,1,3,3,3-hexafluoro-2-propanol are desirable although the fluorinated alcohols are not limited thereto. Illustrative examples of the desirable fluorinated alcohols are given below.

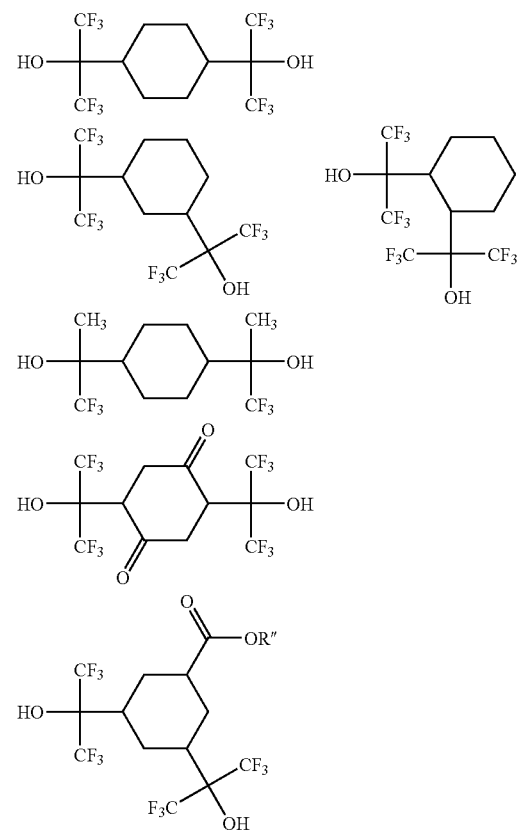

-continued
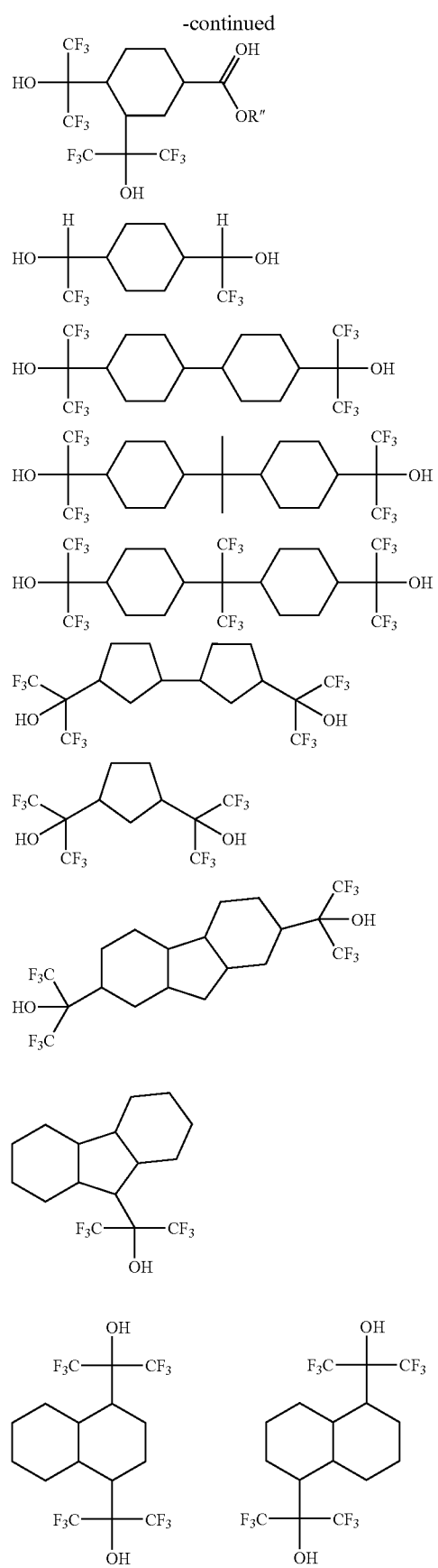
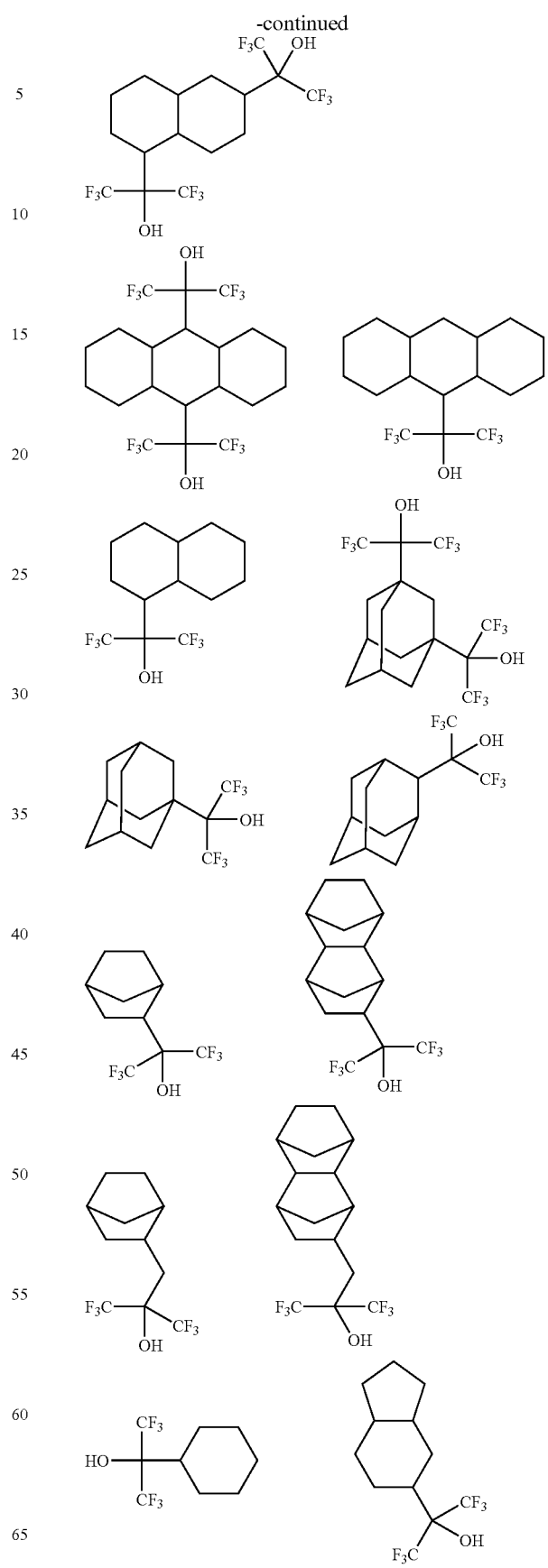

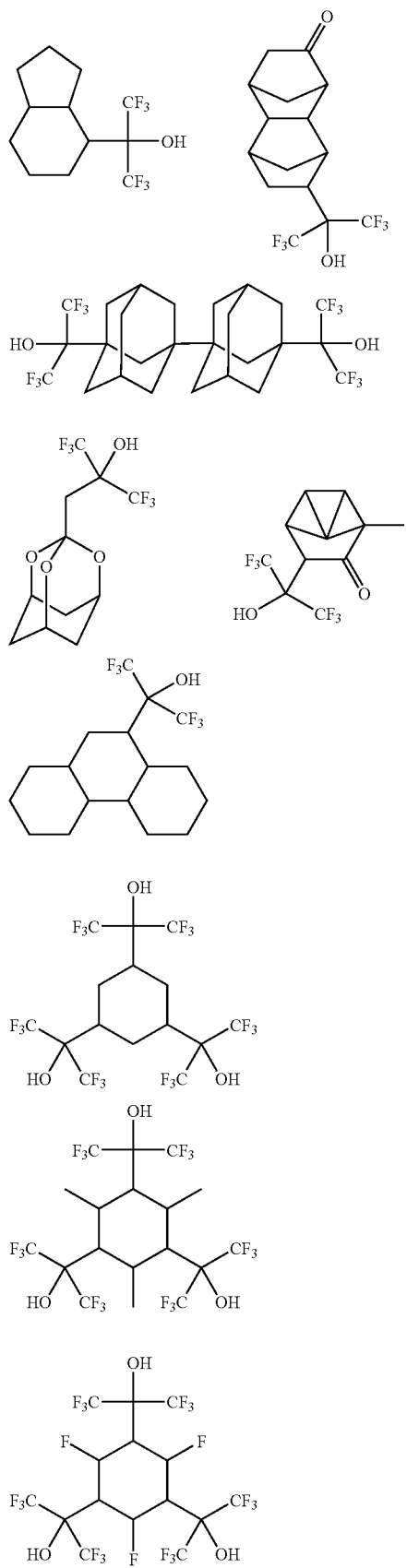
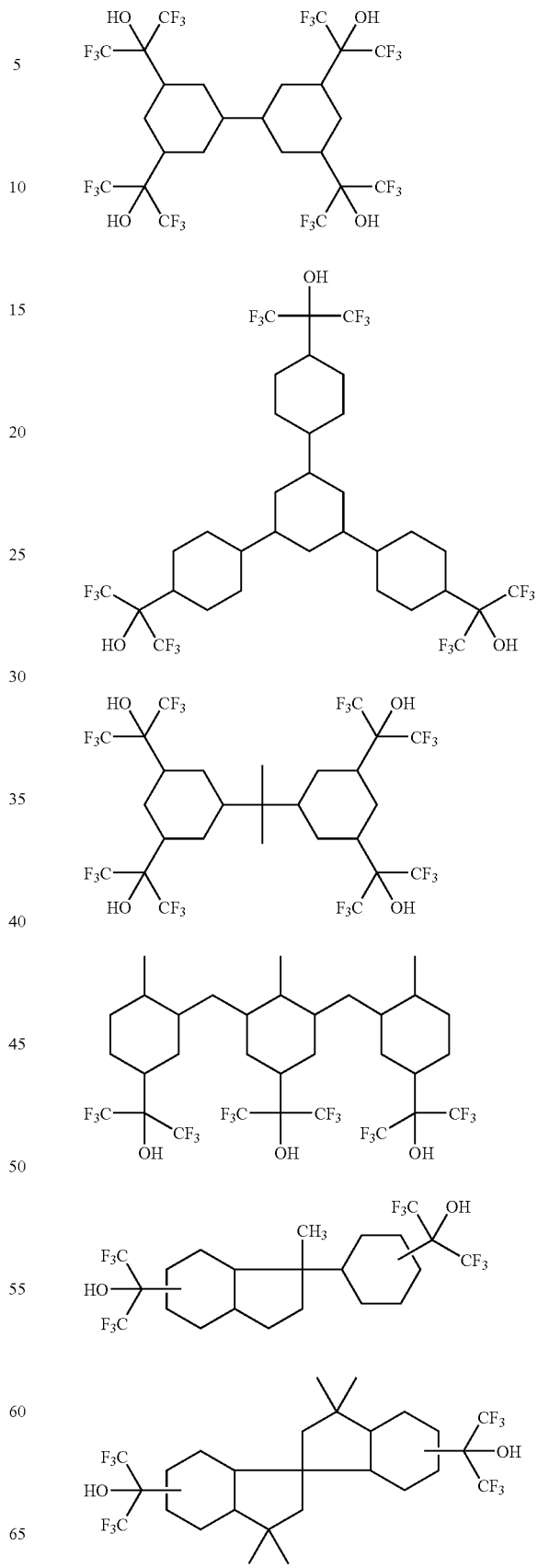

-continued

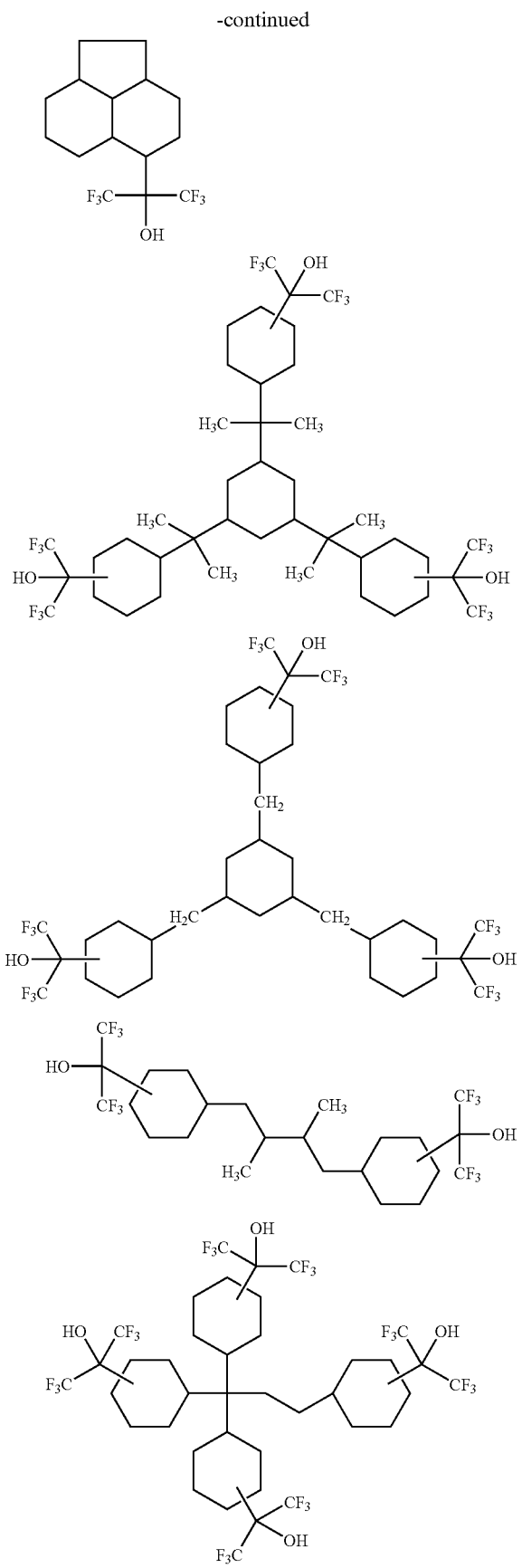

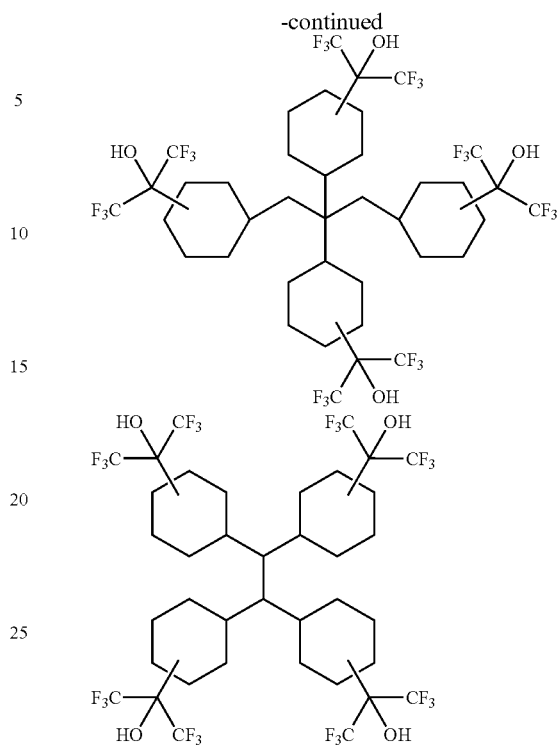

Note that R" is selected from $C_2$-$C_{30}$ acetal groups and $C_4$-$C_{30}$ tertiaryl alkyl groups having formulae (C1) and (C2) which have been described in the "base resin" section.

In the chemically amplified resist composition of the invention, the organic acid derivative or fluorinated alcohol is preferably formulated in an amount of up to 5 parts, and especially up to 1 part by weight, per 100 parts by weight of the base resin. More than 5 parts would result in too low a resolution. Depending on the combination of the other components in the resist composition, the organic acid derivative and fluorinated alcohol may be omitted.

Component G

In one preferred embodiment, the resist composition further contains (G) a compound with a weight average molecular weight of up to 3,000 which changes its solubility in an alkaline developer under the action of an acid, that is, a dissolution inhibitor. Typically, a compound obtained by substituting acid labile substituents for some or all hydrogen atoms of hydroxyl groups on a phenol or carboxylic acid derivative having a low molecular weight of up to 2,500 or fluorinated alcohol is added as the dissolution inhibitor.

Examples of the phenol or carboxylic acid derivative having a molecular weight of up to 2,500 include bisphenol A, bisphenol H, bisphenol S, 4,4-bis(4'-hydroxyphenyl)valeric acid, tris(4-hydroxyphenyl)methane, 1,1,1-tris(4'-hydroxyphenyl)ethane, 1,1,2-tris(4'-hydroxyphenyl)ethane, phenolphthalein, thymolphthalein, cholic acid, deoxycholic acid, and lithocholic acid. Examples of the fluorinated alcohol are as described above for component (F). The acid labile substituents are the same as those exemplified as the acid labile groups in the polymer.

Illustrative, non-limiting, examples of the dissolution inhibitors which are useful herein include bis(4-(2'-tetrahydropyranyloxy)phenyl)methane, bis(4-(2'-tetrahydrofuranyloxy)phenyl)methane, bis(4-tert-butoxyphenyl)methane, bis(4-tert-butoxycarbonyloxyphenyl)methane, bis(4-tertbutoxycarbonylmethyloxyphenyl)methane, bis(4-(1'-ethoxyethoxy)phenyl)methane, bis(4-(1'-ethoxypropyloxy)phenyl)methane, 2,2-bis(4'-(2"-tetrahydropyranyloxy))propane, 2,2-bis(4'-(2"-tetrahydrofuranyloxy)phenyl)propane, 2,2-bis(4'-tert-butoxyphenyl)propane, 2,2-bis(4'-tert-butoxycarbonyloxyphenyl)propane, 2,2-bis(4-tert-butoxycarbonylmethyloxyphenyl)propane, 2,2-bis(4-(1"-ethoxyethoxy)phenyl)propane, 2,2-bis(4'-(1"-ethoxypropyloxy)phenyl)propane, tert-butyl 4,4-bis(4'-(2"-tetrahydropyranyloxy)phenyl)-valerate, tert-butyl 4,4-bis(4'-(2"-tetrahydrofuranyloxy)phenyl)-valerate, tert-butyl 4,4-bis(4'-tert-butoxyphenyl)valerate, tert-butyl 4,4-bis(4-tert-butoxycarbonyloxyphenyl)valerate, tert-butyl 4,4-bis(4'-tert-butoxycarbonylmethyloxyphenyl)-valerate, tert-butyl 4,4-bis(4'-(1"-ethoxyethoxy)phenyl)valerate, tert-butyl 4,4-bis(4'-(1"-ethoxypropyloxy)phenyl)valerate, tris(4-(2'-tetrahydropyranyloxy)phenyl)methane, tris(4-(2'-tetrahydrofuranyloxy)phenyl)methane, tris(4-tert-butoxyphenyl)methane, tris(4-tert-butoxycarbonyloxyphenyl)methane, tris(4-tert-butoxycarbonyloxymethylphenyl)methane, tris(4-(1'-ethoxyethoxy)phenyl)methane, tris(4-(1'-ethoxypropyloxy)phenyl)methane, 1,1,2-tris(4'-(2"-tetrahydropyranyloxy)phenyl)ethane, 1,1,2-tris(4'-(2"-tetrahydrofuranyloxy)phenyl)ethane, 1,1,2-tris(4'-tert-butoxyphenyl)ethane, 1,1,2-tris(4'-tert-butoxycarbonyloxyphenyl)ethane, 1,1,2-tris(4'-tert-butoxycarbonylmethyloxyphenyl)ethane, 1,1,2-tris(4'-(1'-ethoxyethoxy)phenyl)ethane, 1,1,2-tris(4'-(1'-ethoxypropyloxy)phenyl)ethane, tert-butyl cholate, tert-butyl deoxycholate, and tert-butyl lithocholate. The compounds described in JP-A 2003-107706 are also useful.

In the resist composition of the invention, an appropriate amount of the dissolution inhibitor (G) is up to 20 parts, and especially up to 15 parts by weight per 100 parts by weight of the base resin. With more than 20 parts of the dissolution inhibitor, the resist composition becomes less heat resistant because of an increased content of monomer components.

Component C'

The base resin used in the negative working resist composition is (C') a base resin which is normally alkali soluble, but becomes substantially alkali insoluble under the action of a crosslinker. It is preferably a precursor resin which will be substituted with acid labile groups to form the base resin (C).

Examples of the alkali-soluble resin include poly(p-hydroxystyrene), poly(m-hydroxystyrene), poly(4-hydroxy-2-methylstyrene), poly(4-hydroxy-3-methylstyrene), poly(α-methyl-p-hydroxystyrene), partially hydrogenated p-hydroxystyrene copolymers, p-hydroxystyrene-α-methyl-p-hydroxystyrene copolymers, p-hydroxystyrene-α-methylstyrene copolymers, p-hydroxystyrene-styrene copolymers, p-hydroxystyrene-m-hydroxystyrene copolymers, p-hydroxystyrene-styrene copolymers, p-hydroxystyrene-acrylic acid copolymers, p-hydroxystyrene-methacrylic acid copolymers, p-hydroxystyrene-methyl methacrylate copolymers, p-hydroxystyrene-acrylic acid-methyl methacrylate copolymers, p-hydroxystyrene-methyl acrylate copolymers, p-hydroxystyrene-methacrylic acid-methyl methacrylate copolymers, poly(methacrylic acid), poly(acrylic acid), acrylic acid-methyl acrylate copolymers, methacrylic acid-methyl methacrylate copolymers, acrylic acid-maleimide copolymers, methacrylic acid-maleimide copolymers, p-hydroxystyrene-acrylic acid-maleimide copolymers, and p-hydroxystyrene-methacrylic acid-maleimide copolymers, but are not limited to these combinations.

To impart a certain function, suitable substituent groups may be introduced into some of the phenolic hydroxyl and carboxyl groups on the foregoing polymer (to be protected with acid labile groups). Exemplary and preferred are substituent groups for improving adhesion to the substrate, substituent groups for improving etching resistance, and especially substituent groups which are relatively stable against acid and alkali and effective for controlling such that the dissolution rate in an alkali developer of unexposed and low exposed areas of a resist film may not become too high. Illustrative, non-limiting, substituent groups include 2-hydroxyethyl, 2-hydroxypropyl, methoxymethyl, methoxycarbonyl, ethoxycarbonyl, methoxycarbonylmethyl, ethoxycarbonylmethyl, 4-methyl-2-oxo-4-oxolanyl, 4-methyl-2-oxo-4-oxanyl, methyl, ethyl, n-propyl, isopropyl, n-butyl, sec-butyl, acetyl, pivaloyl, adamantyl, isoboronyl, and cyclohexyl. It is also possible to introduce acid-decomposable substituent groups such as tert-butoxycarbonyl and relatively acid-undecomposable substituent groups such as tert-butyl and tert-butoxycarbonylmethyl.

In the resist composition, the resin (C') is blended in any desired amount, preferably of 65 to 99 parts by weight, especially 65 to 98 parts by weight per 100 parts by weight of the total amount of the solid matters except the solvent.

Component H

Formulated in the negative resist composition is a crosslinker (F) which forms a crosslinked structure under the action of acid. Typical crosslinkers are compounds having at least two hydroxymethyl, alkoxymethyl, epoxy or vinyl ether groups within a molecule. Substituted glycoluril derivatives, urea derivatives, and hexa(methoxymethyl)melamine compounds are suitable as the crosslinker. Examples include N,N,N',N'-tetramethoxymethylurea, hexamethoxymethylmelamine, tetraalkoxymethyl-substituted glycoluril compounds such as tetrahydroxymethyl-substituted glycoluril and tetramethoxymethylglycoluril, and condensates of phenolic compounds such as substituted or unsubstituted bis(hydroxymethylphenol) compounds and bisphenol A with epichlorohydrin. Especially preferred crosslinkers are 1,3,5,7-tetraalkoxymethylglycolurils such as 1,3,5,7-tetramethoxymethylglycoluril, 1,3,5,7-tetrahydroxymethylglycoluril, 2,6-dihydroxymethyl-p-cresol, 2,6-dihydroxymethylphenol, 2,2',6,6'-tetrahydroxymethylbisphenol A, 1,4-bis[2-(2-hydroxypropyl)]benzene, N,N,N',N'-tetramethoxymethylurea, and hexamethoxymethylmelamine.

In the resist composition, an appropriate amount of the crosslinker is, though not limited thereto, about 1 to 20 parts, and especially about 5 to 15 parts by weight per 100 parts by weight of the base resin. The crosslinkers may be used alone or in admixture of two or more.

In the chemically amplified resist composition of the invention, there may be added such additives as a surfactant for improving coating characteristics, and a light absorbing agent for reducing diffuse reflection from the substrate.

Illustrative, non-limiting, examples of the surfactant include nonionic surfactants, for example, polyoxyethylene alkyl ethers such as polyoxyethylene lauryl ether, polyoxyethylene stearyl ether, polyoxyethylene cetyl ether, and polyoxyethylene oleyl ether, polyoxyethylene alkylaryl ethers such as polyoxyethylene octylphenol ether and polyoxyethylene nonylphenol ether, polyoxyethylene polyoxypropylene block copolymers, sorbitan fatty acid esters such as sorbitan monolaurate, sorbitan monopalmitate, and sorbitan monostearate, and polyoxyethylene sorbitan fatty acid esters such as polyoxyethylene sorbitan monolaurate, polyoxyethylene sorbitan monopalmitate, polyoxyethylene sorbitan monostearate, polyoxyethylene sorbitan trioleate, and polyoxyethylene sorbitan tristearate; fluorochemical surfactants such as EFTOP EF301, EF303 and EF352 (JEMCO Inc.), Megaface F171, F172, F173, R08 and R30 (Dai-Nippon Ink & Chemicals, Inc.), Fluorad FC430, FC431, FC-4430 and FC-4432 (Sumitomo 3M Co., Ltd.), Aashiguard AG710, Surflon S-381, S-382, SC101, SC102, SC103, SC104, SC105, SC106, Surfynol E1004, KH-10, KH-20, KH-30 and KH-40 (Asahi Glass Co., Ltd.); organosiloxane polymers KP341, X-70-092 and X-70-093 (Shin-Etsu Chemical Co., Ltd.), acrylic acid or methacrylic acid Polyflow No. 75 and No. 95 (Kyoeisha Ushi Kagaku Kogyo Co., Ltd.). Inter alia, FC430, Surflon S-381, Surfynol E1004, KH-20 and KH-30 are preferred. These surfactants may be used alone or in admixture.

In the chemically amplified resist composition of the invention, the surfactant is preferably formulated in an amount of up to 2 parts, and especially up to 1 part by weight, per 100 parts by weight of the base resin.

In the chemically amplified resist composition of the invention, a UV absorber may be added. Those UV absorbers described in JP-A 11-190904 are useful, but the invention is not limited thereto. Exemplary UV absorbers are diaryl sulfoxide derivatives such as bis(4-hydroxyphenyl)sulfoxide, bis(4-tert-butoxyphenyl)sulfoxide, bis(4-tert-butoxycarbonyloxyphenyl)sulfoxide, and bis[4-(1-ethoxyethoxy)phenyl] sulfoxide; diarylsulfone derivatives such as bis(4-hydroxyphenyl)sulfone, bis(4-tert-butoxyphenyl)sulfone, bis(4-tert-butoxycarbonyloxyphenyl)sulfone, bis[4-(1-ethoxyethoxy)phenyl]sulfone, and bis[4-(1-ethoxypropoxy)phenyl]sulfone; diazo compounds such as benzoquinonediazide, naphthoquinonediazide, anthraquinonediazide, diazofluorene, diazotetralone, and diazophenanthrone; quinonediazido group-containing compounds such as complete or partial ester compounds between naphthoquinone-1,2-diazido-5-sulfonic acid chloride and 2,3,4-trihydroxybenzophenone and complete or partial ester compounds between naphthoquinone-1,2-diazido-4-sulfonic acid chloride and 2,4,4'-trihydroxybenzophenone; tert-butyl 9-anthracenecarboxylate, tert-amyl 9-anthracenecarboxylate, tert-methoxymethyl 9-anthracenecarboxylate, tert-ethoxyethyl 9-anthracenecarboxylate, 2-tert-tetrahydropyranyl 9-anthracenecarboxylate, and 2-tert-tetrahydrofuranyl 9-anthracenecarboxylate.

The UV absorber may or may not be added to the resist composition depending on the type of resist composition. An appropriate amount of UV absorber, if added, is 0 to 10 parts, more preferably 0.5 to 10 parts, most preferably 1 to 5 parts by weight per 100 parts by weight of the base resin.

For the microfabrication of integrated circuits, any well-known lithography may be used to form a resist pattern from the chemically amplified resist composition of the invention.

The composition is applied onto a substrate (e.g., Si, $SiO_2$, SiN, SiON, TiN, WSi, BPSG, SOG, organic anti-reflective film, etc.) for microfabrication by a suitable coating technique such as spin coating, roll coating, flow coating, dip coating, spray coating or doctor coating. The coating is pre-baked on a hot plate at a temperature of 60 to 150° C. for about 1 to 10 minutes, preferably 80 to 120° C. for 1 to 5 minutes. The resulting resist film is generally 0.1 to 2.0 μm thick. Through a photomask having a desired pattern, the resist film is then exposed to radiation, preferably having an exposure wavelength of up to 300 nm, such as UV, deep-UV, electron beam, x-ray, excimer laser light, γ-ray and synchrotron radiation. The preferred light source is a beam from an excimer laser, especially KrF excimer laser, deep UV of 245-255 nm wavelength and ArF excimer laser. The exposure dose is preferably in the range of about 1 to 200 $mJ/cm^2$, more preferably about 10 to 100 $mJ/cm^2$. The film is further baked on a hot plate at 60 to 150° C. for 1 to 5 minutes, preferably 80 to 140° C. for 1 to 3 minutes (post-exposure baking=PEB).

Thereafter the resist film is developed with a developer in the form of an aqueous base solution, for example, 0.1 to 5 wt %, preferably 2 to 3 wt % aqueous solution of tetramethylammonium hydroxide (TMAH) for 0.1 to 3 minutes, preferably 0.5 to 2 minutes by conventional techniques such as dip, puddle or spray technique. In this way, a desired resist pattern is formed on the substrate. It is appreciated that the resist composition of the invention is best suited for micro-patterning using such actinic radiation as deep UV with a wavelength of 254 to 193 nm, vacuum UV with a wavelength of 157 nm, electron beam, x-ray, excimer laser light, γ-ray and synchrotron radiation. With any of the above-described parameters outside the above-described range, the process may sometimes fail to produce the desired pattern.

In the practice of the invention, the immersion lithography process of using ArF excimer laser of 193 nm wavelength and feeding a liquid such as water, glycerin or ethylene glycol between the wafer and the projection lens is advantageously applicable.

EXAMPLE

Synthesis Examples, Examples and Comparative Examples are given below for further illustrating the invention, but they are not to be construed as limiting the invention.

Synthesis Example 1

Synthesis of Triphenylsulfonium Chloride

Diphenyl sulfoxide, 40 g (0.2 mole), was dissolved in 400 g of dichloroethane, which was stirred under ice cooling. At a temperature below 20° C., 65 g (0.6 mole) of trimethylsilyl chloride was added dropwise to the solution, which was aged for 30 minutes at the temperature. Then, a Grignard reagent which had been prepared from 14.6 g (0.6 mole) of metallic magnesium, 67.5 g (0.6 mole) of chlorobenzene and 168 g of tetrahydrofuran (THF) was added dropwise at a temperature below 20° C. The reaction solution was aged for one hour, after which 50 g of water at a temperature below 20° C. was added to quench the reaction. To this solution, 150 g of water, 10 g of 12N hydrochloric acid, and 200 g of diethyl ether were further added.

The water layer was separated and washed with 100 g of diethyl ether, yielding an aqueous solution of triphenylsulfonium chloride. The compound in aqueous solution form was used in the subsequent reaction without further isolation.

Synthesis Example 2

Synthesis of 4-tert-butylphenyldiphenylsulfonium Bromide

The target compound was obtained by following the procedure of Synthesis Example 1 aside from using 4-tert-butylbromobenzene instead of the chlorobenzene in Synthesis Example 1 and increasing the amount of water for extraction.

Synthesis Example 3

Synthesis of 4-tert-butoxyphenyldiphenylsulfonium Chloride

The target compound was obtained by following the procedure of Synthesis Example 1 aside from using 4-tert-butoxychlorobenzene instead of the chlorobenzene in Synthesis Example 1, using dichloromethane containing 5 wt % of triethylamine as the solvent, and increasing the amount of water for extraction.

Synthesis Example 4

Synthesis of tris(4-methylphenyl)sulfonium Chloride

The target compound was obtained by following the procedure of Synthesis Example 1 aside from using bis(4-methylphenyl)sulfoxide instead of the diphenyl sulfoxide and 4-chlorotoluene instead of the chlorobenzene in Synthesis Example 1, and increasing the amount of water for extraction.

Synthesis Example 5

Synthesis of tris(4-tert-butylphenyl)sulfonium Bromide

The target compound was obtained by following the procedure of Synthesis Example 1 aside from using bis(4-tert-butylphenyl)sulfoxide instead of the diphenyl sulfoxide and 4-tert-butylbromobenzene instead of the chlorobenzene in Synthesis Example 1, and increasing the amount of water for extraction.

Synthesis Example 6

Synthesis of bis(4-tert-butylphenyl)iodonium Hydrogen Sulfate

A mixture of 84 g (0.5 mole) of tert-butylbenzene, 53 g (0.25 mole) of potassium iodate and 50 g of acetic anhydride was stirred under ice cooling, and a mixture of 35 g of acetic anhydride and 95 g of conc. sulfuric acid was added dropwise at a temperature below 30° C. The resulting solution was aged for 3 hours at room temperature and ice cooled again, after which 250 g of water was added dropwise to quench the reaction. The reaction solution was extracted with 400 g of dichloromethane. The organic layer was discolored by adding 6 g of sodium hydrogen sulfite. The organic layer was washed with 250 g of water three times. The washed organic layer was concentrated in vacuum, obtaining a crude target product. The product was used in the subsequent reaction without further purification.

Synthesis Example 7

Synthesis of phenacyltetrahydrothiophenium Bromide 88.2 g (0.44 mole) of phenacyl bromide and 39.1 g (0.44 mole) of tetrahydrothiophene were dissolved in 220 g of nitromethane, which was stirred for 4 hours at room temperature. 800 g of water and 400 g of diethyl ether were added to the reaction solution whereupon the mixture separated into two layers. The aqueous layer was taken out, which was an aqueous solution of the target compound, phenacyltetrahydrothiophenium bromide.

Synthesis Example 8

Synthesis of dimethylphenylsulfonium Hydrogen Sulfate 6.2 g (0.05 mole) of thioanisole and 6.9 g (0.055 mole) of dimethyl sulfate were stirred for 12 hours at room temperature. 100 g of water and 50 ml of diethyl ether were added to the reaction solution whereupon the mixture separated into two layers. The aqueous layer was taken out, which was an aqueous solution of the target compound, dimethylphenylsulfonium hydrogen sulfate.

Synthesis Example 9

Synthesis of Sodium 1,1,3,3,3-pentafluoro-2-benzoyloxy-propane-1-sulfonate (Anion 1)

10.0 g of 1,1,3,3,3-pentafluoropropen-2-yl benzoate which had been synthesized by a conventional technique, was dispersed in 72 g of water, after which 12.0 g of sodium hydrogen sulfite and 1.24 g of benzoyl peroxide were added. Reaction occurred at 85° C. for 65 hours. The reaction solution was allowed to cool, after which toluene was added, followed by separatory operation to separate a water layer. A saturated sodium chloride aqueous solution was added to the water layer whereupon white crystals settled out. The crystals were collected by filtration, washed with a small volume of saturated sodium chloride aqueous solution and then dried in vacuum, obtaining the target compound, sodium 1,1,3,3,3-pentafluoro-2-benzoyloxypropane-1-sulfonate. White crystals, 5.85 g (yield 43%).

Figure 2:
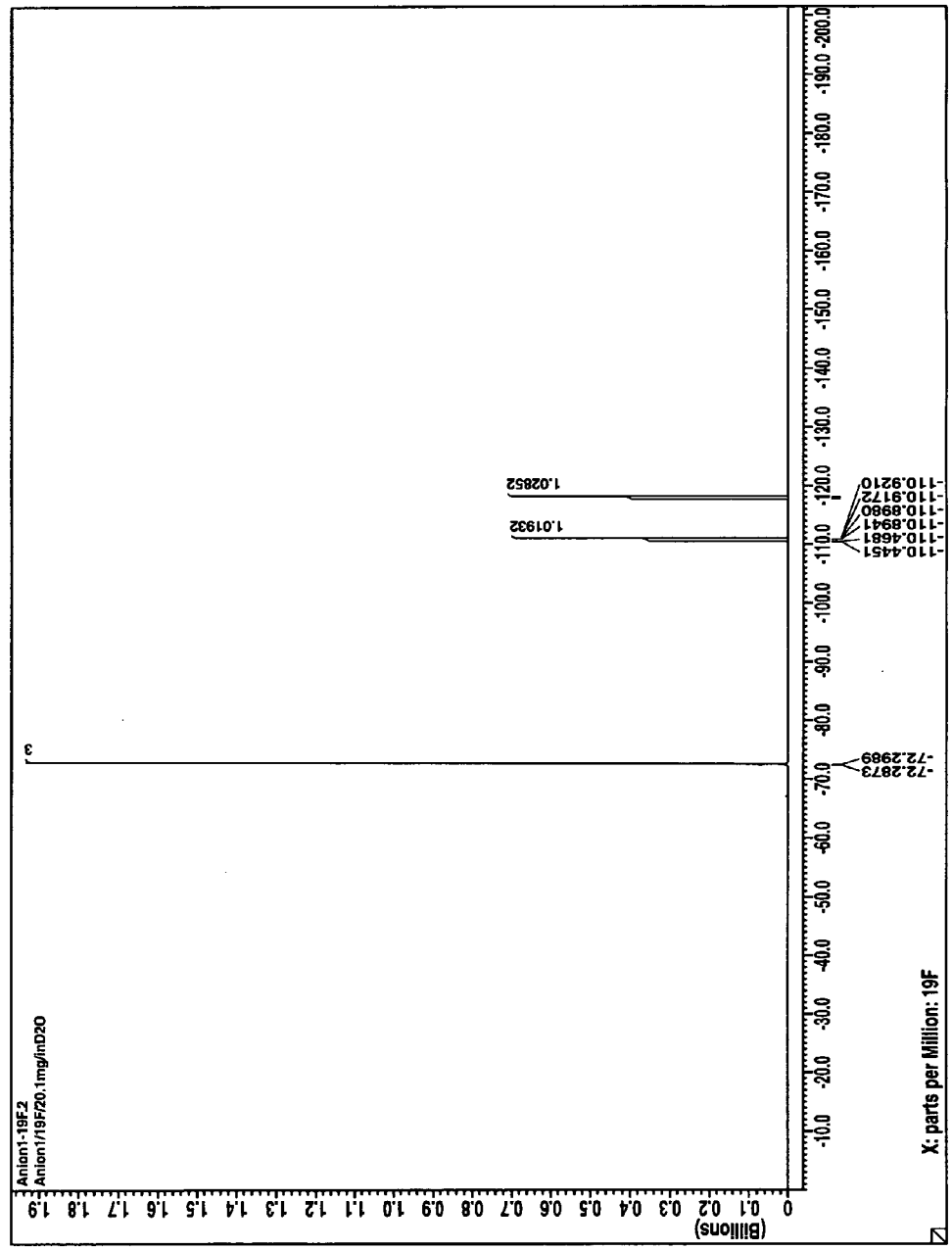
FIG. 2 is a diagram showing the $^{19}$F-NMR/D$_2$O spectrum of Anion 1 in Synthesis Example 9.

The target compound was analyzed by spectroscopy. The data of infrared absorption spectroscopy are shown below. The spectra of nuclear magnetic resonance spectroscopy ($^1$H-NMR and $^{19}$F-NMR/D$_2$O) are shown in FIGS. 1 and 2.

Infrared absorption spectra (IR; KBr disc, cm$^{-1}$) 1752, 1643, 1604, 1454, 1367, 1344, 1286, 1245, 1189, 1159, 1114, 1097, 1041, 1024, 1002, 908, 707, 647

Time-of-flight mass spectrometry (TOFMS; MALDI) NEGATIVE M$^-$333 (corresponding to CF$_3$CH(OCOC$_6$H$_5$)CF$_2$SO$_3^-$)

Synthesis Example 10

Synthesis of sodium 1,1,3,3,3-pentafluoro-2-(4-phenylbenzoyloxy)propanesulfonate (Anion 2)

The target sodium sulfonate was obtained by following the procedure of Synthesis Example 9 aside from using 1,1,3,3,3-pentafluoropropen-2-yl-4-phenyl benzoate which had been synthesized by a conventional technique.

Synthesis Example 11

Synthesis of triphenylsulfonium 1,1,3,3,3-pentafluoro-2-benzoyloxypropane-1-sulfonate (PAG1)

To 50 g of dichloromethane were added an amount (corresponding to 0.011 mole) of the triphenylsulfonium chloride aqueous solution of Synthesis Example 1 and 3.6 g (0.01 mole) of sodium 1,1,3,3,3-pentafluoro-2-benzoyloxy-propane-1-sulfonate synthesized in Synthesis Example 9, followed by stirring. The organic layer was separated and washed with 50 g of water three times. The organic layer was concentrated and 25 g of diethyl ether was added to the residue for crystallization. The crystals were filtered and dried, obtaining the target compound. White crystals, 4.5 g (yield 75%).

Figure 3:
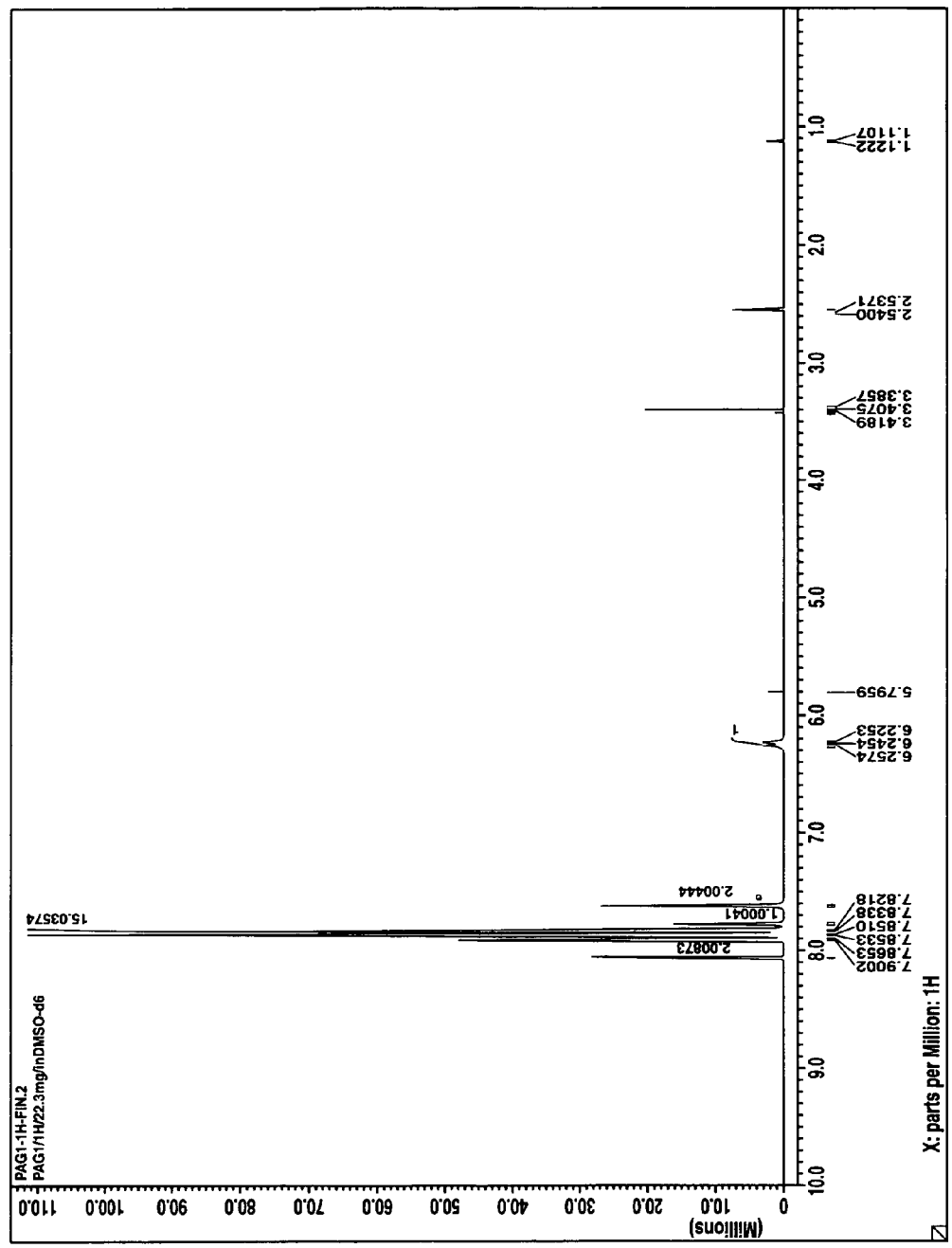
FIG. 3 is a diagram showing the $^1$H-NMR/DMSO-d$_6$ spectrum of PAG1 in Synthesis Example 11.
Figure 4:
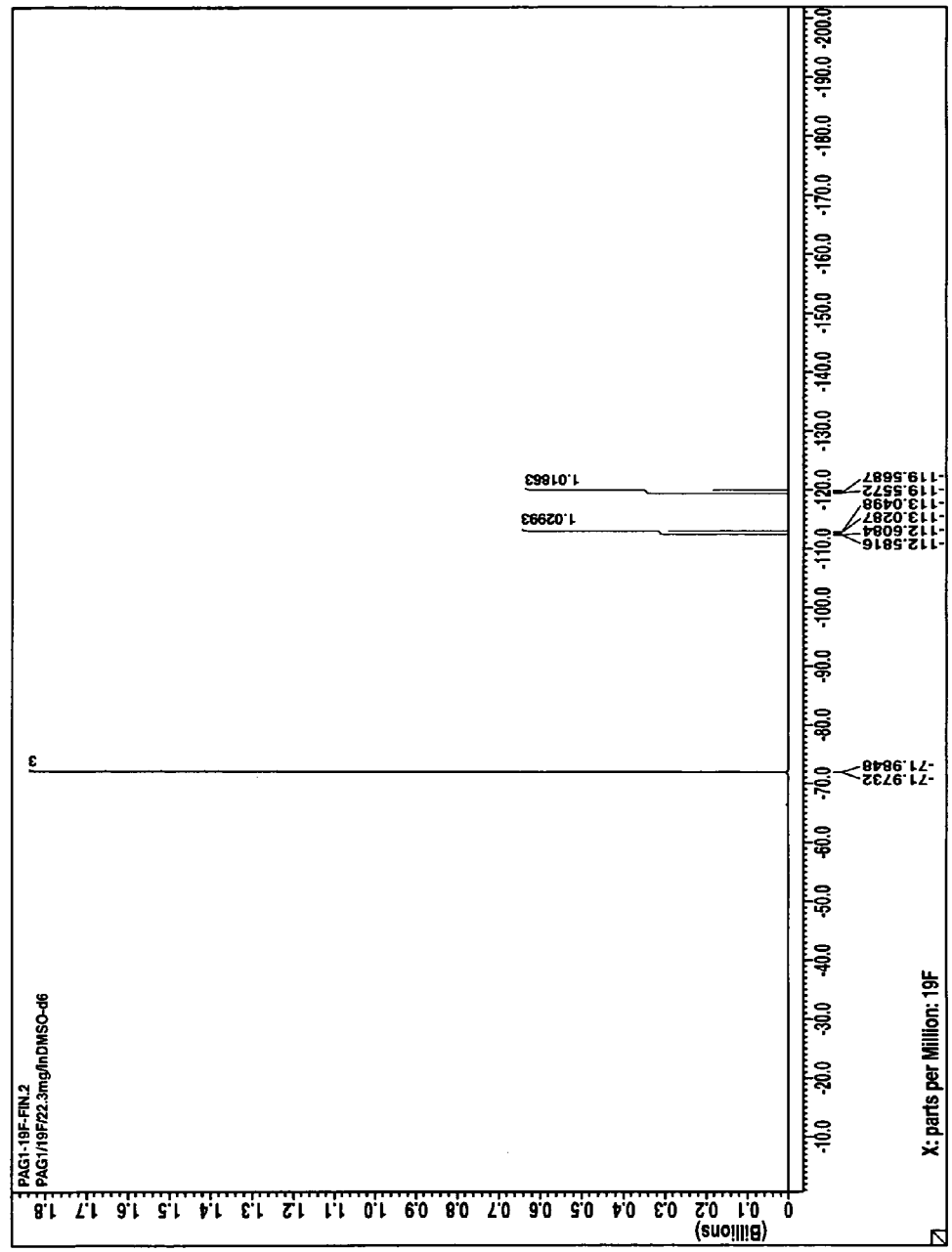
FIG. 4 is a diagram showing the $^{19}$F-NMR/DMSO-d$_6$ spectrum of PAG1 in Synthesis Example 11.

The target compound was analyzed by spectroscopy. The data of IR spectroscopy are shown below. The NMR spectra ($^1$H-NMR and $^{19}$F-NMR/DMSO-d$_6$) are shown in FIGS. 3 and 4.

Infrared absorption spectra (IR; KBr disc, cm$^{-1}$) 3085, 3064, 1739, 1600, 1477, 1448, 1375, 1328, 1215, 1192, 1167, 1109, 1072, 1043, 1022, 995, 939, 904, 840, 802, 754, 746, 713, 684, 640, 621, 574, 552, 503

Time-of-flight mass spectrometry (TOFMS; MALDI) POSITIVE M$^+$263 (corresponding to (C$_6$H$_5$)$_3$S$^+$) NEGATIVE M$^-$333 (corresponding to CF$_3$CH(OCOC$_6$H$_5$)CF$_2$SO$_3^-$)

Synthesis Example 12

Synthesis of triphenylsulfonium 1,1,3,3,3-pentafluoro-2-(4-phenylbenzoyloxy)propanesulfonate (PAG2)

The target compound was obtained by following the procedure of Synthesis Example 11 aside from using sodium 1,1,3,3,3-pentafluoro-2-(4-phenylbenzoyloxy)propane-1-sulfonate, obtained in Synthesis Example 10, instead of the sodium 1,1,3,3,3-pentafluoro-2-benzoyloxypropane-1-sulfonate used in Synthesis Example 11.

Figure 5:
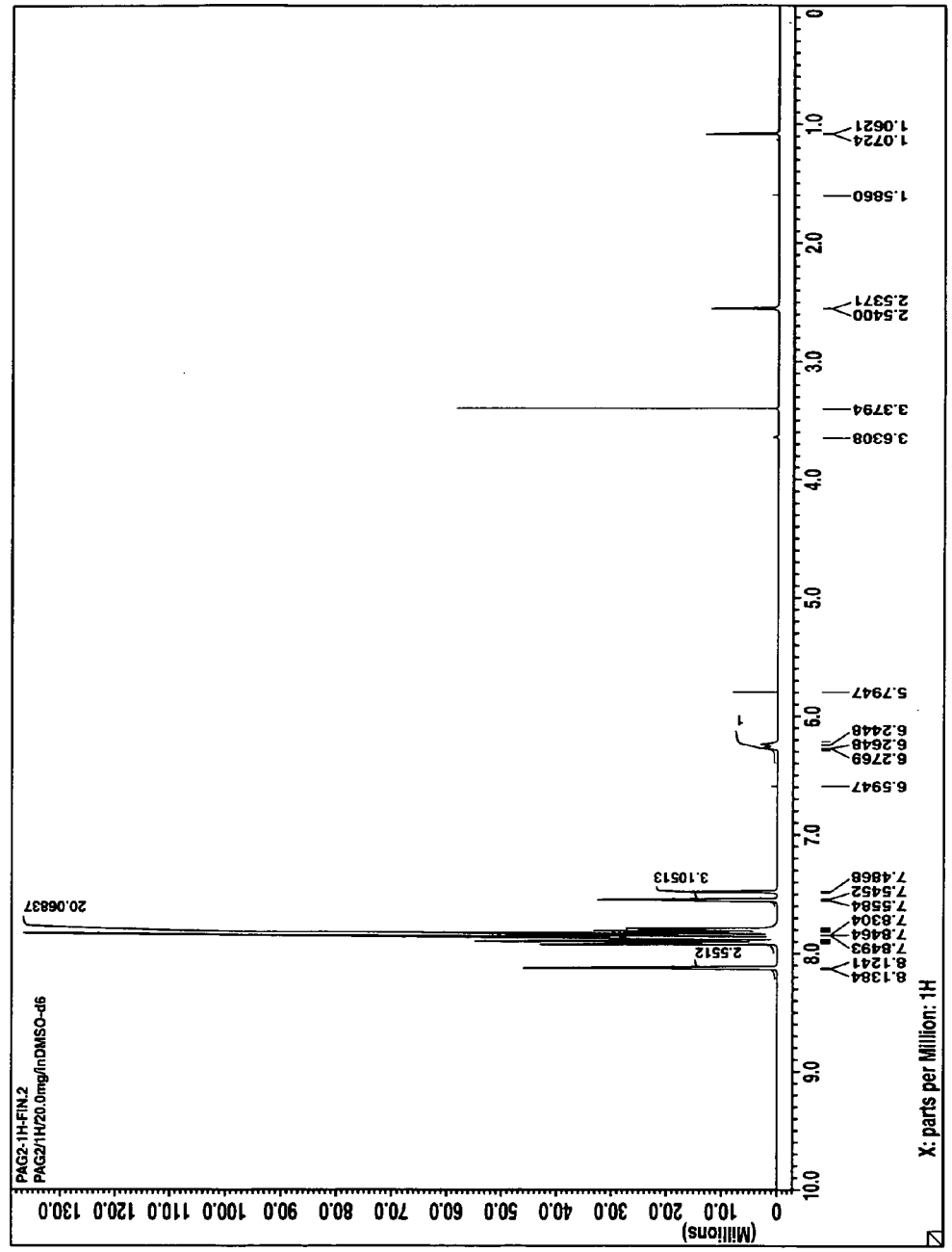
FIG. 5 is a diagram showing the $^1$H-NMR/DMSO-d$_6$ spectrum of PAG2 in Synthesis Example 12.
Figure 6:
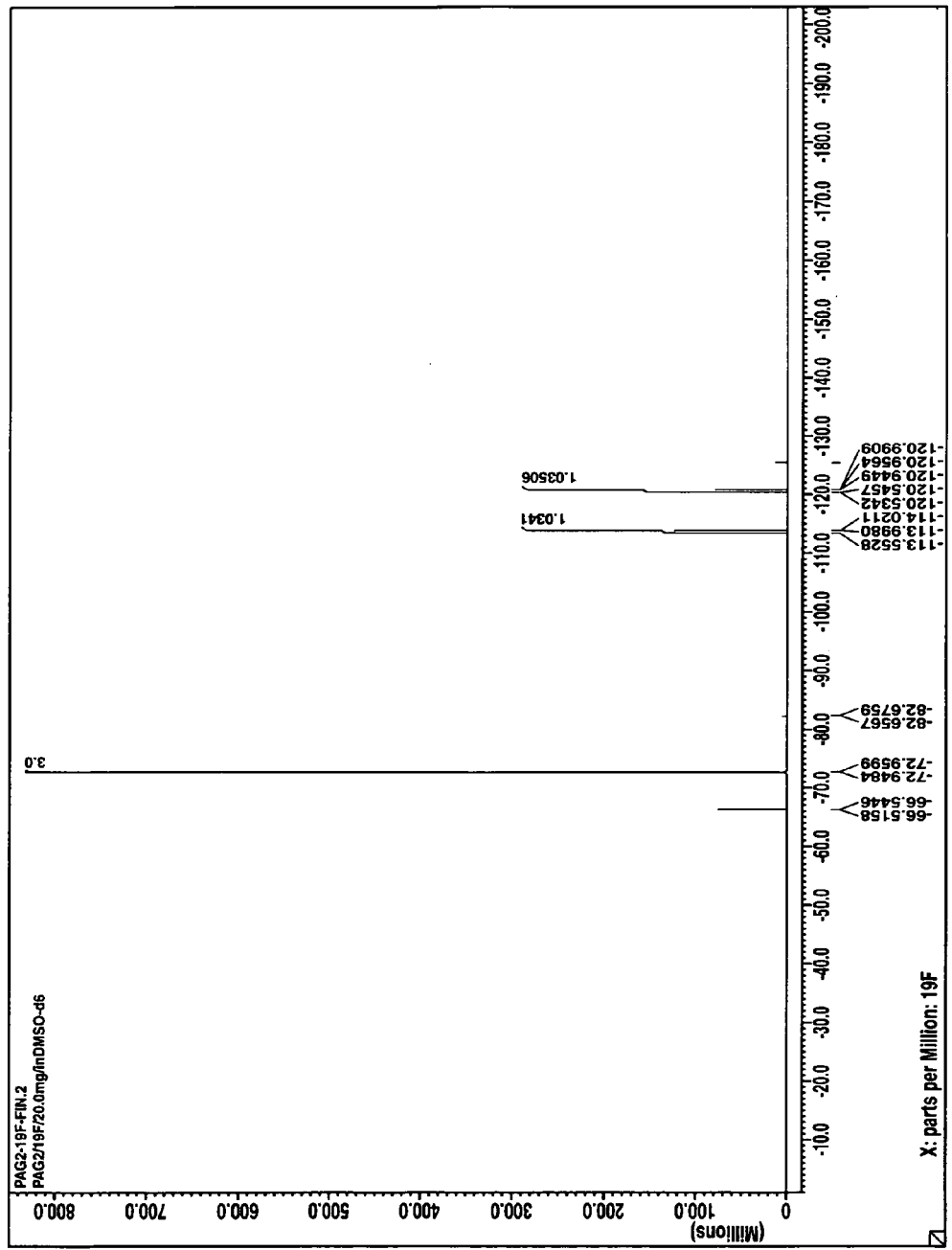
FIG. 6 is a diagram showing the $^{19}$F-NMR/DMSO-d$_6$ spectrum of PAG2 in Synthesis Example 12.

The target compound was analyzed by spectroscopy. The data of IR spectroscopy are shown below. The NMR spectra ($^1$H-NMR and $^{19}$F-NMR/DMSO-d$_6$) are shown in FIGS. 5 and 6.

Infrared absorption spectra (IR; KBr disc, cm$^{-1}$) 3062, 1743, 1606, 1489, 1477, 1448, 1408, 1373, 1327, 1253, 1215, 1186, 1164, 1103, 1072, 1016, 1006, 995, 902, 858, 838, 781, 746, 700, 684, 640, 622, 574, 551, 536, 518, 501

Time-of-flight mass spectrometry (TOFMS; MALDI) POSITIVE M$^+$263 (corresponding to (C$_6$H$_5$)$_3$S$^+$) NEGATIVE M$^-$409 (corresponding to CF$_3$CH(OCOC$_6$H$_4$C$_6$H$_5$)CF$_2$SO$_3^-$)

Synthesis Examples 13-26

Target compounds were synthesized as in Synthesis Example 11 except that the onium salts prepared in Synthesis Examples 2 to 8 and the sulfonate salts prepared in Synthesis Examples 9 and 10 were used. The resulting onium salts PAG3 to PAG16 are shown below.

Figure 7:
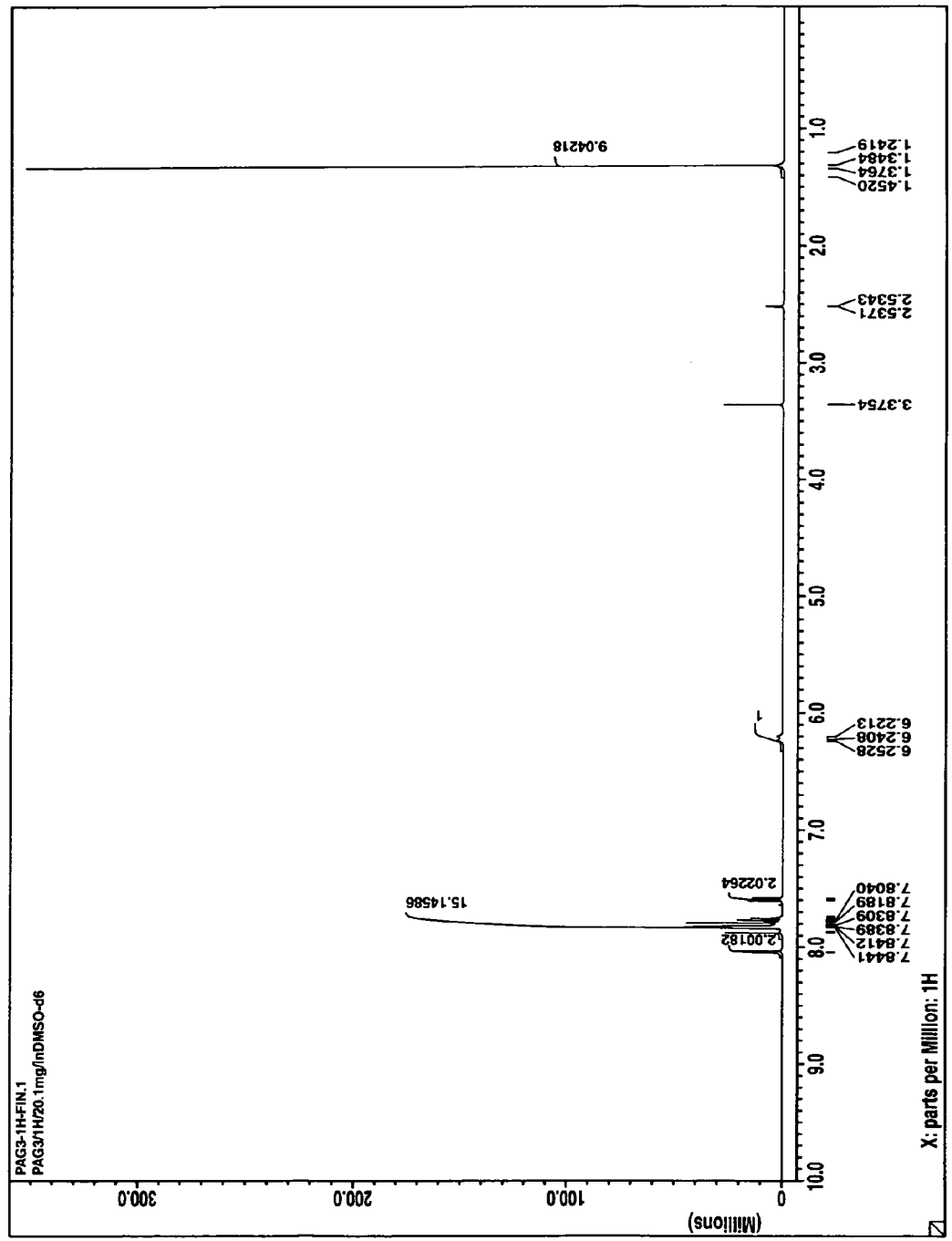
FIG. 7 is a diagram showing the $^1$H-NMR/DMSO-d$_6$ spectrum of PAG3 in Synthesis Example 13.
Figure 8:
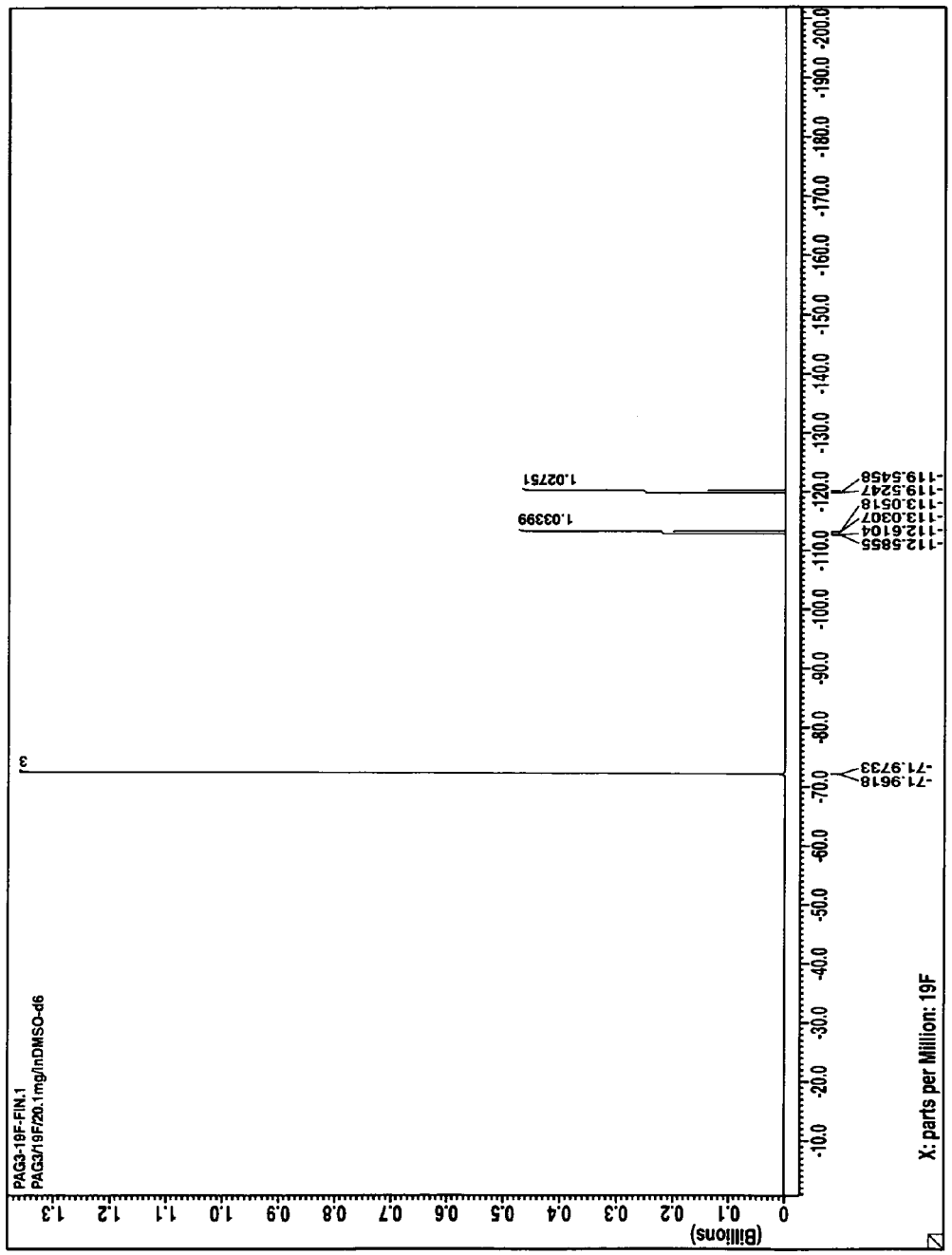
FIG. 8 is a diagram showing the $^{19}$F-NMR/DMSO-d$_6$ spectrum of PAG3 in Synthesis Example 13.
Figure 9:
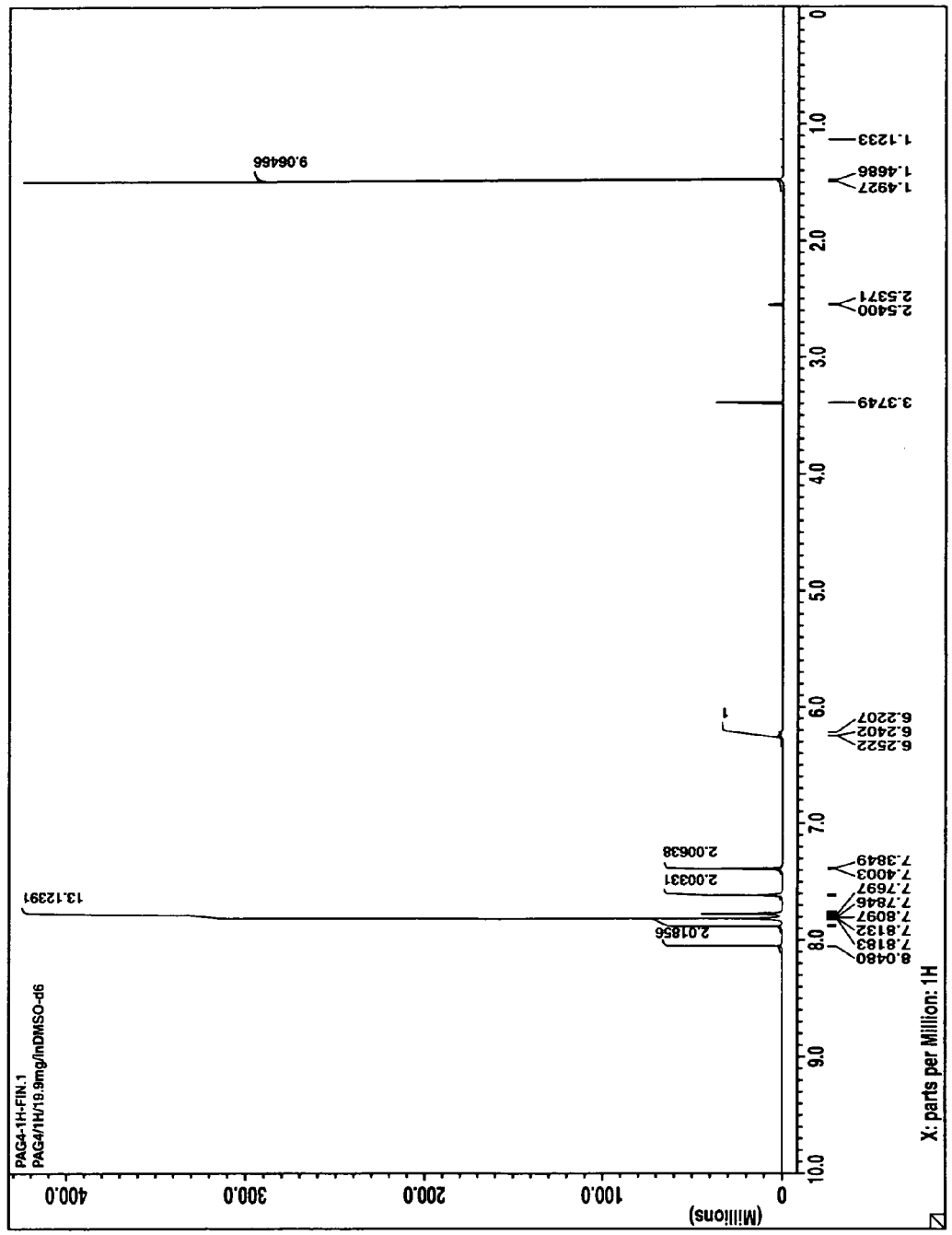
FIG. 9 is a diagram showing the $^1$H-NMR/DMSO-d$_6$ spectrum of PAG4 in Synthesis Example 14.
Figure 10:
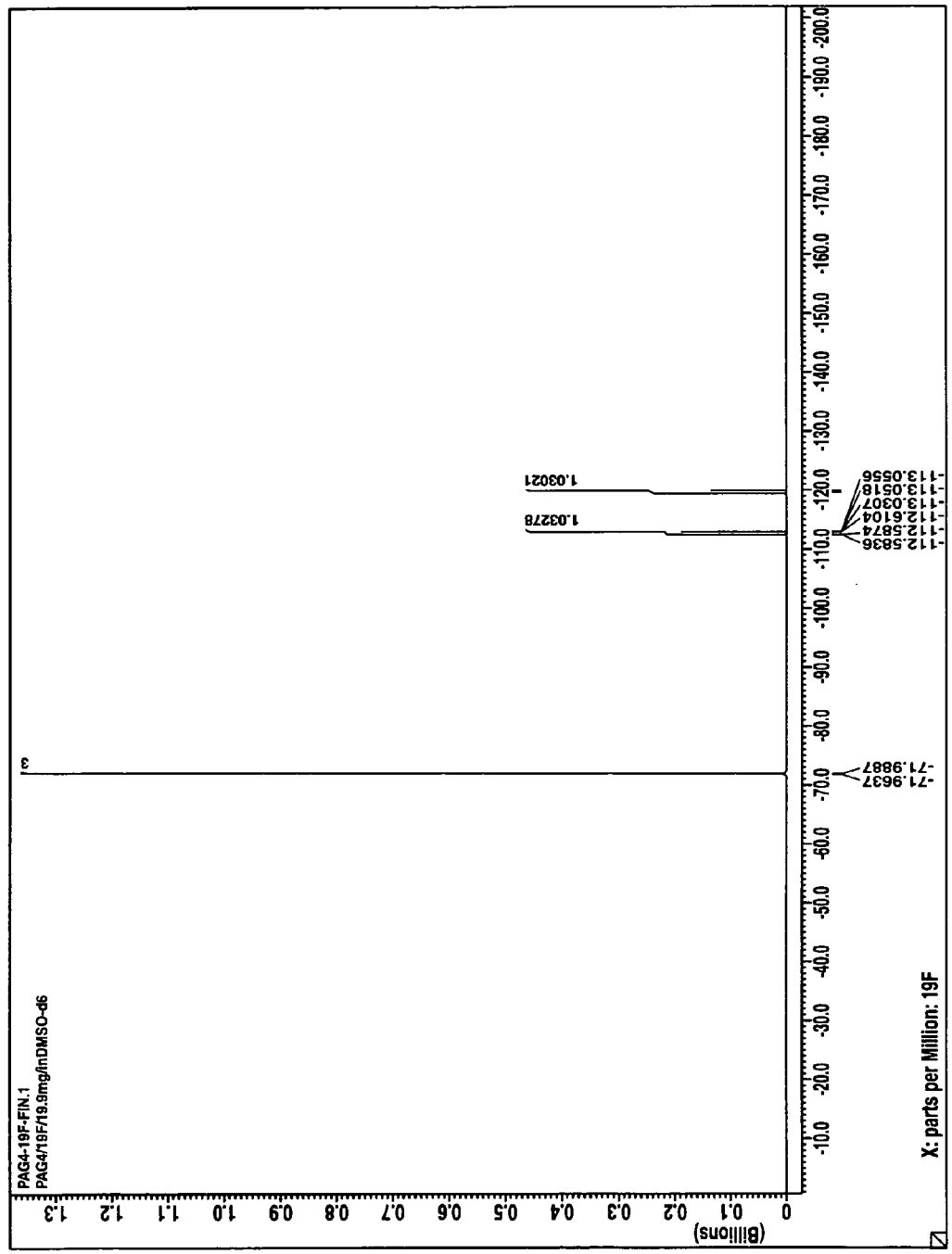
FIG. 10 is a diagram showing the $^{19}$F-NMR/DMSO-d$_6$ spectrum of PAG4 in Synthesis Example 14.

They were analyzed by spectroscopy. The NMR spectra ($^1$H-NMR and $^{19}$F-NMR/DMSO-d$_6$) of PAG3 are shown in FIGS. 7 and 8. The NMR spectra ($^1$H-NMR and $^{19}$F-NMR/DMSO-d$_6$) of PAG4 are shown in FIGS. 9 and 10.

PAG 3

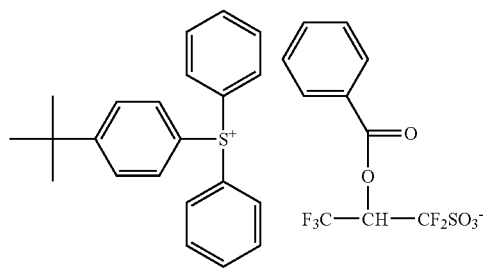

PAG 4

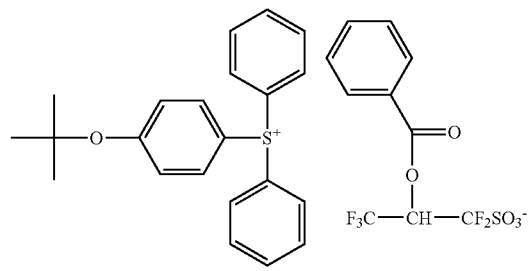

PAG 5

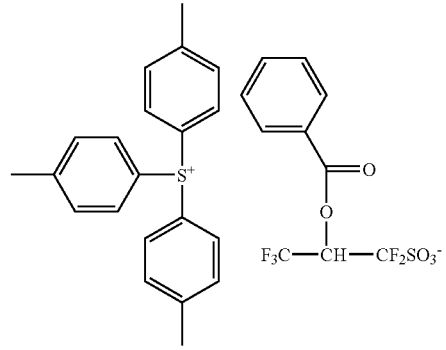

PAG 6

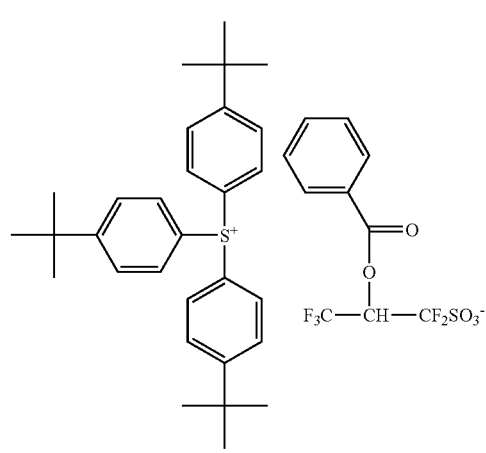

PAG 7

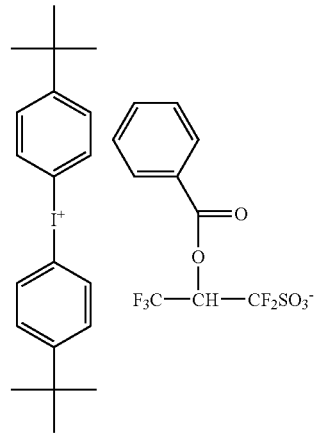

PAG 8
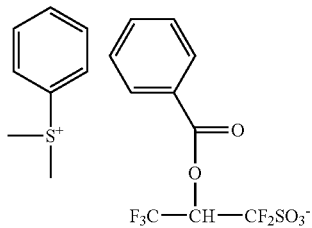
PAG 9
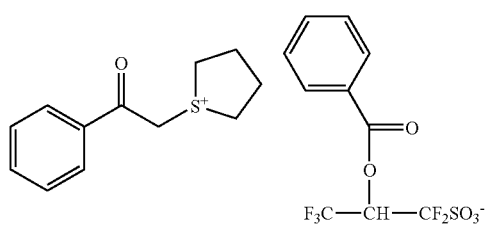
PAG 10
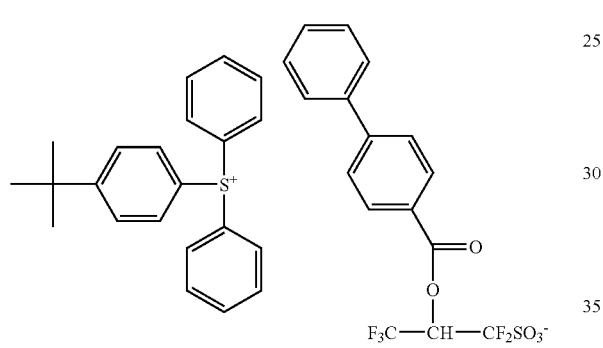
PAG 11
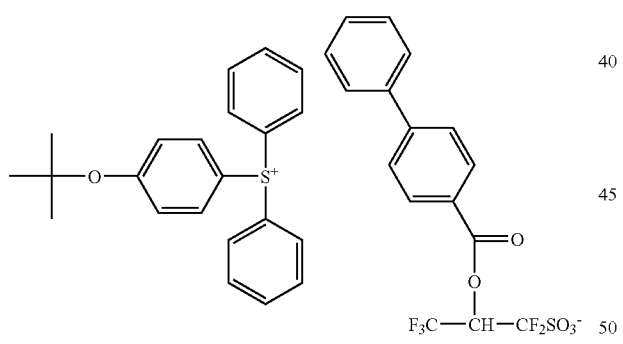
PAG 12
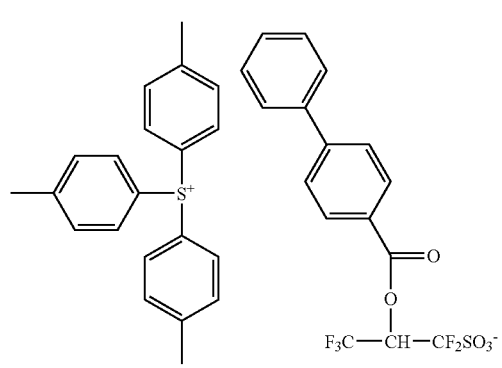
PAG 13
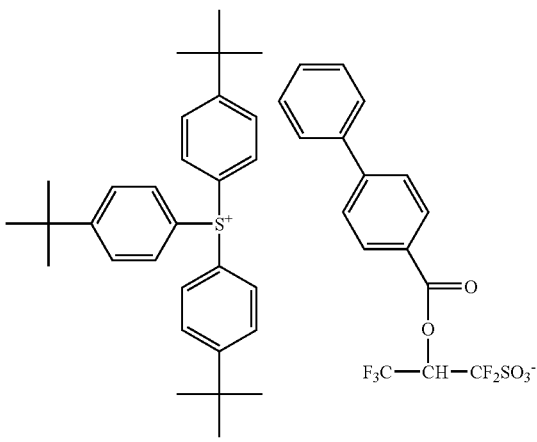
PAG 14
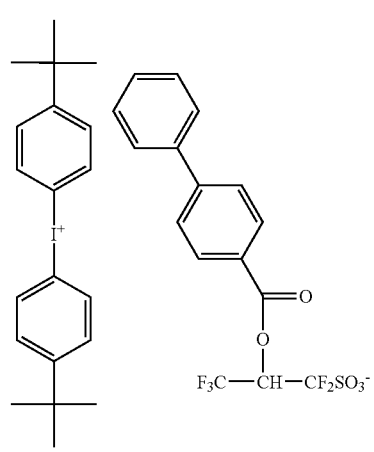
PAG 15
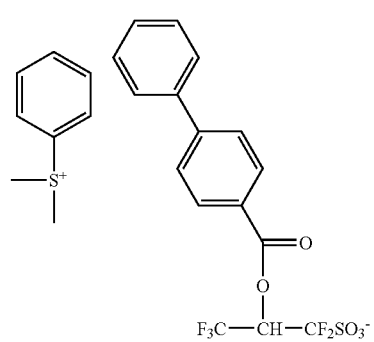
PAG 16
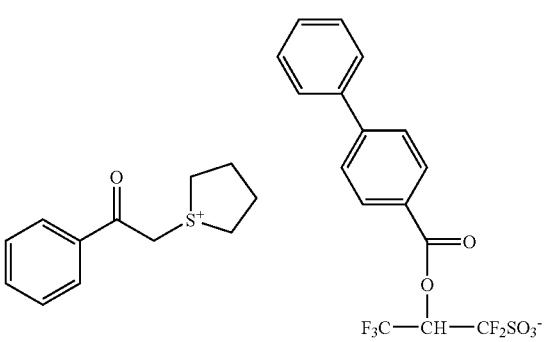

Synthesis Example 27

Synthesis of sodium 1,1,3,3,3-pentafluoro-2-(pivaloyloxy)-propanesulfonate (Anion 3)

The target sodium sulfonate was obtained by following the procedure of Synthesis Example 9 aside from using 1,1,3,3,3-pentafluoropropen-2-yl-pivaloate which had been synthesized by a conventional technique.

Figure 11:
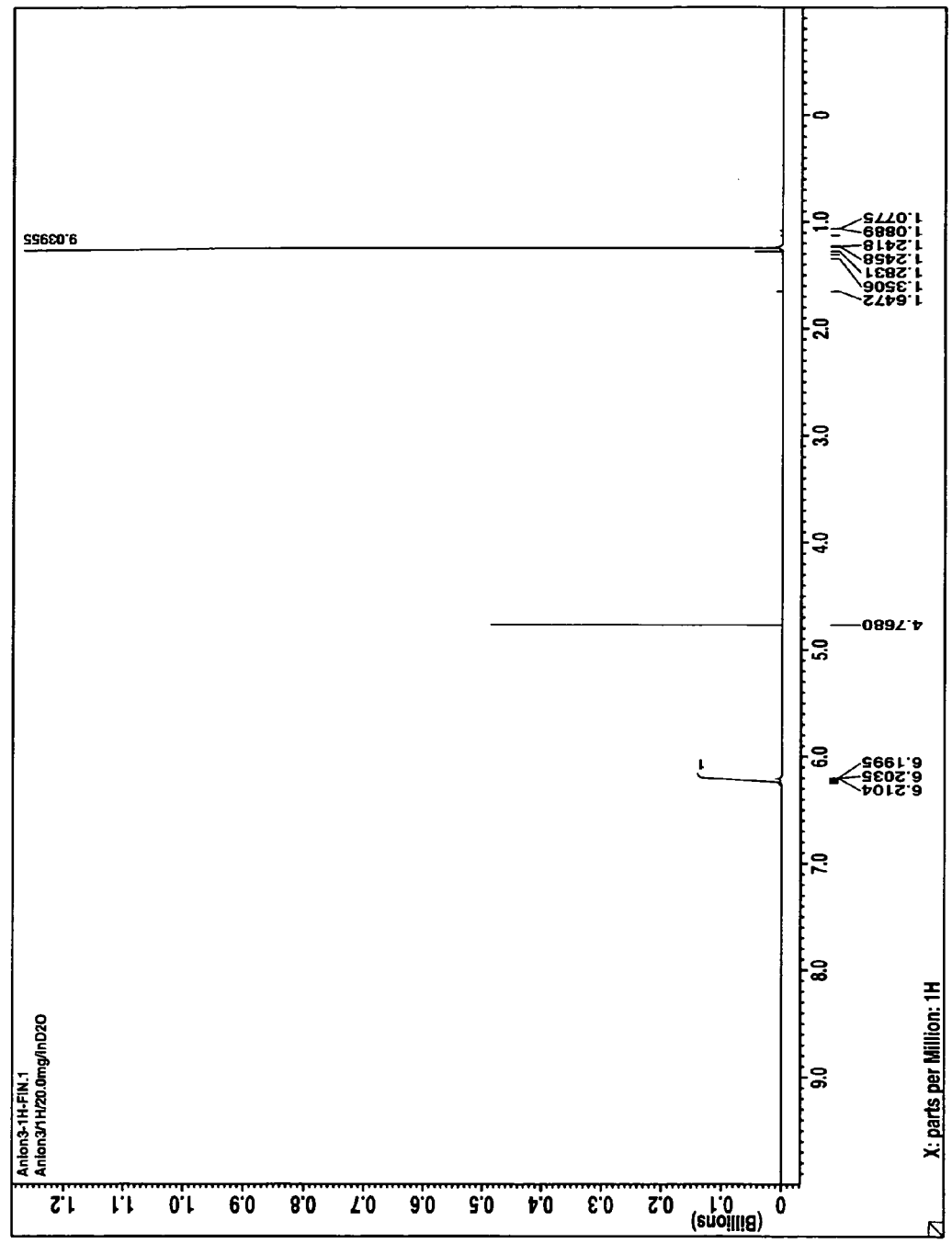
FIG. 11 is a diagram showing the $^1$H-NMR/D$_2$O spectrum of Anion 3 in Synthesis Example 27.
Figure 12:
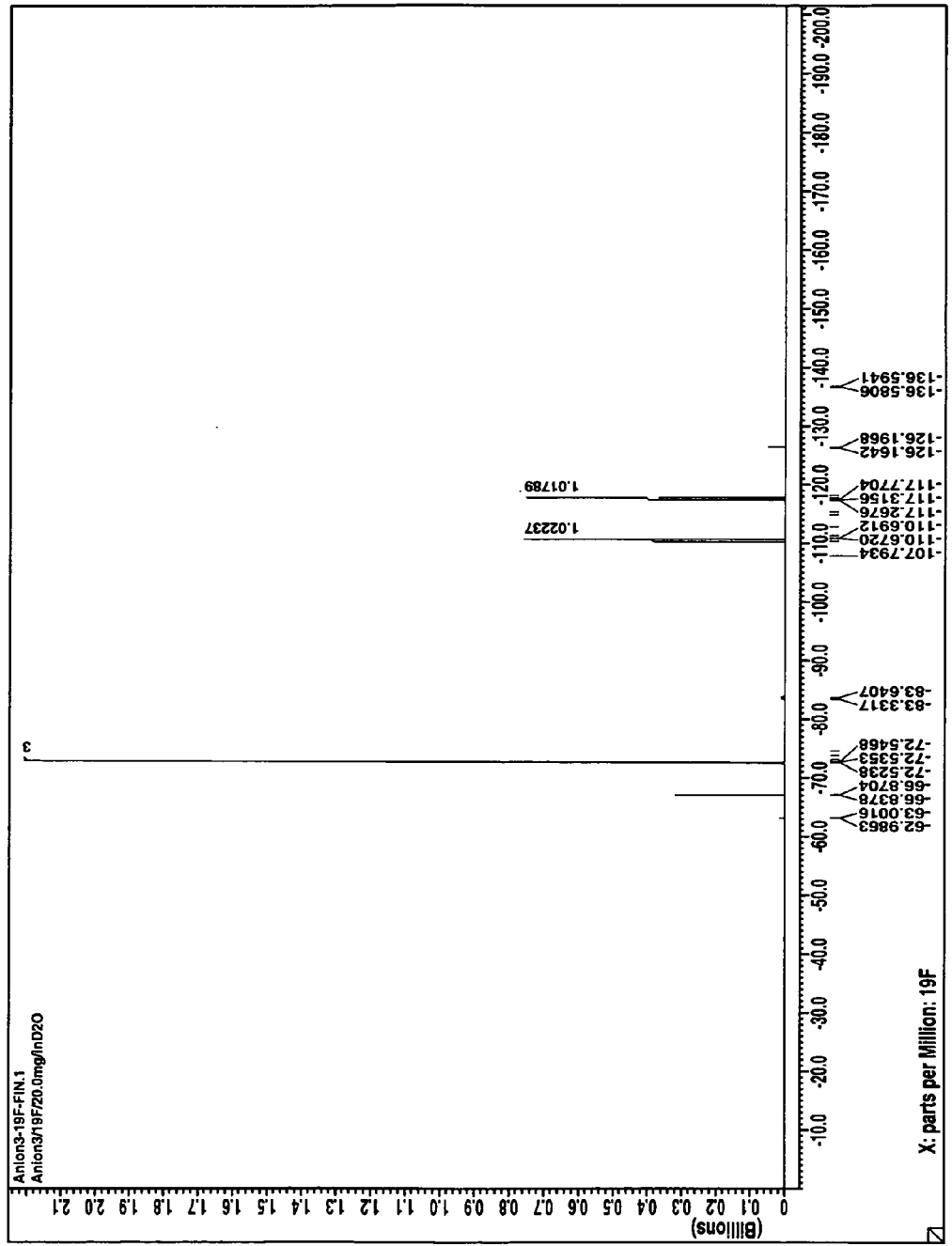
FIG. 12 is a diagram showing the $^{19}$F-NMR/D$_2$O spectrum of Anion 3 in Synthesis Example 27.

The target compound was analyzed by spectroscopy. The data of IR spectroscopy are shown below. The NMR spectra ($^1$H-NMR and $^{19}$F-NMR/D$_2$O) are shown in FIGS. 11 and 12.

Infrared absorption spectra (IR; KBr disc, cm$^{-1}$) 1749, 1367, 1338, 1297, 1268, 1241, 1203, 1168, 1135, 1085, 998, 921, 838, 647, 628, 572

Time-of-flight mass spectrometry (TOFMS; MALDI) NEGATIVE M$^-$313 (corresponding to CF$_3$CH(OCOC$_4$H$_9$)CF$_2$SO$_3^-$)

Synthesis Example 28

Synthesis of sodium 1,1,3,3,3-pentafluoro-2-(cyclohexane-carbonyloxy)propanesulfonate (Anion 4)

The target sodium sulfonate was obtained by following the procedure of Synthesis Example 9 aside from using 1,1,3,3,3-pentafluoropropen-2-yl-cyclohexanecarboxylate which had been synthesized by a conventional technique.

Figure 13:
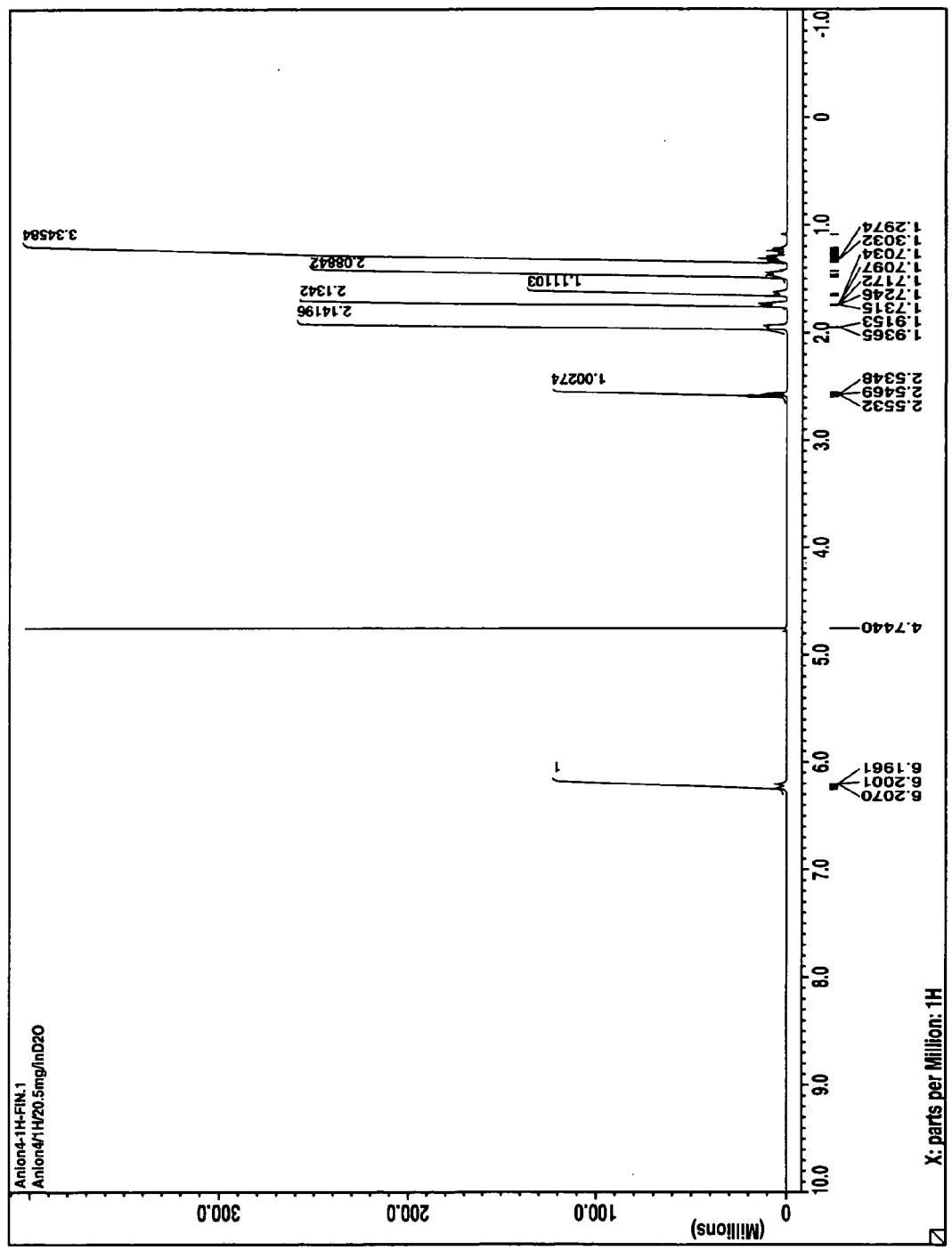
FIG. 13 is a diagram showing the $^1$H-NMR/D$_2$O spectrum of Anion 4 in Synthesis Example 28.
Figure 14:
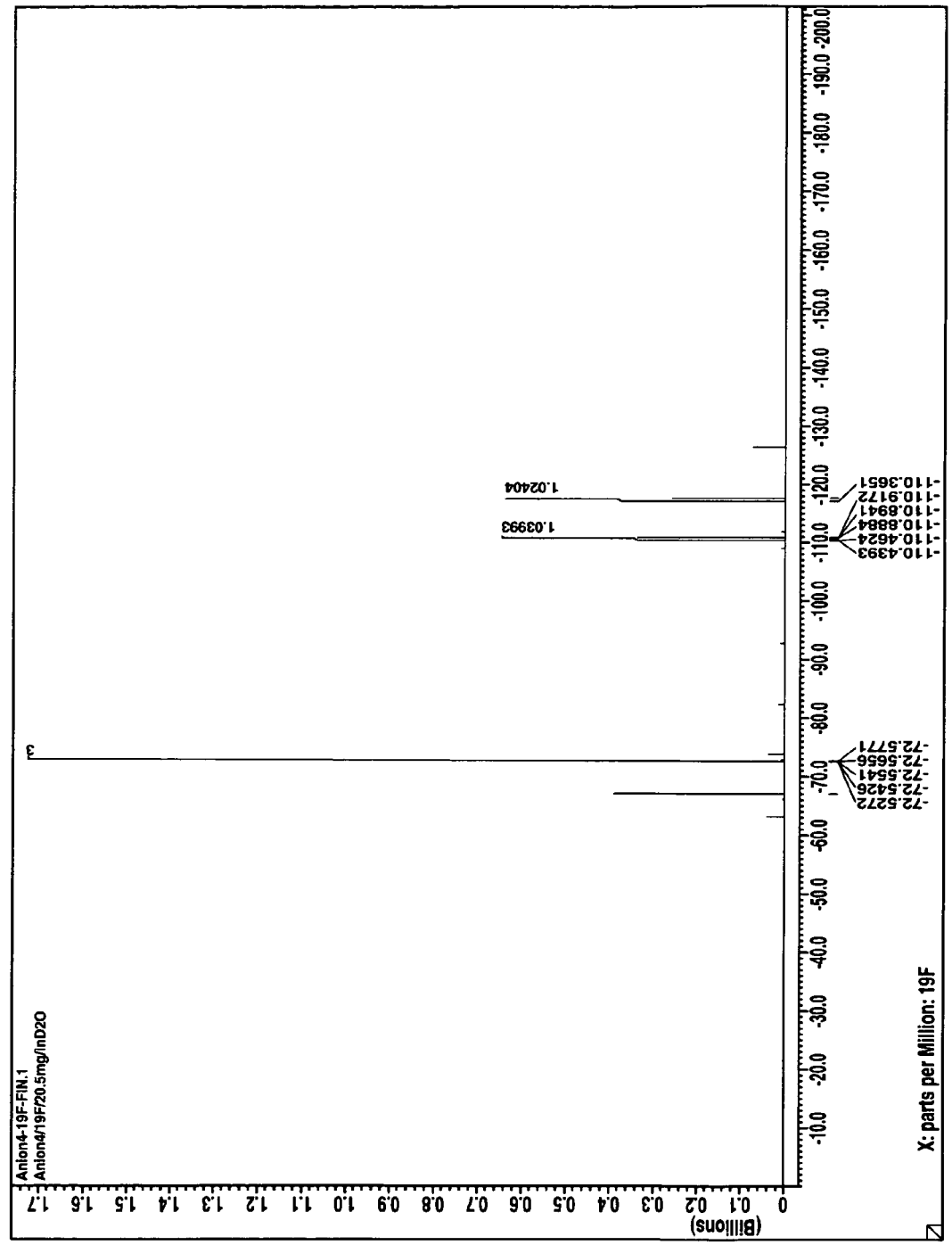
FIG. 14 is a diagram showing the $^{19}$F-NMR/D$_2$O spectrum of Anion 4 in Synthesis Example 28.

The target compound was analyzed by spectroscopy. The data of IR spectroscopy are shown below. The NMR spectra ($^1$H-NMR and $^{19}$F-NMR/D$_2$O) are shown in FIGS. 13 and 14.

Infrared absorption spectra (IR; KBr disc, cm$^{-1}$) 1749, 1375, 1342, 1286, 1270, 1245, 1222, 1199, 1172, 1159, 1133, 1083, 1070, 1008, 1000, 943, 833, 647

Time-of-flight mass spectrometry (TOFMS; MALDI) NEGATIVE M$^-$339 (corresponding to CF$_3$CH(OCOC$_6$H$_{11}$)CF$_2$SO$_3^-$)

Synthesis Example 29

Synthesis of sodium 1,1,3,3,3-pentafluoro-2-(2-furoyloxy)-propanesulfonate (Anion 5)

The target sodium sulfonate was obtained by following the procedure of Synthesis Example 9 aside from using 1,1,3,3,3-pentafluoropropen-2-yl-furanyl-2-carboxylate which had been synthesized by a conventional technique.

Figure 15:
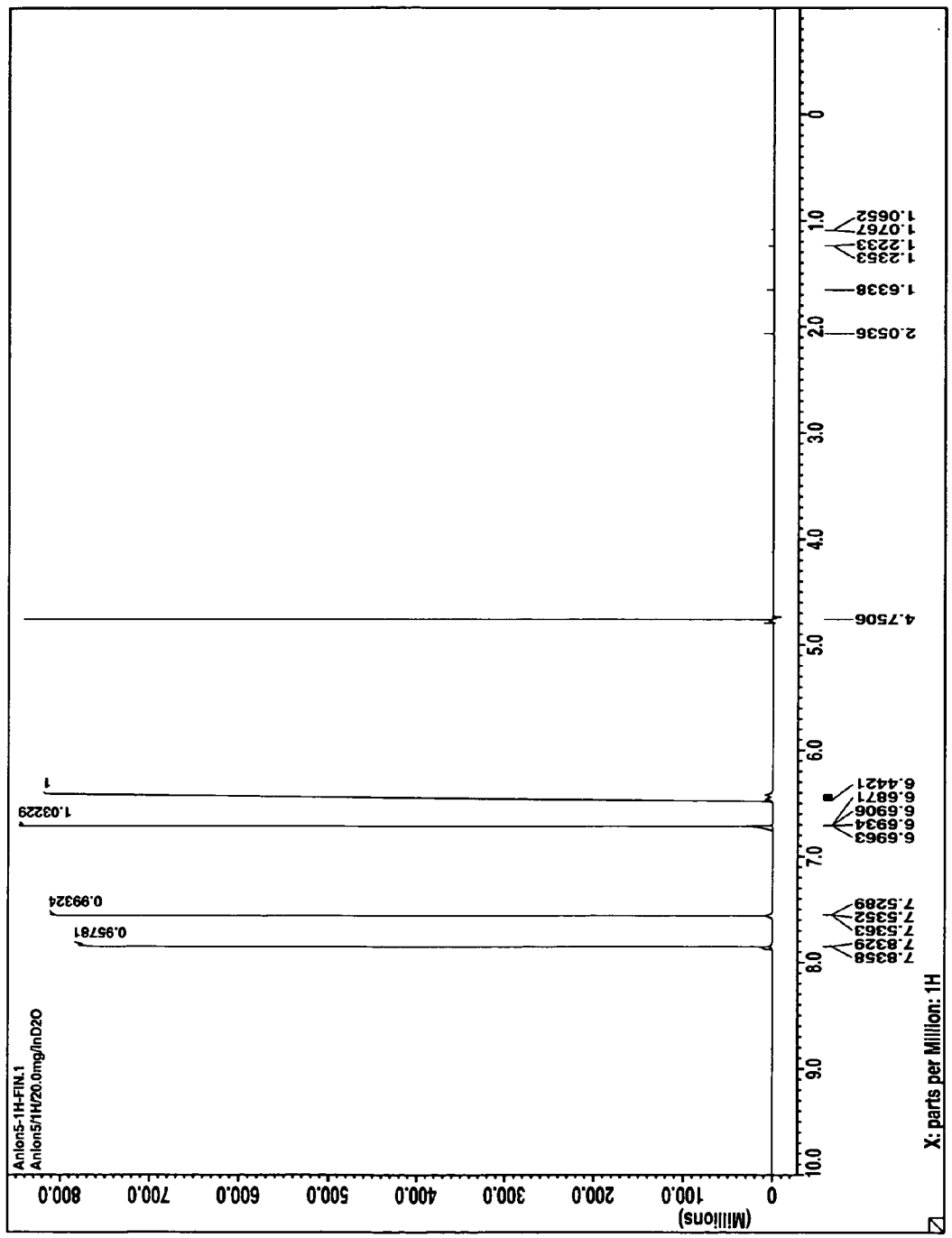
FIG. 15 is a diagram showing the $^1$H-NMR/D$_2$O spectrum of Anion 5 in Synthesis Example 29.
Figure 16:
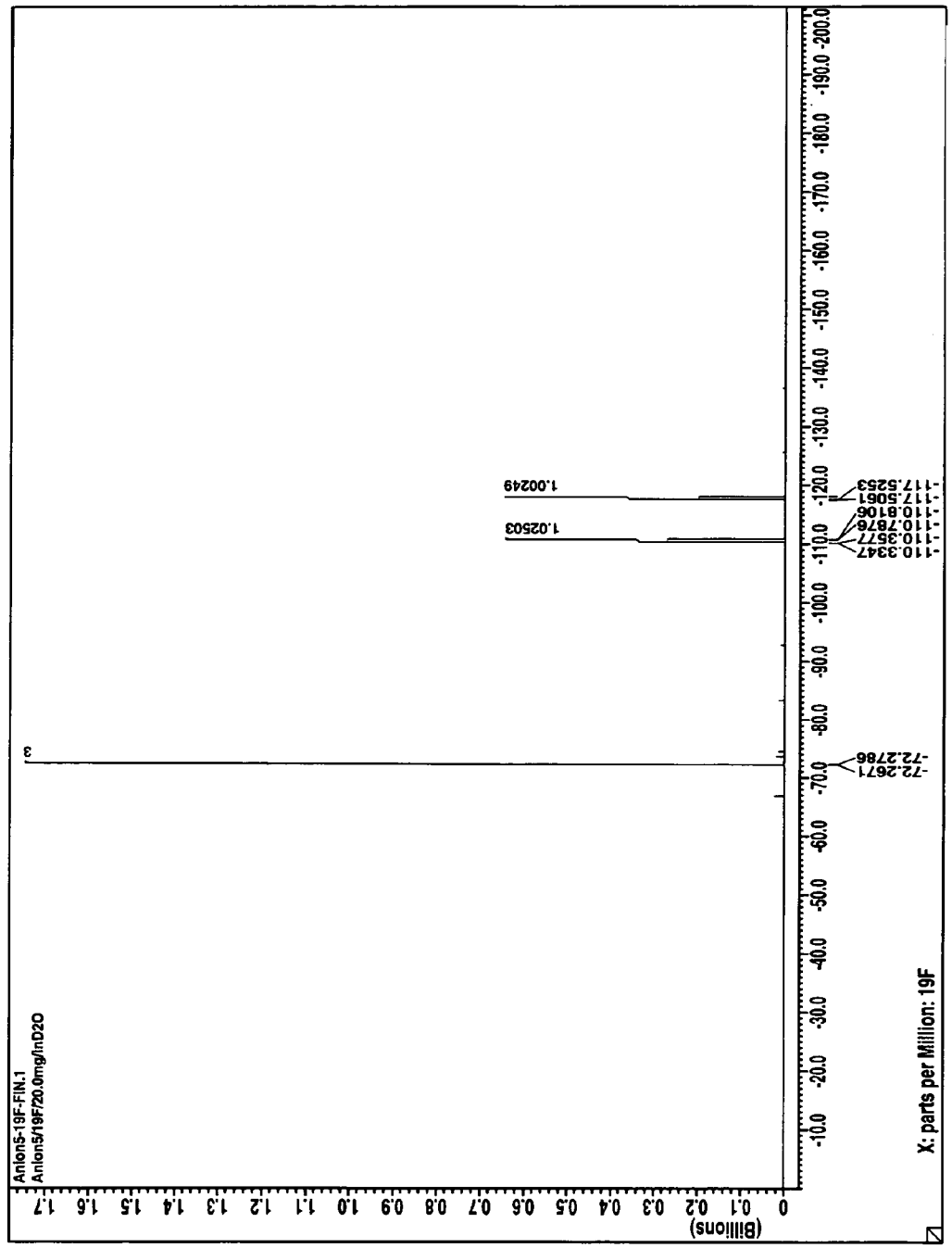
FIG. 16 is a diagram showing the $^{19}$F-NMR/D$_2$O spectrum of Anion 5 in Synthesis Example 29.

The target compound was analyzed by spectroscopy. The data of IR spectroscopy are shown below. The NMR spectra ($^1$H-NMR and $^{19}$F-NMR/D$_2$O) are shown in FIGS. 15 and 16.

Infrared absorption spectra (IR; KBr disc, cm$^{-1}$) 1743, 1720, 1575, 1471, 1400, 1367, 1346, 1321, 1305, 1272, 1243, 1197, 1168, 1130, 1083, 1016, 1006, 933, 892, 779, 750, 651

Time-of-flight mass spectrometry (TOFMS; MALDI) NEGATIVE M$^-$323 (corresponding to CF$_3$CH(OCOC$_4$H$_3$O)CF$_2$SO$_3^-$)

Synthesis Example 30

Synthesis of sodium 1,1,3,3,3-pentafluoro-2-(2-naphthoyloxy)propanesulfonate (Anion 6)

The target sodium sulfonate was obtained by following the procedure of Synthesis Example 9 aside from using 1,1,3,3,3-pentafluoropropen-2-yl-naphthalene-2-carboxylate which had been synthesized by a conventional technique.

Figure 17:
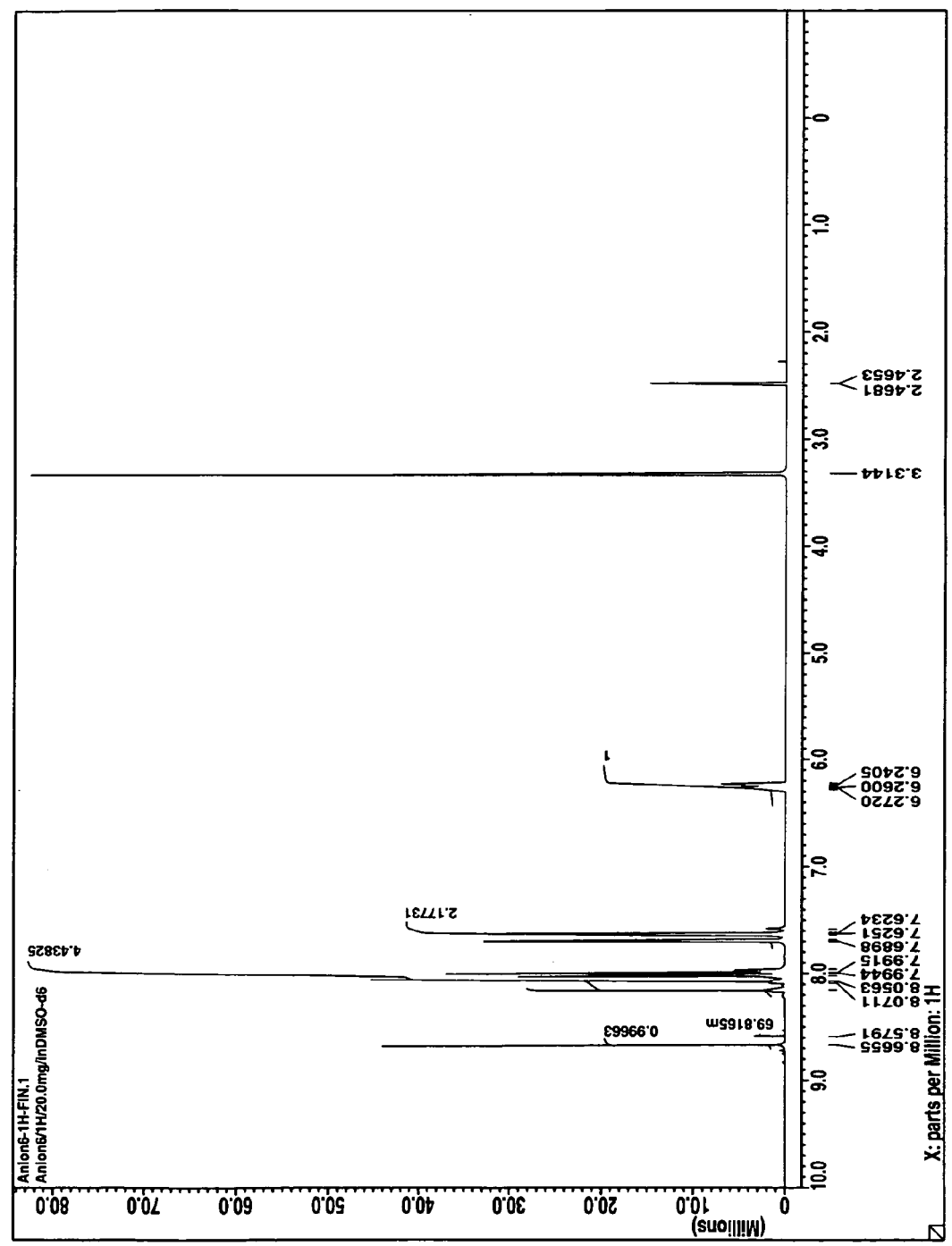
FIG. 17 is a diagram showing the $^1$H-NMR/DMSO-d$_6$ spectrum of Anion 6 in Synthesis Example 30.
Figure 18:
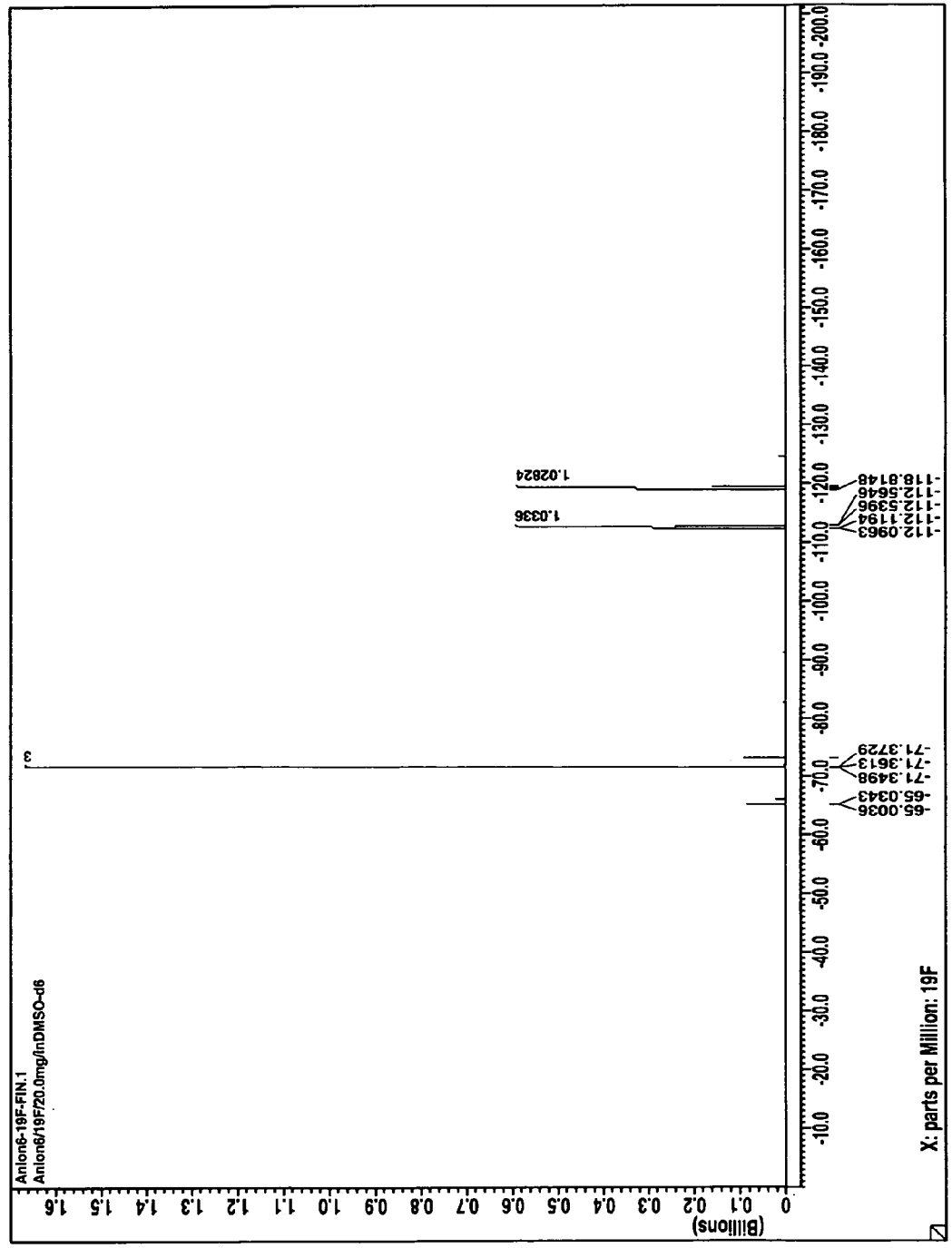
FIG. 18 is a diagram showing the $^{19}$F-NMR/DMSO-d$_6$ spectrum of Anion 6 in Synthesis Example 30.

The target compound was analyzed by spectroscopy. The data of IR spectroscopy are shown below. The NMR spectra ($^1$H-NMR and $^{19}$F-NMR/DMSO-d$_6$) are shown in FIGS. 17 and 18.

Infrared absorption spectra (IR; KBr disc, cm$^{-1}$) 1745, 1365, 1344, 1288, 1261, 1238, 1195, 1164, 1130, 1105, 773, 759, 649

Time-of-flight mass spectrometry (TOFMS; MALDI) NEGATIVE M$^-$389 (corresponding to CF$_3$CH(OCOC$_{10}$H$_{15}$)CF$_2$SO$_3^-$)

Synthesis Example 31

Synthesis of sodium 1,1,3,3,3-pentafluoro-2-(4-tert-butylbenzoyloxy)propanesulfonate (Anion 7)

The target sodium sulfonate was obtained by following the procedure of Synthesis Example 9 aside from using 1,1,3,3,3-pentafluoropropen-2-yl-(4-tert-butyl)benzoate which had been synthesized by a conventional technique.

Figure 19:
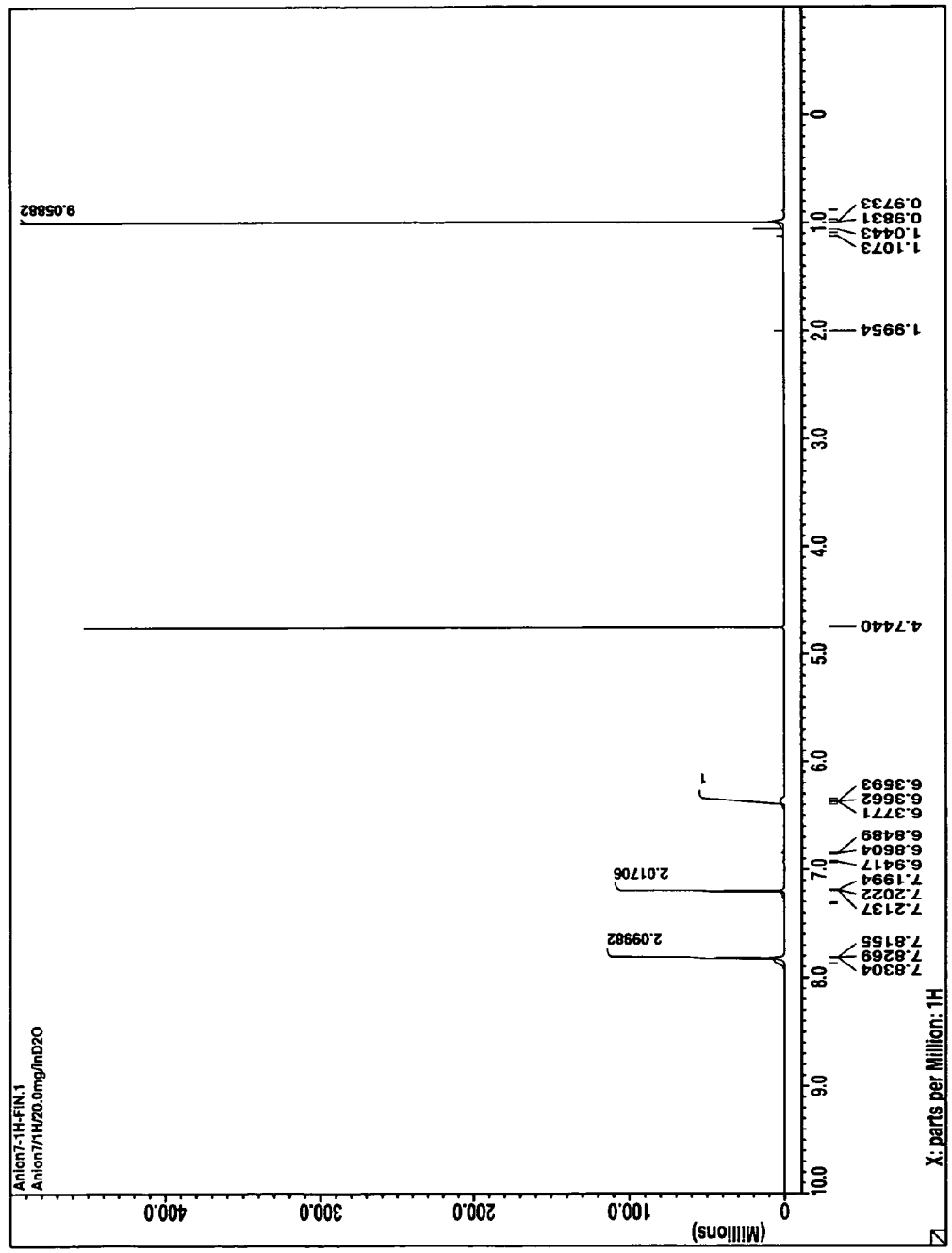
FIG. 19 is a diagram showing the $^1$H-NMR/D$_2$O spectrum of Anion 7 in Synthesis Example 31.
Figure 20:
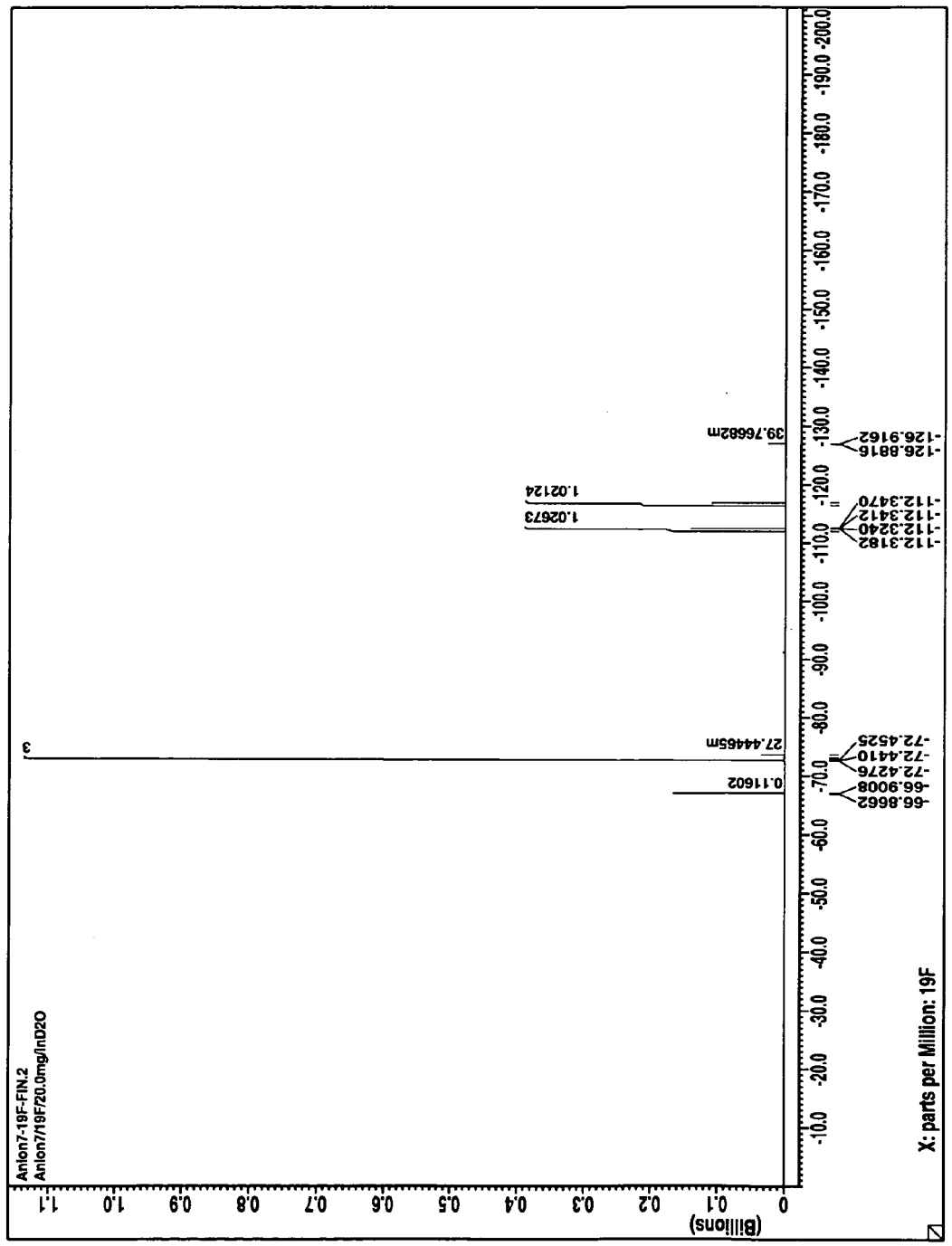
FIG. 20 is a diagram showing the $^{19}$F-NMR/D$_2$O spectrum of Anion 7 in Synthesis Example 31.
Figure 21:
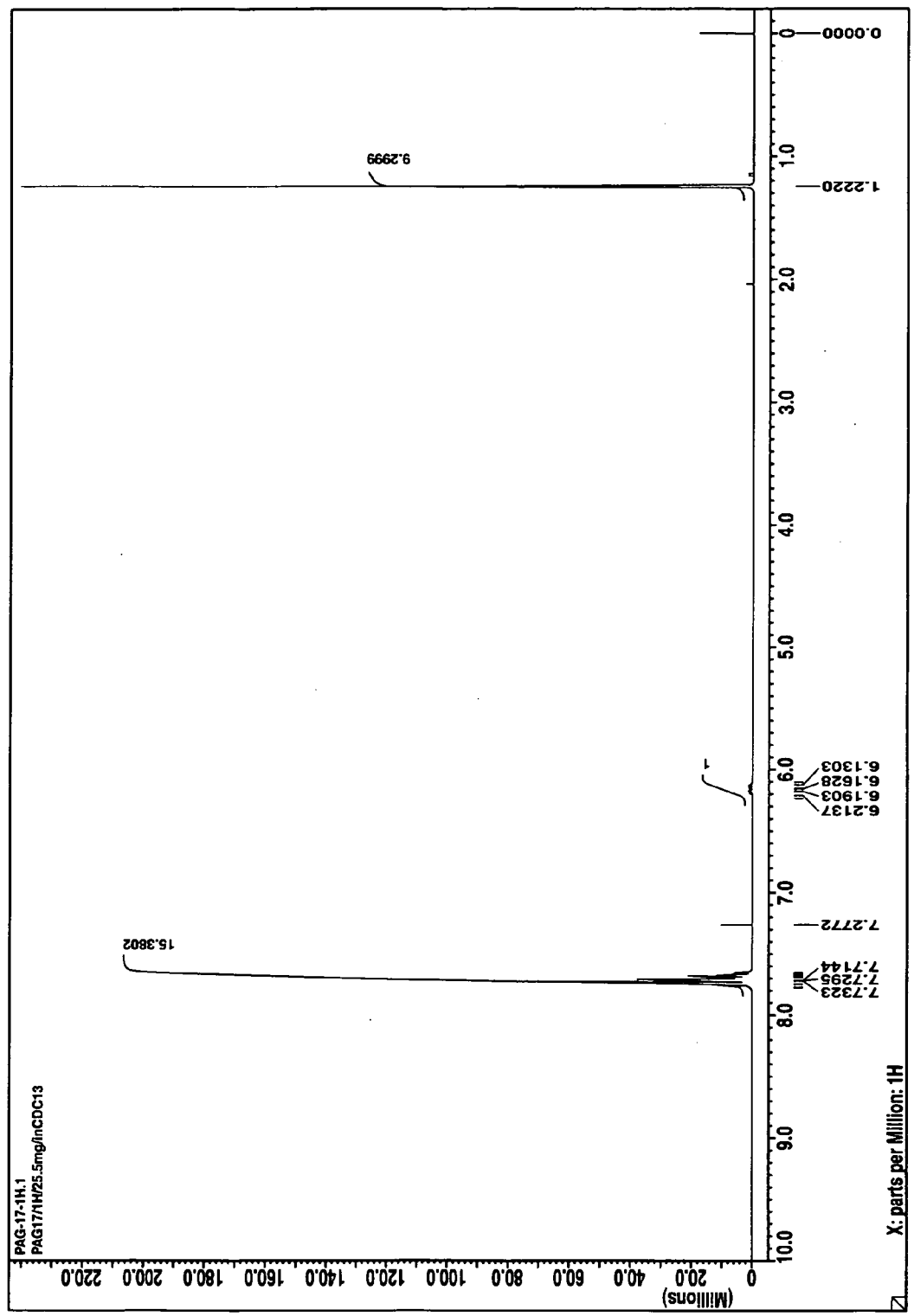
FIG. 21 is a diagram showing the $^1$H-NMR/CDCl$_3$ spectrum of PAG17 in Synthesis Example 33.
Figure 22:
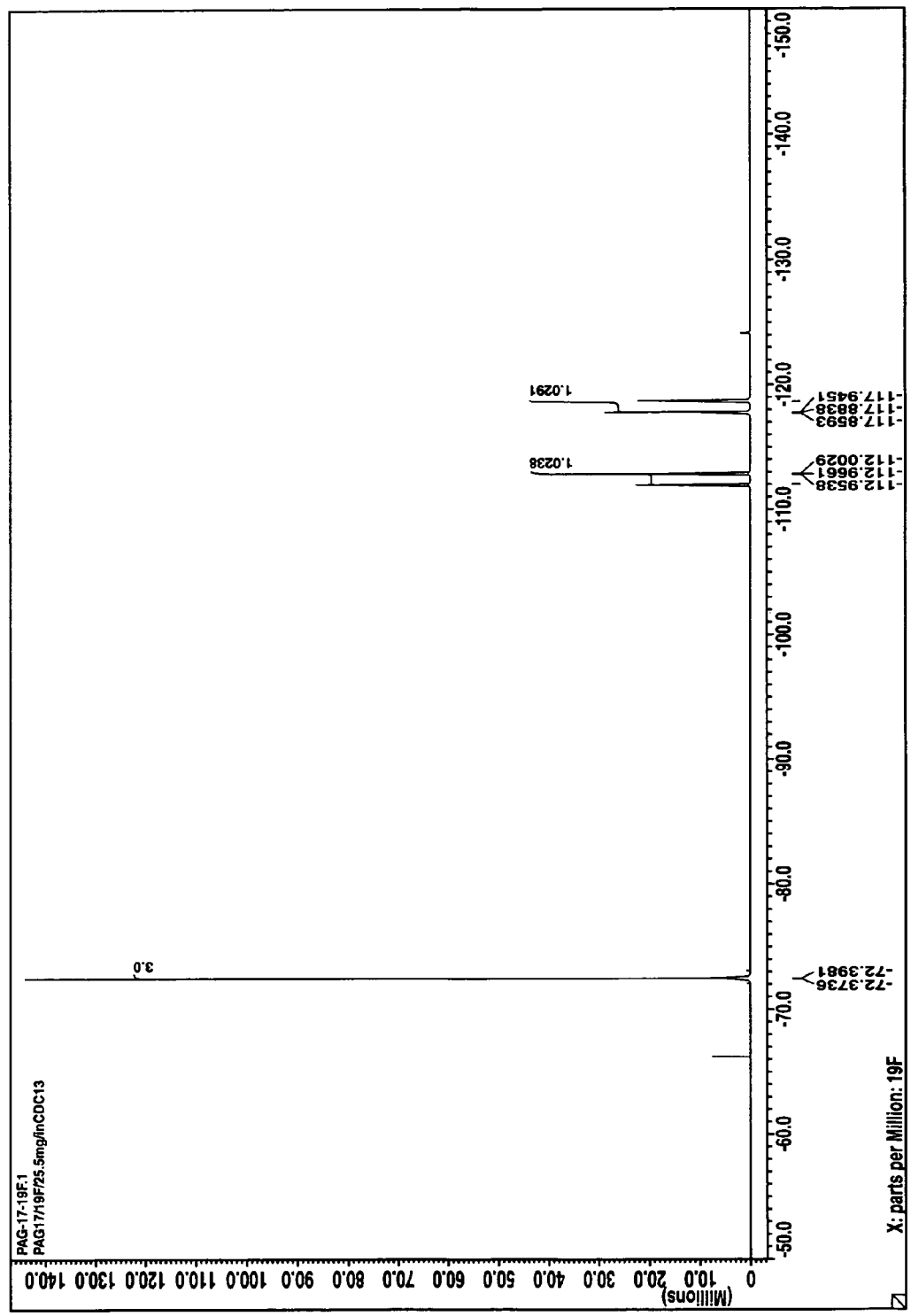
FIG. 22 is a diagram showing the $^{19}$F-NMR/CDCl$_3$ spectrum of PAG17 in Synthesis Example 33.
Figure 23:
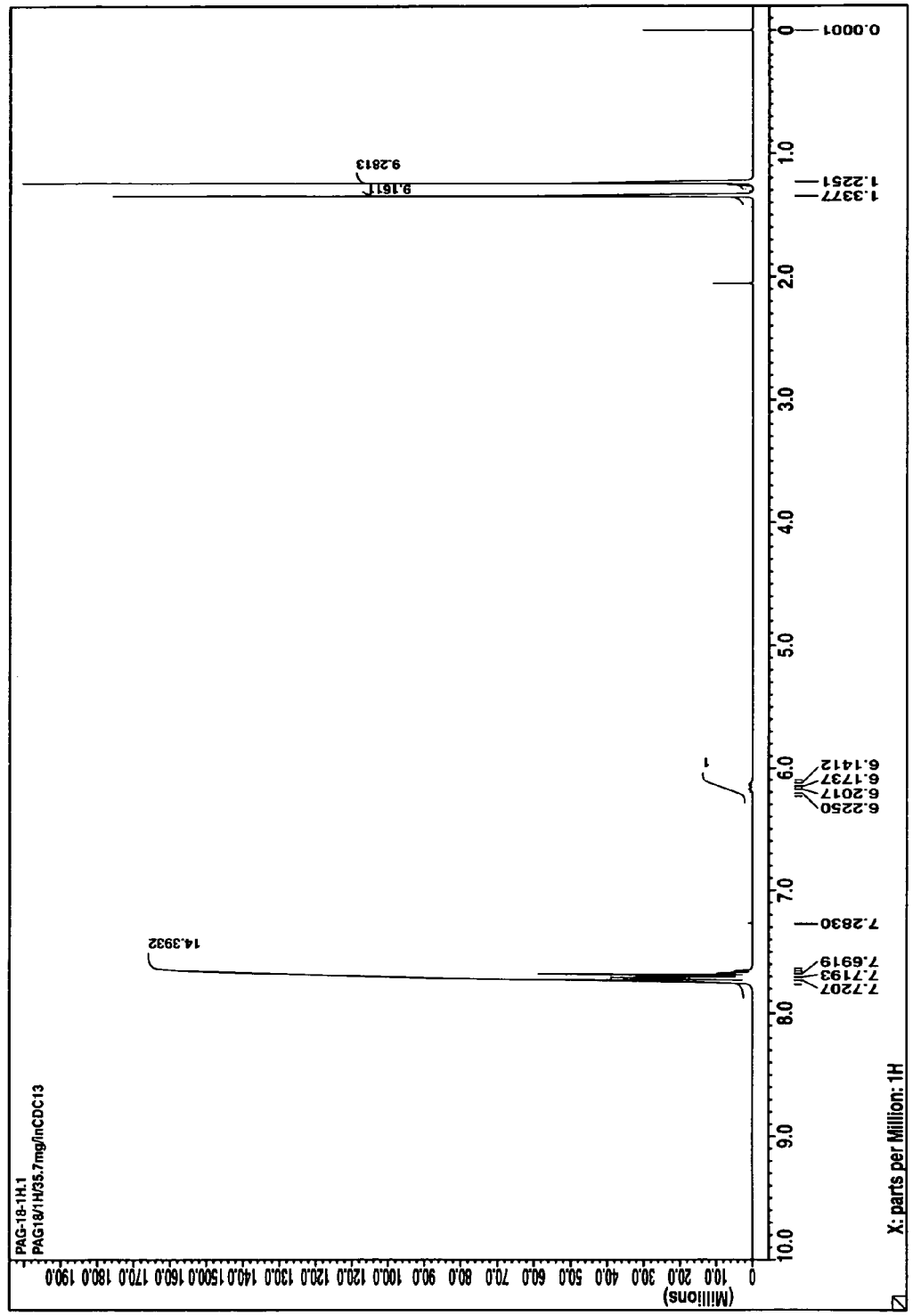
FIG. 23 is a diagram showing the $^1$H-NMR/CDCl$_3$ spectrum of PAG18 in Synthesis Example 34.
Figure 24:
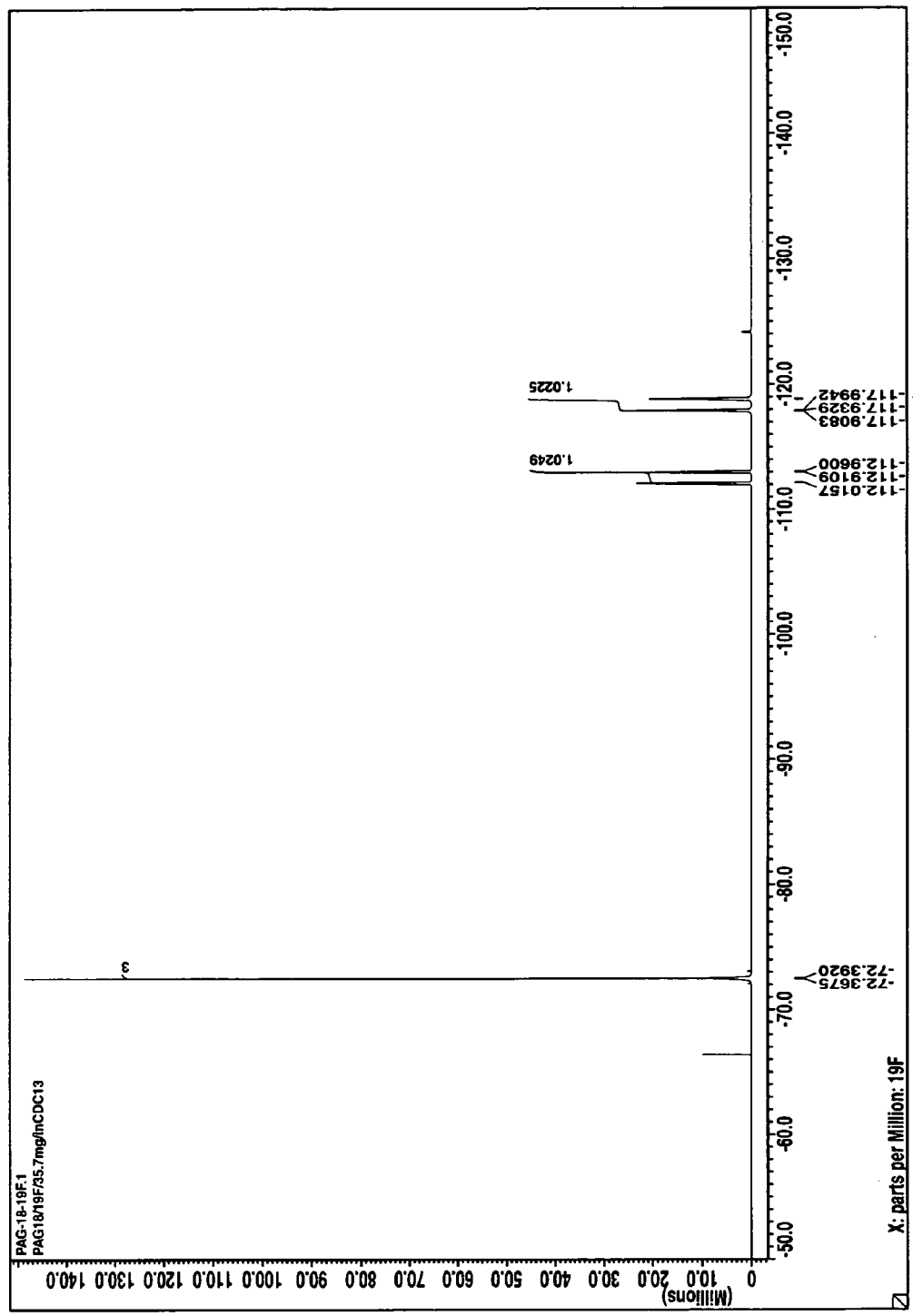
FIG. 24 is a diagram showing the $^{19}$F-NMR/CDCl$_3$ spectrum of PAG18 in Synthesis Example 34.
Figure 25:
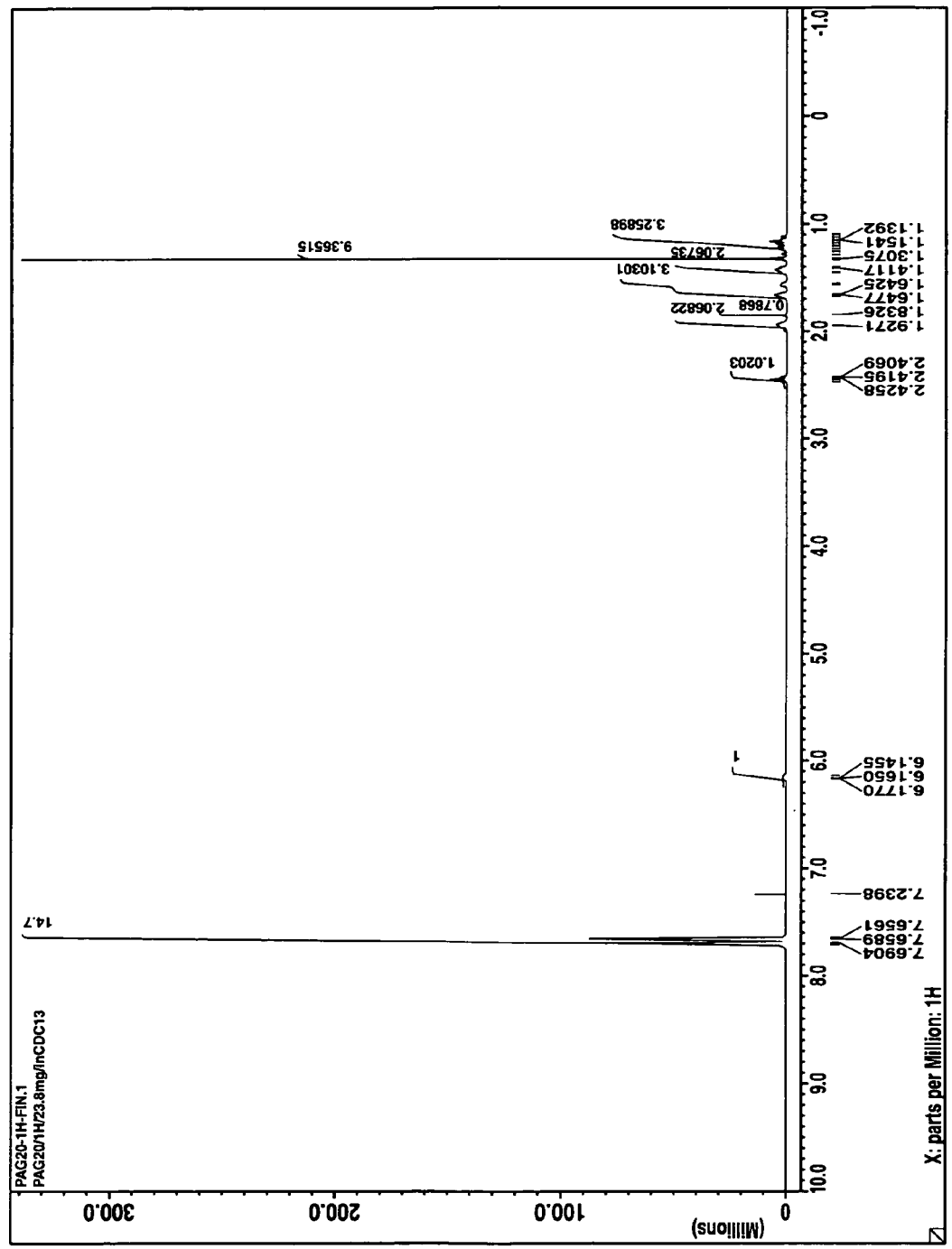
FIG. 25 is a diagram showing the $^1$H-NMR/CDCl$_3$ spectrum of PAG20 in Synthesis Example 36.
Figure 26:
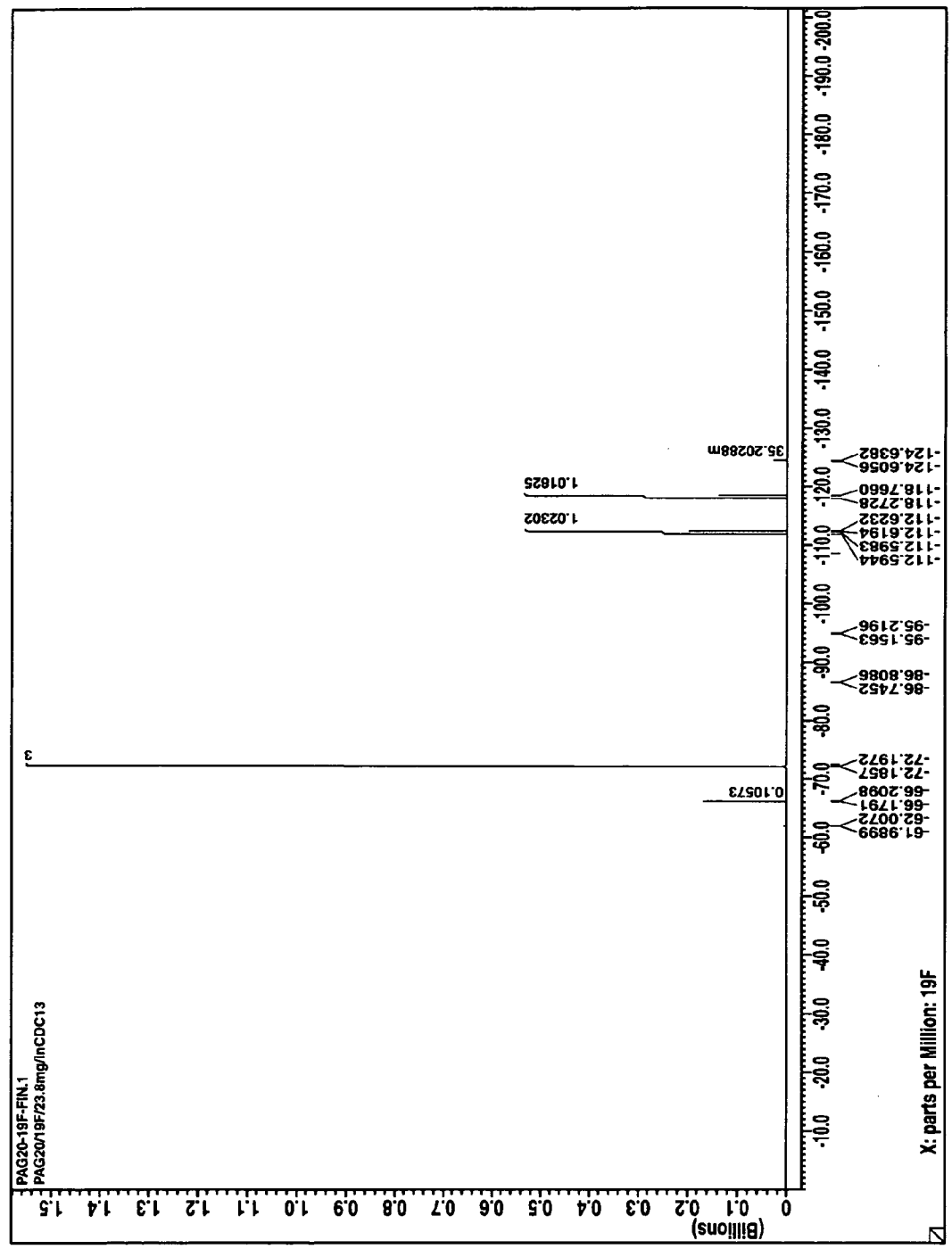
FIG. 26 is a diagram showing the $^{19}$F-NMR/CDCl$_3$ spectrum of PAG20 in Synthesis Example 36.
Figure 27:
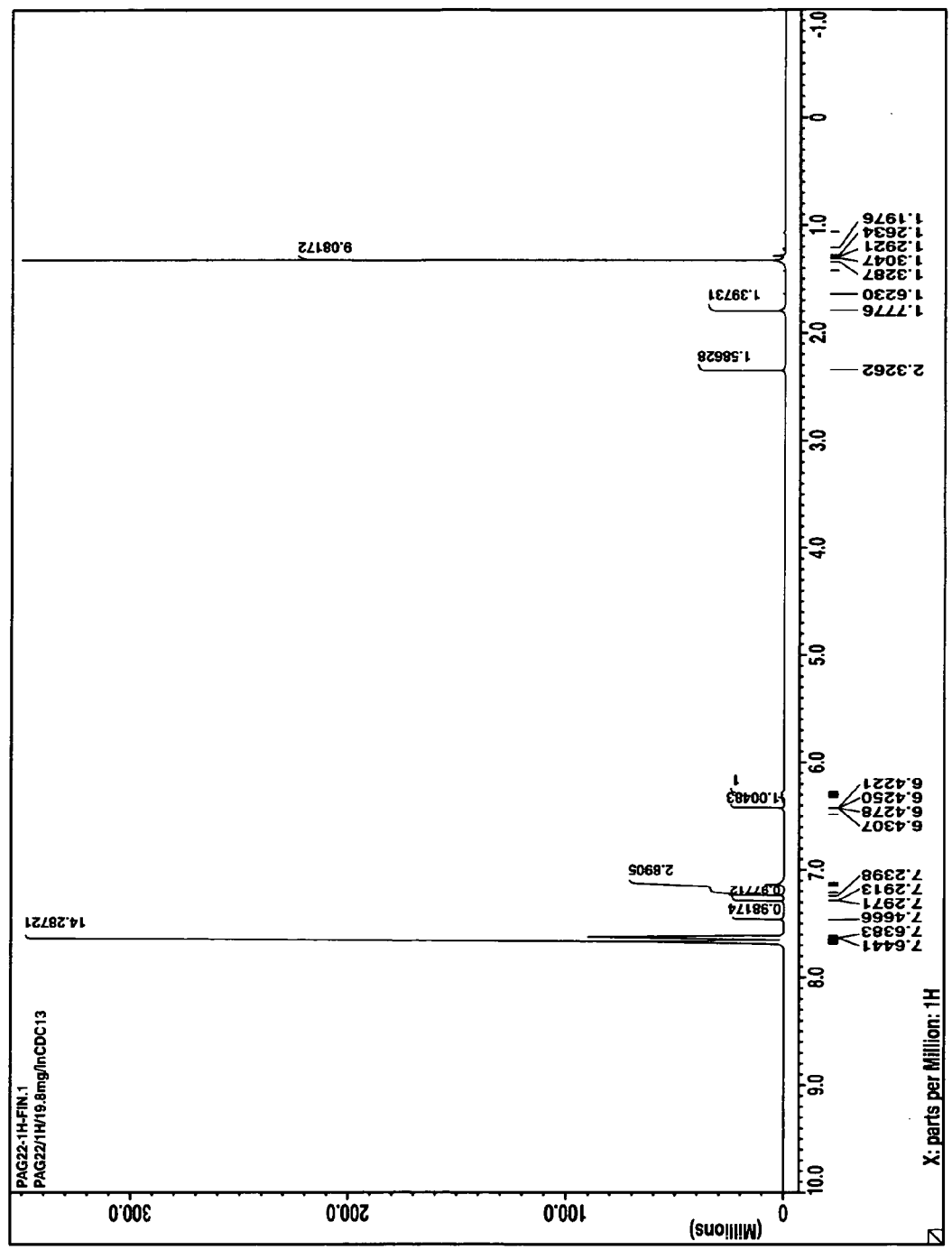
FIG. 27 is a diagram showing the $^1$H-NMR/CDCl$_3$ spectrum of PAG22 in Synthesis Example 38.
Figure 28:
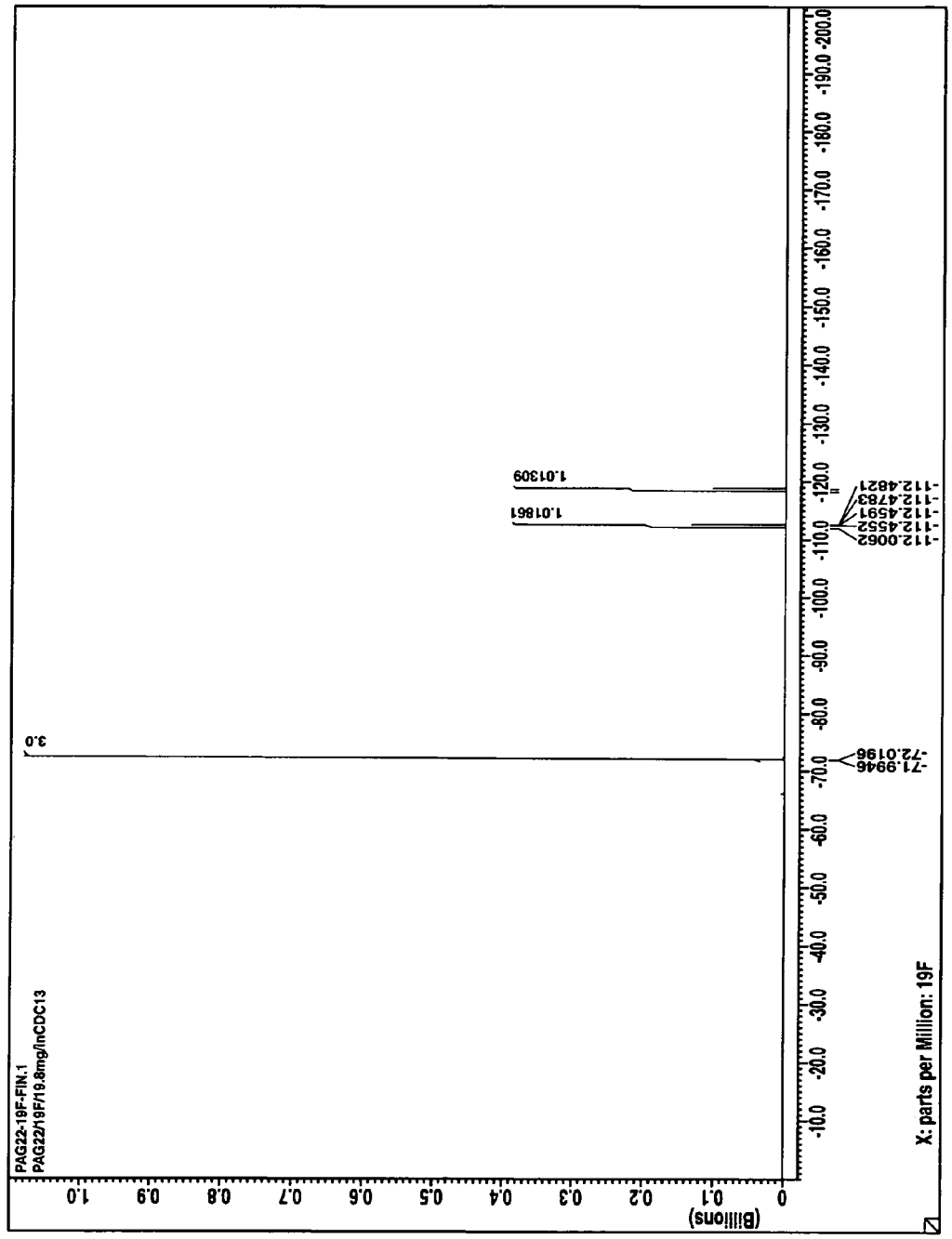
FIG. 28 is a diagram showing the $^{19}$F-NMR/CDCl$_3$ spectrum of PAG22 in Synthesis Example 38.
Figure 29:
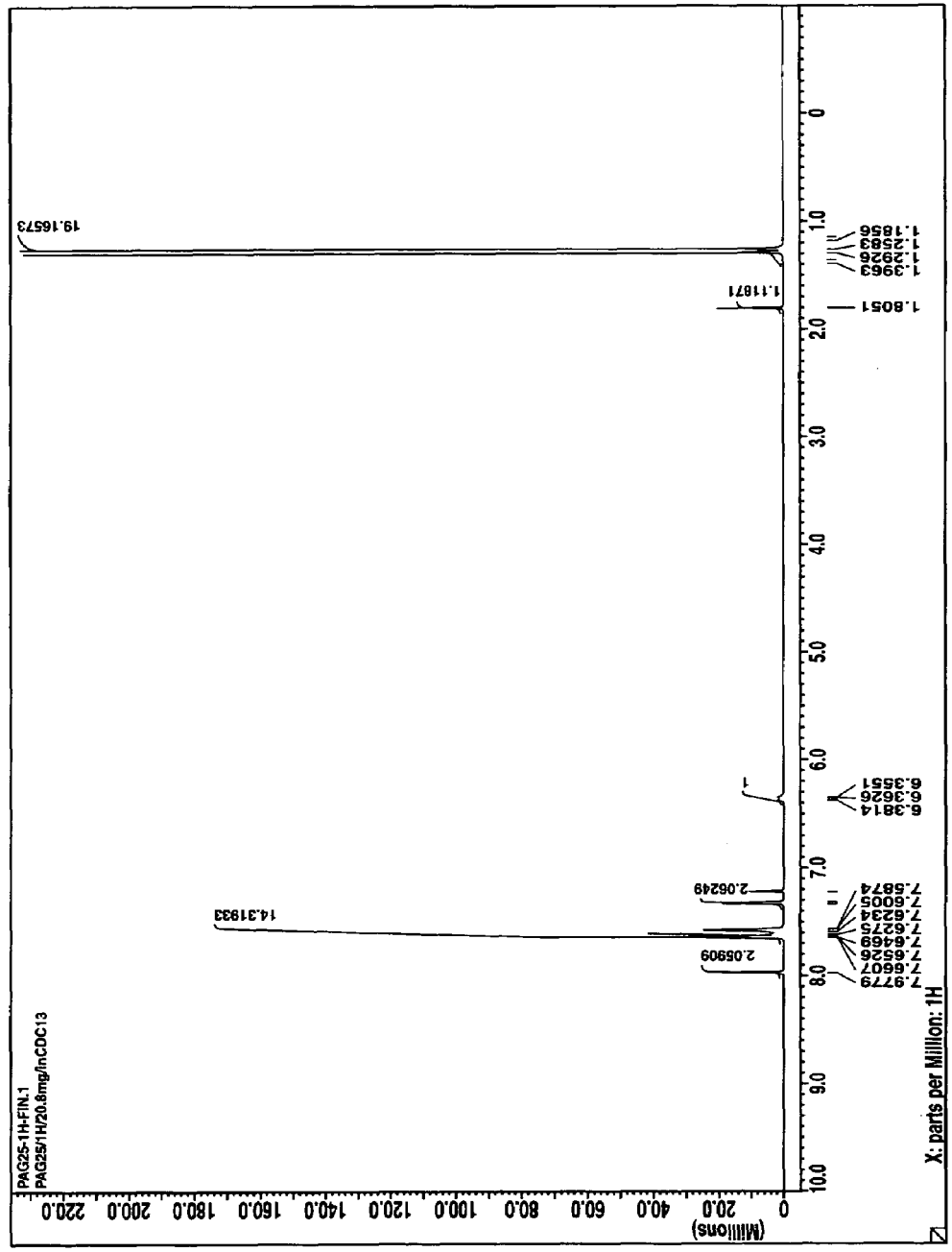
FIG. 29 is a diagram showing the $^1$H-NMR/CDCl$_3$ spectrum of PAG25 in Synthesis Example 41.
Figure 30:
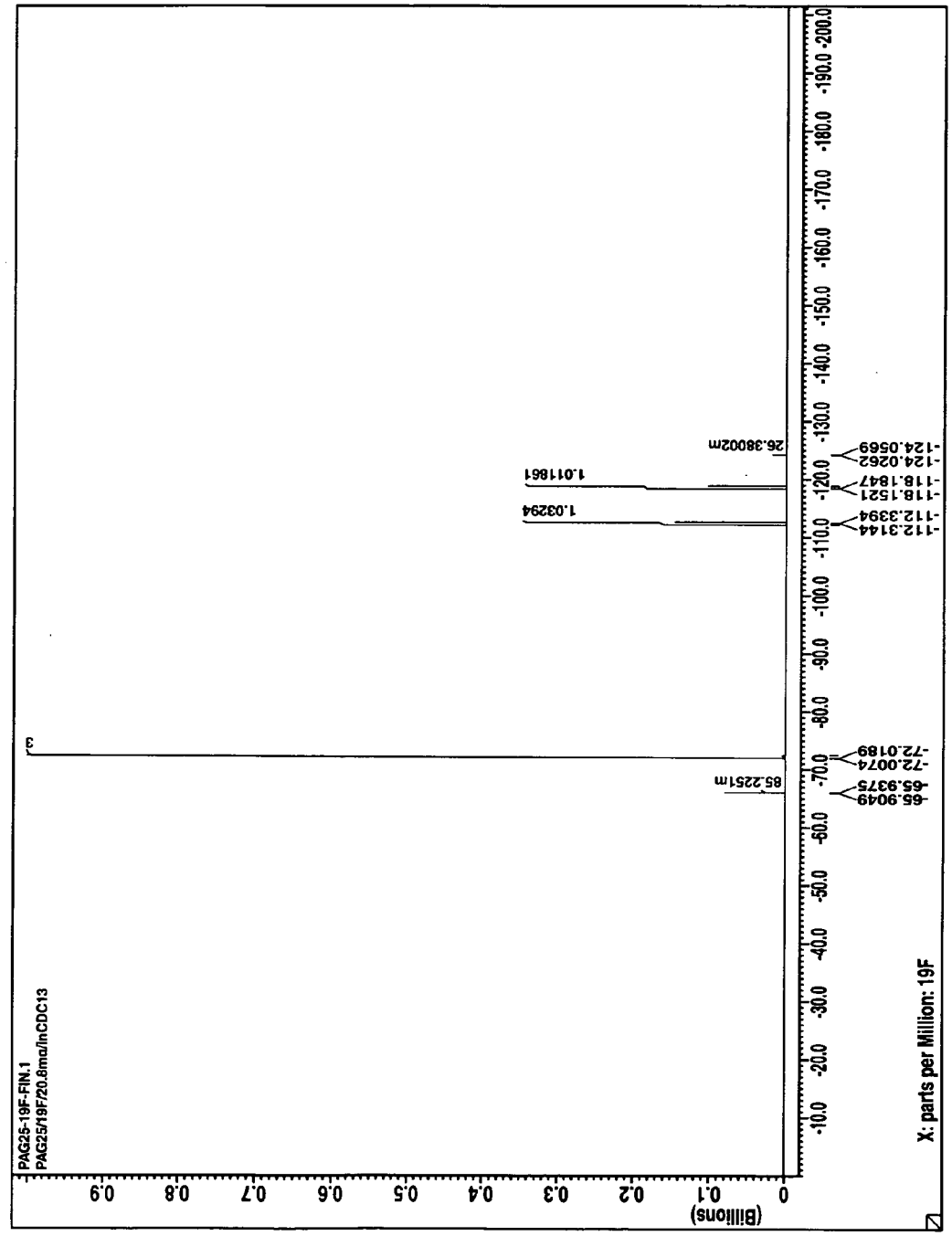
FIG. 30 is a diagram showing the $^{19}$F-NMR/CDCl$_3$ spectrum of PAG25 in Synthesis Example 41.
Figure 31:
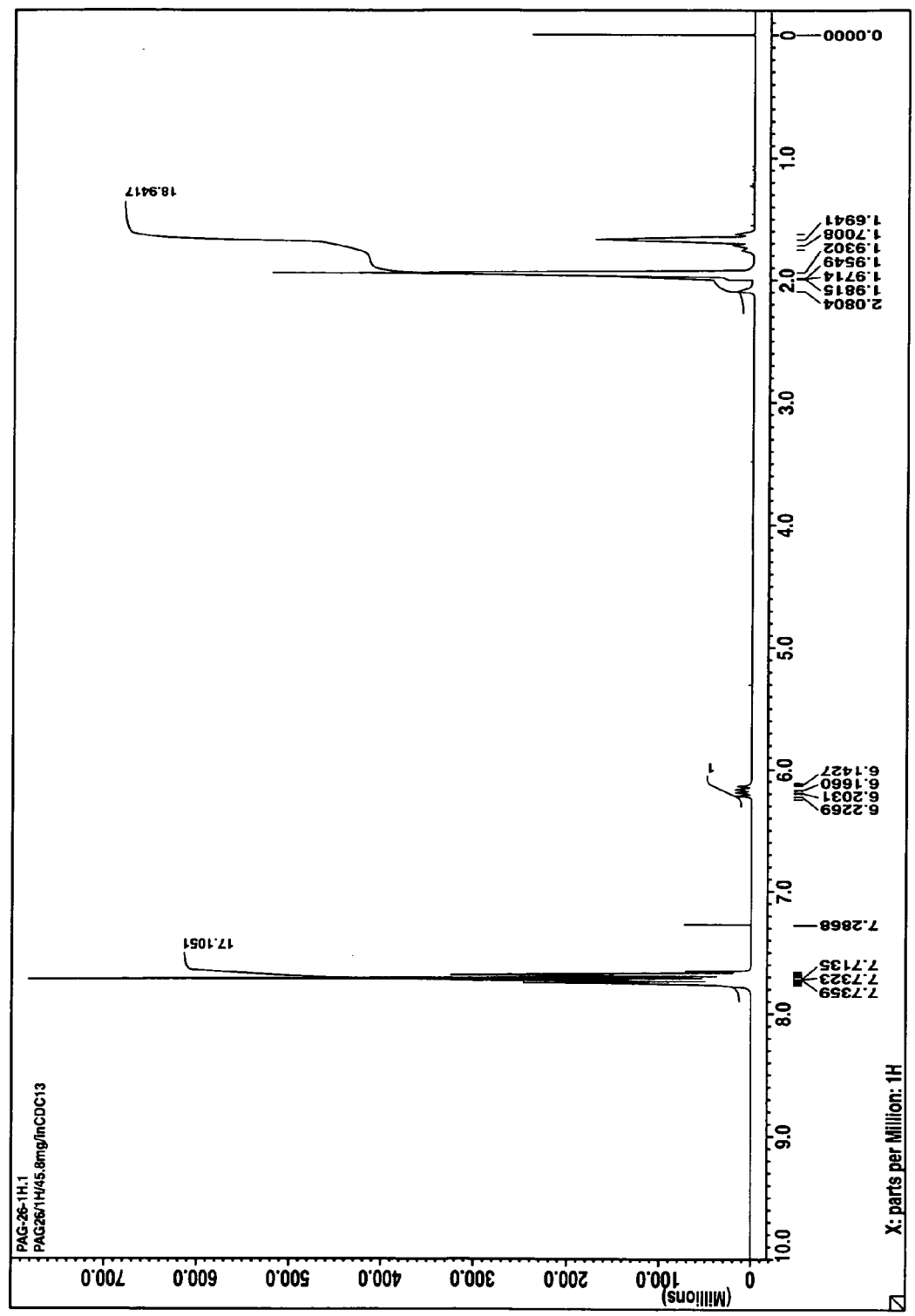
FIG. 31 is a diagram showing the $^1$H-NMR/CDCl$_3$ spectrum of PAG26 in Synthesis Example 42.
Figure 32:
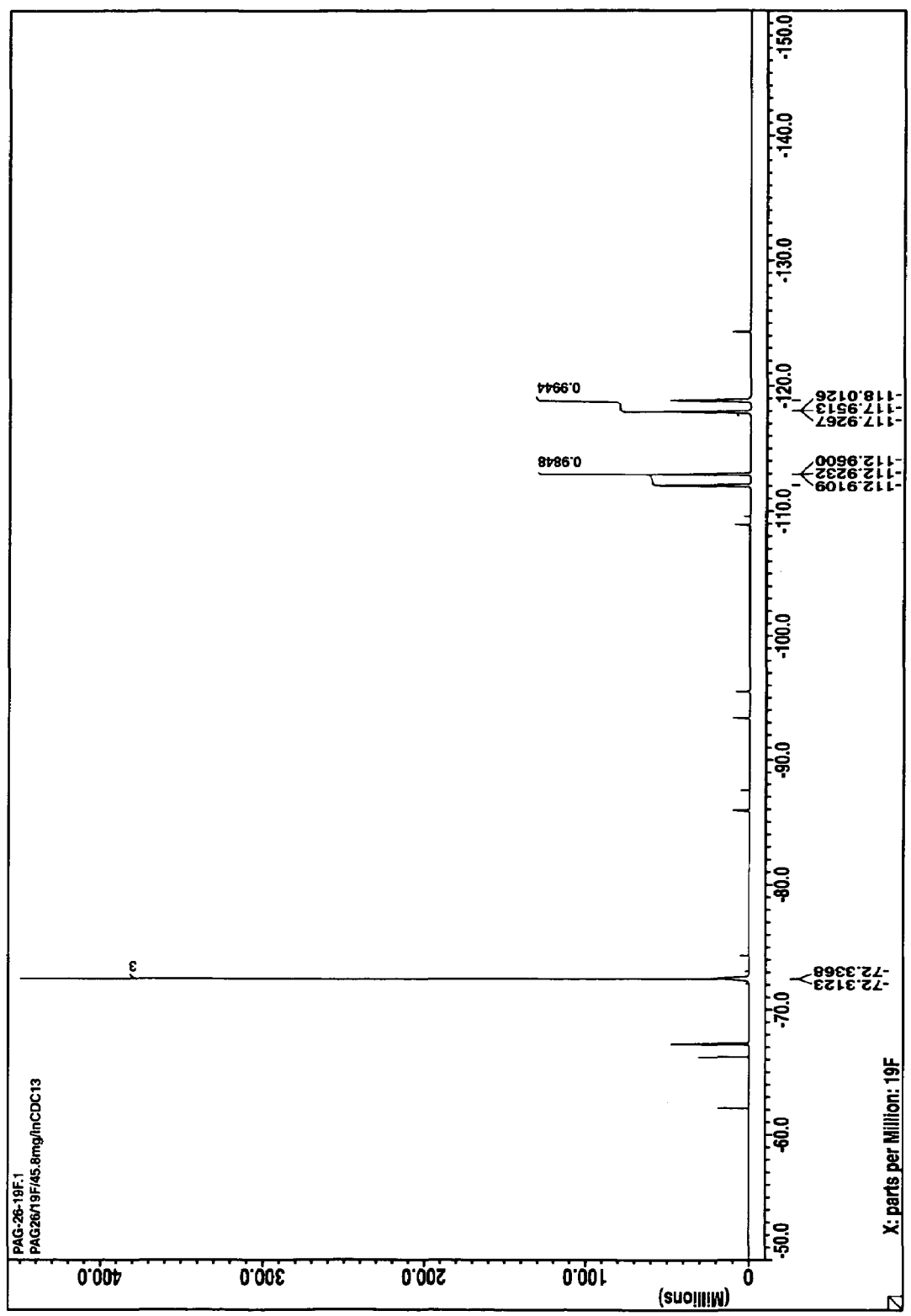
FIG. 32 is a diagram showing the $^{19}$F-NMR/CDCl$_3$ spectrum of PAG26 in Synthesis Example 42.
Figure 33:
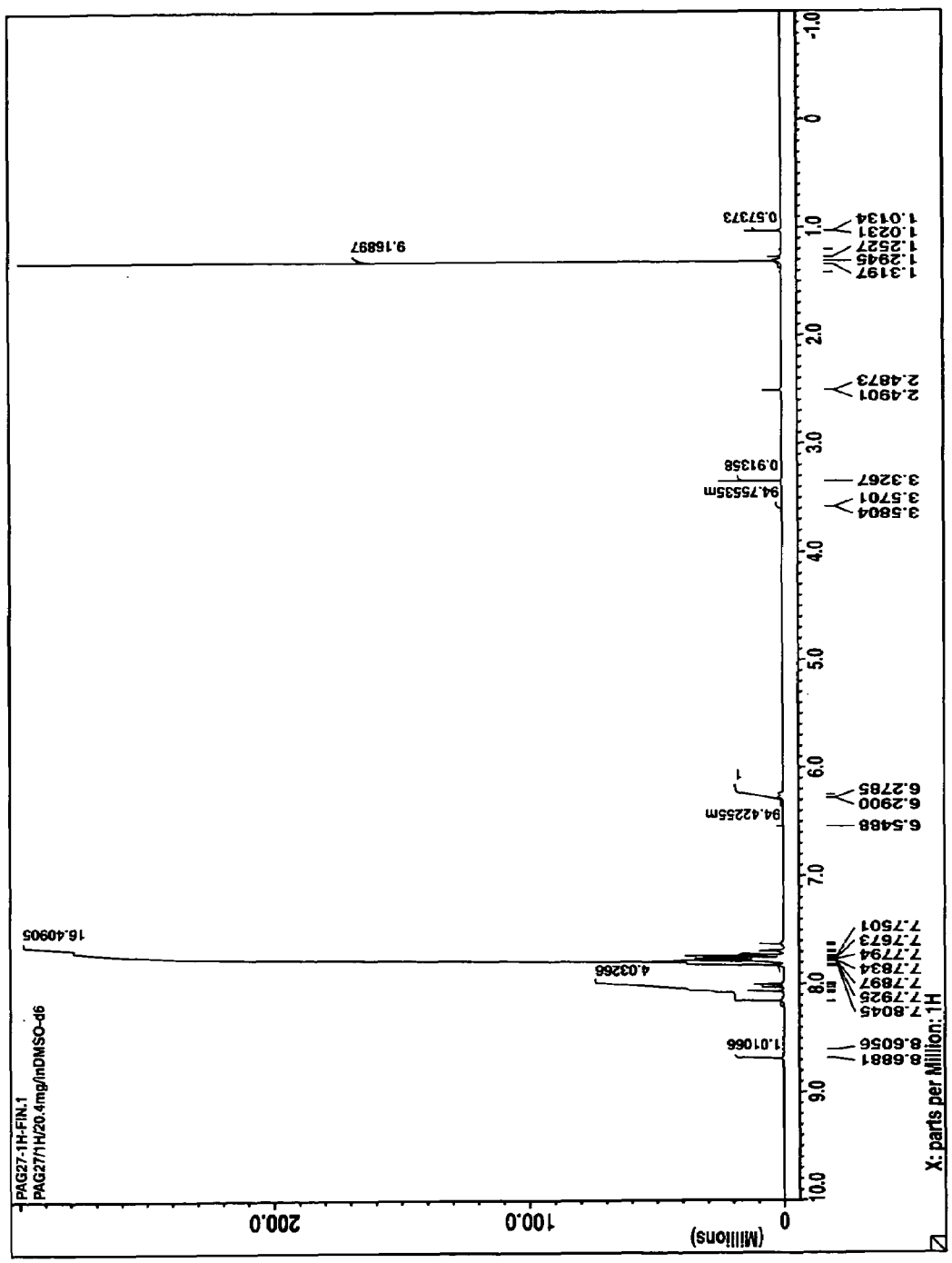
FIG. 33 is a diagram showing the $^1$H-NMR/DMSO-d$_6$ spectrum of PAG27 in Synthesis Example 43.
Figure 34:
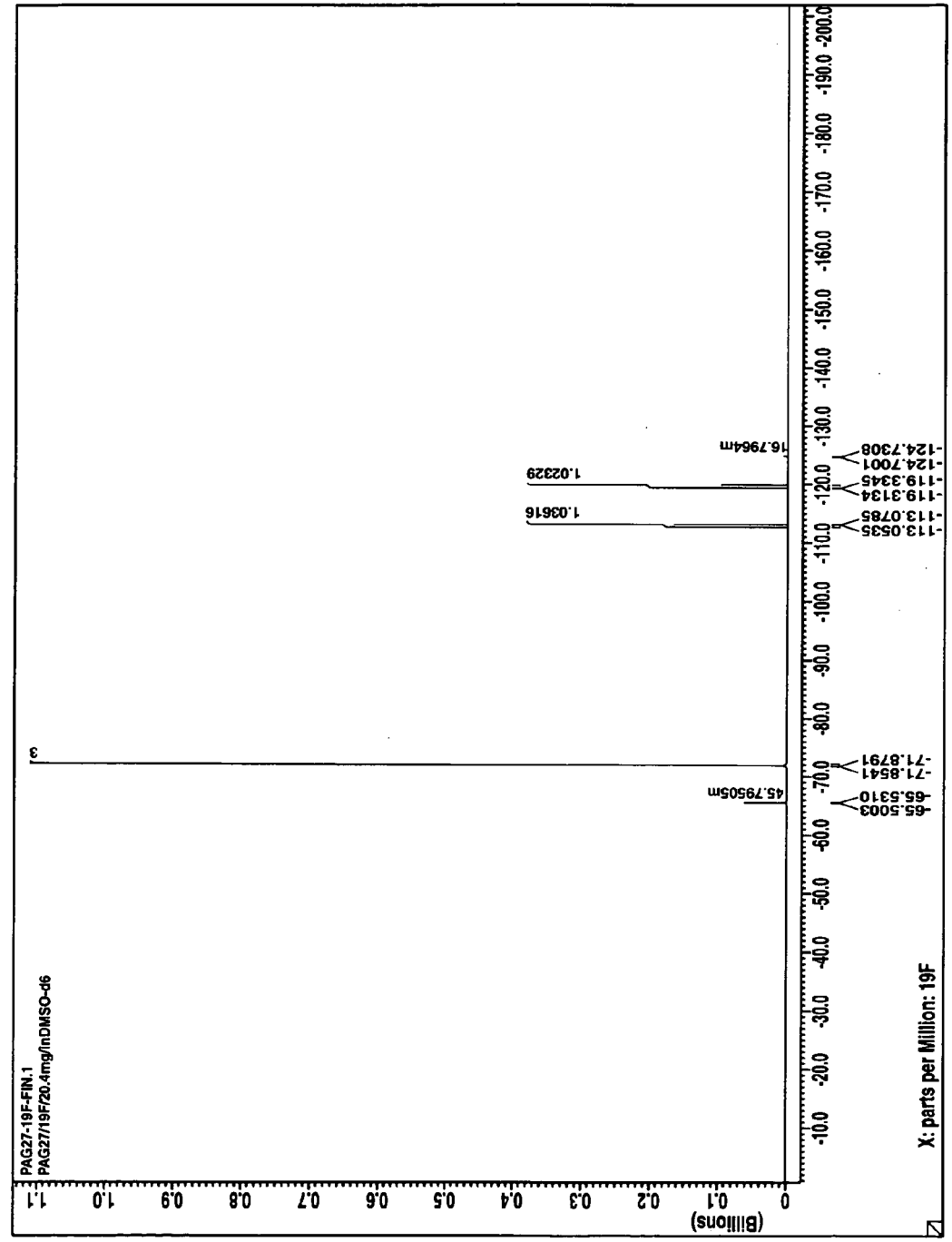
FIG. 34 is a diagram showing the $^{19}$F-NMR/DMSO-d$_6$ spectrum of PAG27 in Synthesis Example 43.

The target compound was analyzed by spectroscopy. The NMR spectra ($^1$H-NMR and $^{19}$F-NMR/D$_2$O) are shown in FIGS. 19 and 20.

Time-of-flight mass spectrometry (TOFMS; MALDI) NEGATIVE M$^-$389 (corresponding to CF$_3$CH(OCOC$_6$H$_4$C$_4$H$_9$)CF$_2$SO$_3^-$)

Synthesis Example 32

Synthesis of sodium 1,1,3,3,3-pentafluoro-2-(1-adamantane-carbonyloxy)propanesulfonate The target sodium sulfonate was obtained by following the procedure of Synthesis Example 9 aside from using 1,1,3,3,3-pentafluoropropen-2-yl-adamantane-1-carboxylate which had been synthesized by a conventional technique.

Synthesis Examples 33-43

Target compounds were synthesized as in Synthesis Example 11 except that the onium salts prepared in Synthesis Examples 1 to 8 and the sulfonate salts prepared in Synthesis Examples 27 to 32 were used. The resulting onium salts PAG17 to PAG27 are shown below.

They were analyzed by spectroscopy. The NMR spectra ($^1$H-NMR and $^{19}$F-NMR/CDCl$_3$, $^1$H-NMR and $^{19}$F-NMR/DMSO-d$_6$) of PAG17, PAG18, PAG20, PAG22, PAG25, PAG26 and PAG27 are shown in FIGS. 21 to 34.

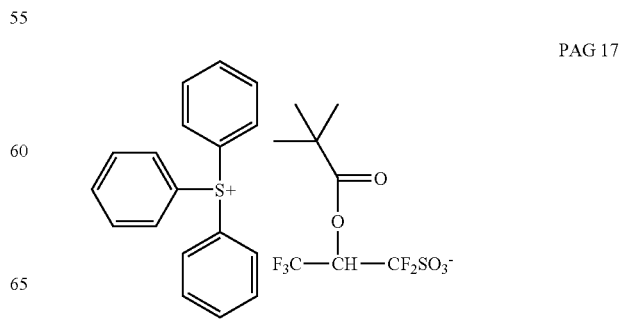

PAG 17

PAG 18
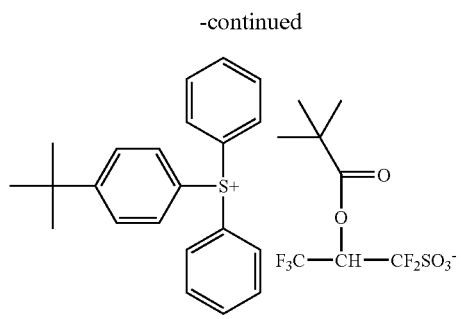
PAG 19
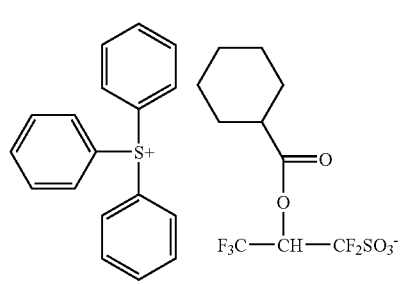
PAG 20
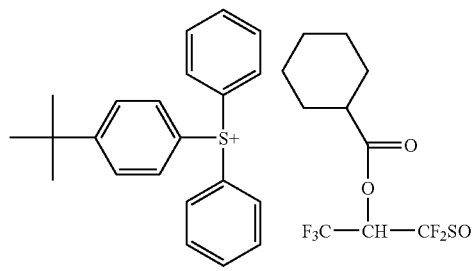
PAG 21
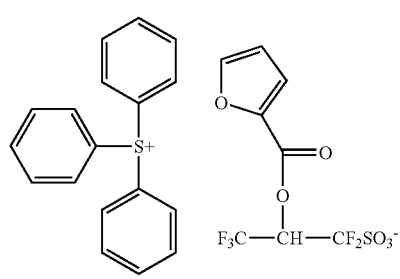
PAG 22
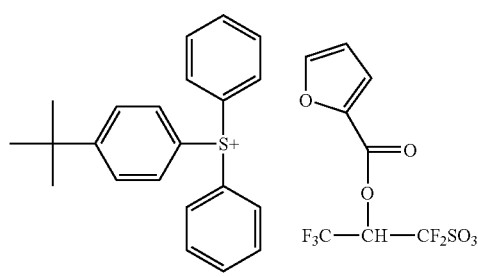
PAG 23
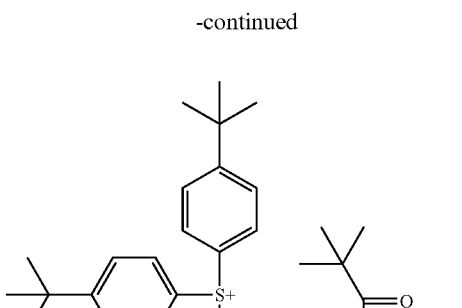
PAG 24
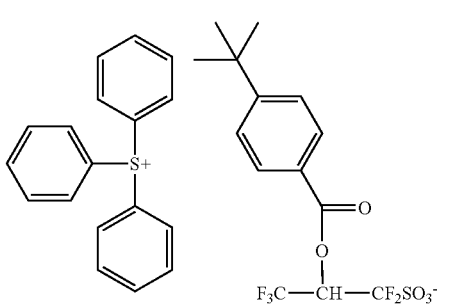
PAG 25
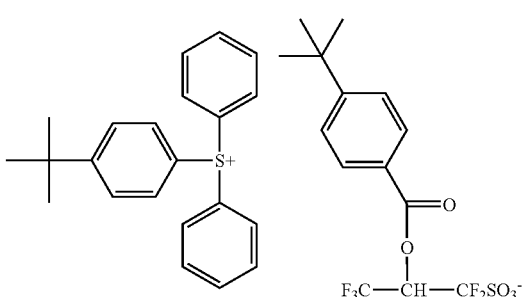
PAG 26
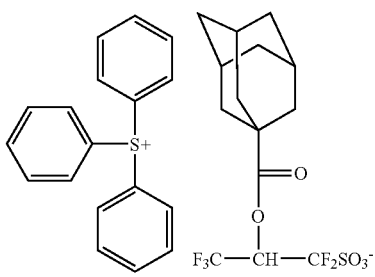

-continued

PAG 27

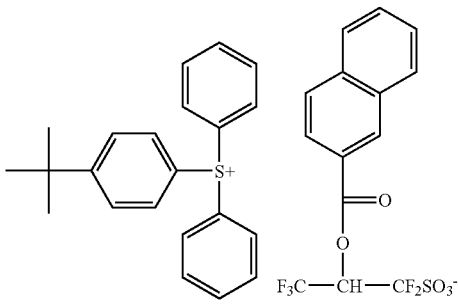

Synthesis Example 44

Synthesis of triphenylsulfonium 1,1,3,3,3-pentafluoro-2-acetyloxypropane-1-sulfonate (PAG28)

(Hydrolysis of Carboxylic Ester in Anion Followed by Re-Esterification with Carboxylic Anhydride)

In 104 g of methanol was dissolved 34.4 g of triphenylsulfonium 1,1,3,3,3-pentafluoro-2-benzoyloxypropane-1-sulfonate prepared in Synthesis Example 11. 2.5 g of sodium hydroxide in 7.5 g of water was added to the solution whereupon reaction took place for one hour under ice cooling. The reaction was monitored by thin layer chromatography (TLC), and the disappearance of the reactant spot was confirmed, after which 6.8 g of 12N hydrochloric acid was added to quench the reaction. 270 g of dichloromethane was added to the reaction solution, from which the organic layer was separated and concentrated, leaving 28 g of the concentrate. To an aliquot (3.0 g) of the concentrate were added 28 g of methylene chloride and 0.7 g of pyridine. Under ice cooling, 0.8 g of acetic anhydride was added dropwise to the solution, then 0.7 g of triethylamine and 0.04 g of 4-(N,N-dimethylamino) pyridine added. The mixture was stirred for 4 hours. The reaction was quenched with 20 g of water, after which the organic layer was separated, washed with 50 g of water three times, and concentrated. The target compound was obtained as 3 g of oil.

Figure 35:
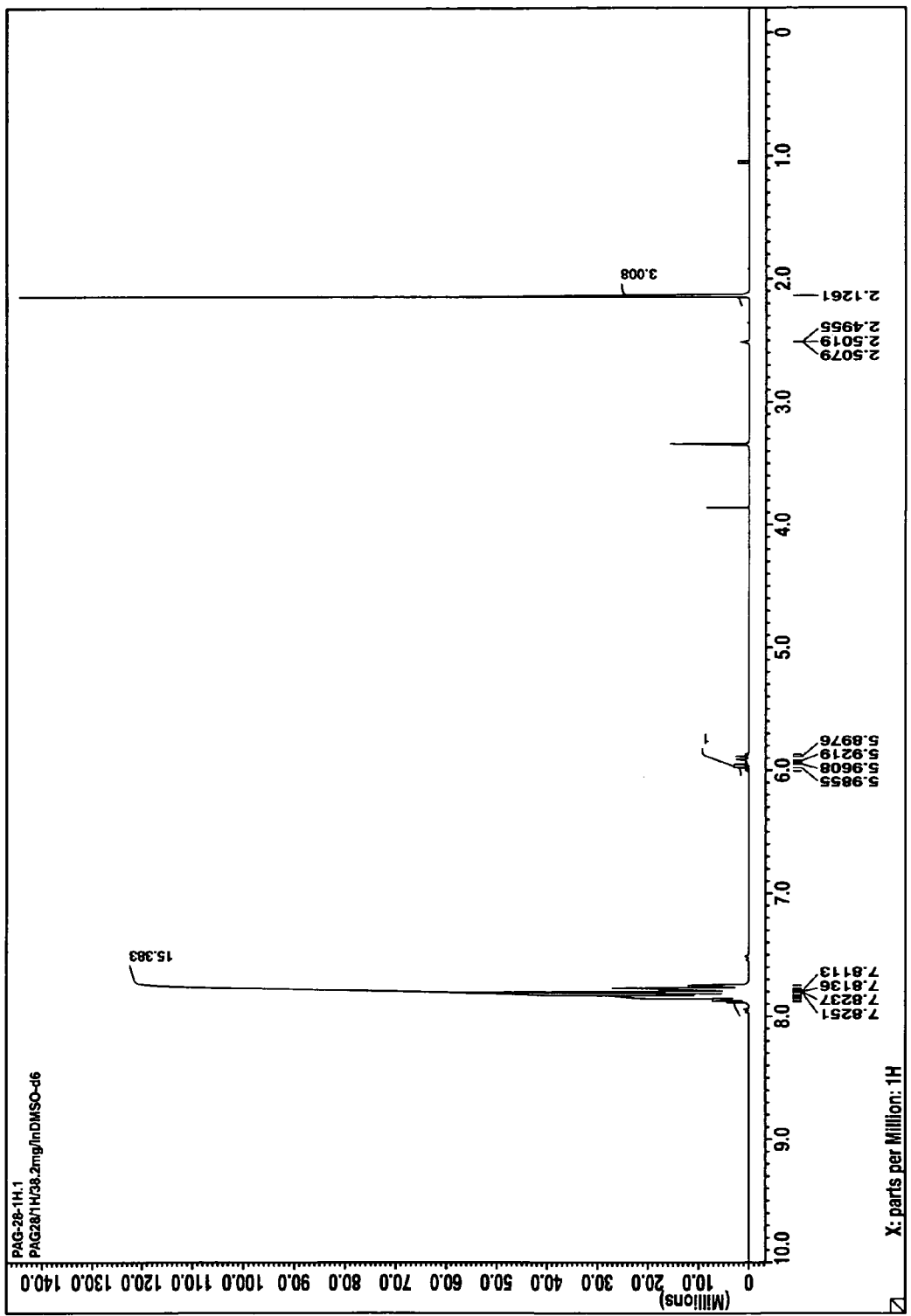
FIG. 35 is a diagram showing the $^1$H-NMR/DMSO-d$_6$ spectrum of PAG28 in Synthesis Example 44.
Figure 36:
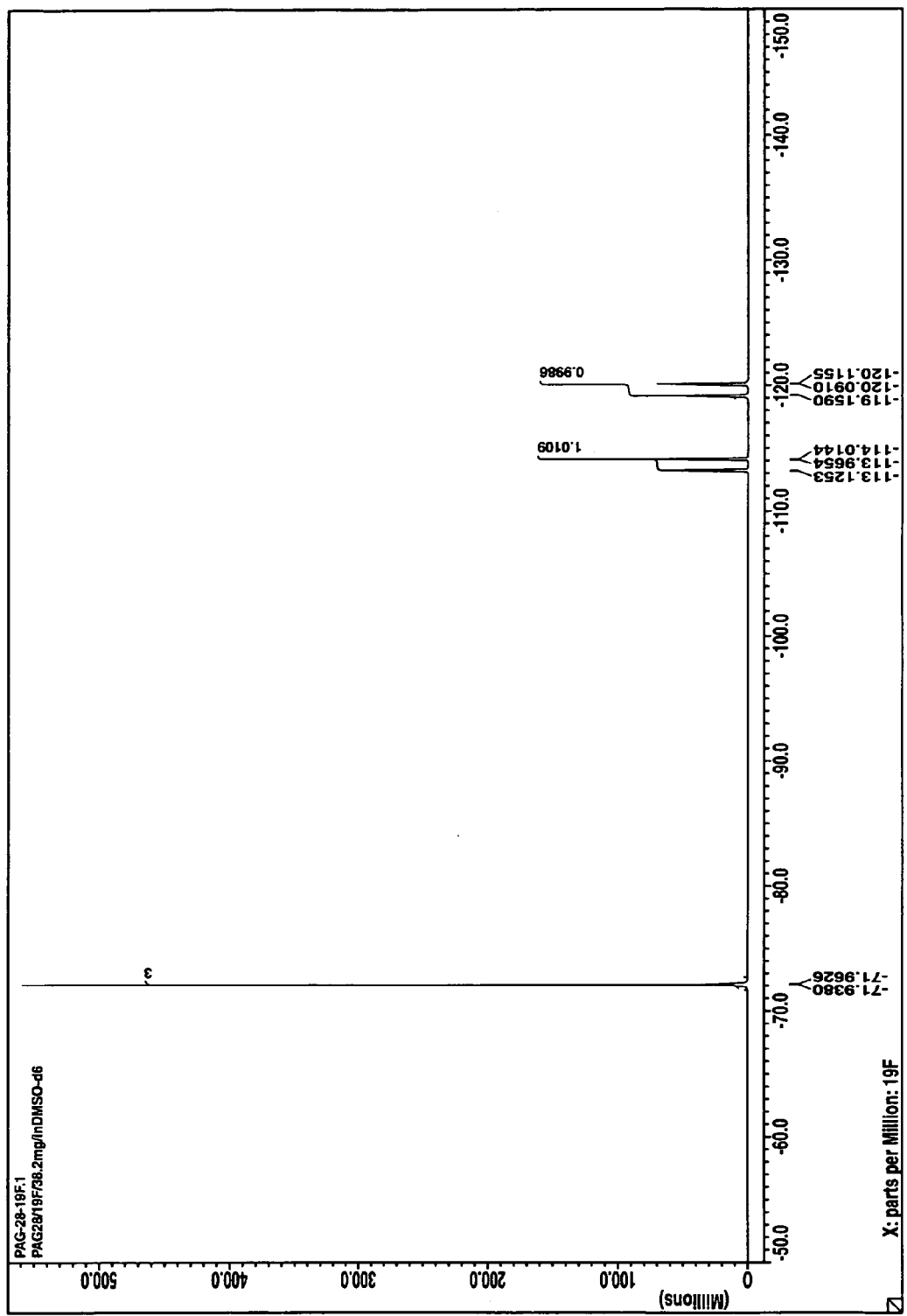
FIG. 36 is a diagram showing the $^{19}$F-NMR/DMSO-$d_6$ spectrum of PAG28 in Synthesis Example 44.

The target compound was analyzed by spectroscopy. The data of IR spectroscopy are shown below. The NMR spectra ($^1$H-NMR and $^{19}$F-NMR/DMSO-$d_6$) are shown in FIGS. 35 and 36.

Infrared absorption spectra (IR; KBr, cm$^{-1}$) 3089, 3064, 2971, 1779, 1581, 1477, 1448, 1373, 1322, 1253, 1213, 1186, 1164, 1116, 1091, 1072, 995, 919, 750, 684, 642

Time-of-flight mass spectrometry (TOFMS; MALDI) POSITIVE M$^+$263 (corresponding to $(C_6H_5)_3S+$) NEGATIVE M$^-$269 (corresponding to $CF_3CH(OCOCH_3)CF_2SO_3^-$)

Synthesis Example 45

Synthesis of (4-hydroxyphenyl)diphenylsulfonium 1,1,3,3,3-pentafluoro-2-benzoyloxypropane-1-sulfonate (PAG29)

In 60 g of dichloromethane was dissolved 6.7 g of 4-tert-butoxyphenyldiphenylsulfonium 1,1,3,3,3-pentafluoro-2-benzoyloxypropane-1-sulfonate (PAG4) prepared in Synthesis Example 14. Methanesulfonic acid, 0.1 g, was added to the solution, which was heated and stirred at 40° C. for 3 hours. The organic layer was washed with 30 g of water three times, and concentrated. Diethyl ether was added to the concentrate for crystallization. The crystals were filtered and dried, obtaining the target compound in an amount of 4.9 g.

Analysis of the target compound by NMR spectroscopy ($^1$H-NMR/CDCl$_3$) confirmed the disappearance of the peak corresponding to tert-butoxy (C$\underline{H}_3$)C— in the reactant, with the target compound being identified. It was also analyzed by time-of-flight mass spectrometry.

Time-of-flight mass spectrometry (TOFMS; MALDI) POSITIVE M$^+$279 (corresponding to $(C_6H_5)_2(C_6H_5O)S^+$) NEGATIVE M$^-$333 (corresponding to $CF_3CH(OCOC_6H_5)CF_2SO_3^-$)

Synthesis Example 46

Synthesis of (4-methacryloyloxyphenyl)diphenylsulfonium 1,1,3,3,3-pentafluoro-2-benzoyloxypropane-1-sulfonate (PAG30)

In 15 g of dichloromethane was dissolved 3 g of (4-hydroxyphenyl)diphenylsulfonium 1,1,3,3,3-pentafluoro-2-benzoyloxypropane-1-sulfonate (PAG29) prepared in Synthesis Example 45. Methacryloyl chloride, 1 g, was added to the solution, which was cooled in an ice bath, and 0.9 ml of triethylamine was added dropwise. 30 g of 3N dilute hydrochloric acid was added, after which the organic layer was separated, washed with 30 g of water three times, and concentrated. The concentrate was purified by silica gel column chromatography (elute: dichloromethane/methanol 20/1 in weight ratio), after which diethyl ether was added to the concentrate for crystallization. The crystals were filtered and dried, obtaining the target compound in an amount of 3.5 g.

On analysis of the target compound by NMR spectroscopy ($^1$H-NMR/DMSO-$d_6$), spectral peaks were observed near 6.33 ppm, 5.97 ppm and 2.00 ppm, confirming the substitution of methacryloyl group. It was also analyzed by time-of-flight mass spectrometry.

Time-of-flight mass spectrometry (TOFMS; MALDI) POSITIVE M$^+$279 (corresponding to $(C_6H_5)_2(C_{10}H_9O_2)S^+$) NEGATIVE M$^-$333 (corresponding to $CF_3CH(OCOC_6H_5)CF_2SO_3^-$)

Examples 1-16 & Comparative Examples 1-3

Evaluation of Resist Resolution

Resist Compositions were prepared by dissolving the photoacid generators of Synthesis Examples, Polymers 1 to 8 as the base resin, dissolution accelerator DRR1, dissolution inhibitor DRI1, and basic compound in a solvent containing 0.01 wt % of surfactant FC-430 (Sumitomo 3M Co., Ltd.) according to the formulation shown in Tables 1 and 2. Note that Polymers 1 to 8, DRR1 and DRI1 are shown below. They were filtered through a Teflon® filter having a pore size of 0.2 µm, giving resist solutions.

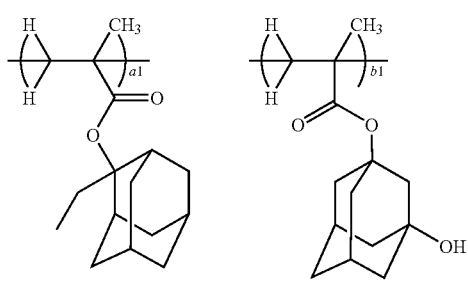
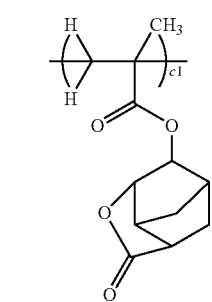
(Polymer 1)
($a1 = 0.35$, $b1 = 0.20$, $d1 = 0.45$, Mw = 9,200)
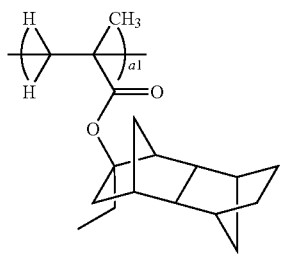 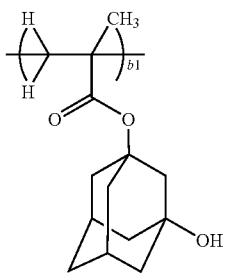
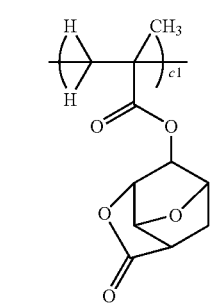
(Polymer 2)
($a1 = 0.30$, $b1 = 0.25$, $c1 = 0.45$, Mw = 8,300)
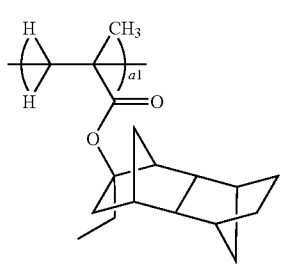 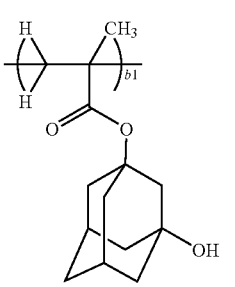
-continued
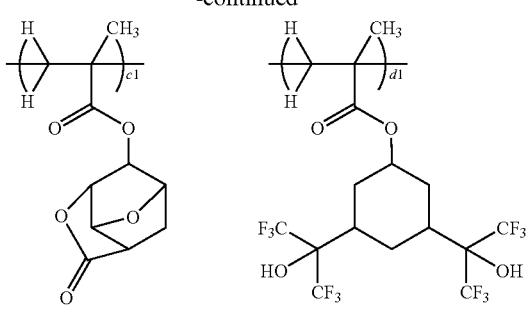
(Polymer 4)
($a1 = 0.25$, $b1 = 0.25$, $c1 = 0.35$, $d1 = 0.10$, Mw = 7,600)
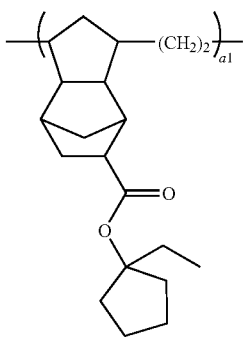 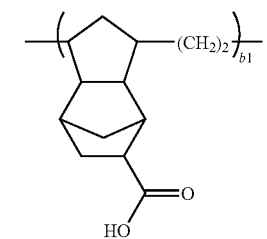
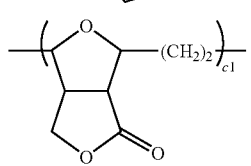
(Polymer 5)
($a1 = 0.35$, $b1 = 0.15$, $c1 = 0.50$, Mw = 8,100)
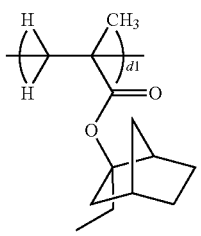 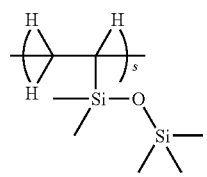
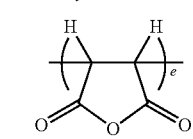
(Polymer 6)
($d1 = 0.40$, $s = 0.20$, $e = 0.40$, Mw = 10,200)
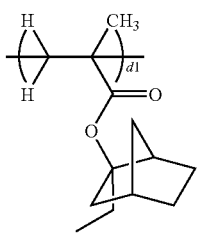 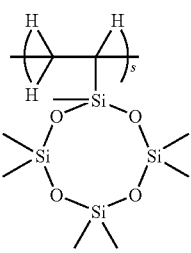

-continued

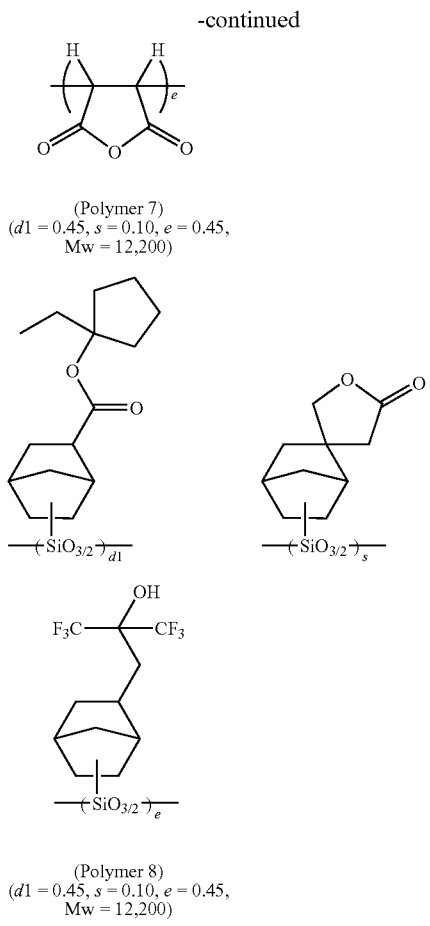

(Polymer 7)
($d1 = 0.45$, $s = 0.10$, $e = 0.45$,
Mw = 12,200)

(Polymer 8)
($d1 = 0.45$, $s = 0.10$, $e = 0.45$,
Mw = 12,200)

(DRR 1)

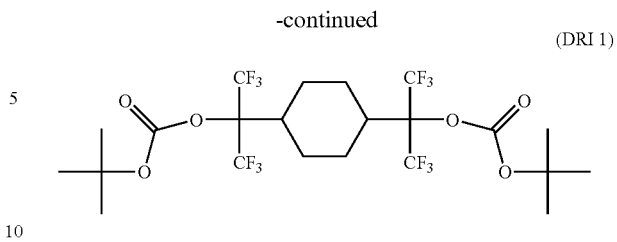

(DRI 1)

An antireflective coating liquid ARC-29A (Nissan Chemical Co., Ltd.) was coated onto a silicon substrate and baked at 200° C. for 60 seconds to form an antireflective coating of 78 nm thick. The resist solution was spin coated onto the antireflective coating and baked on a hot plate at 120° C. for 60 seconds, forming a resist film of 200 nm thick. The resist film was exposed by means of an ArF excimer laser microstepper model S305B (Nikon Corp., NA 0.68, σ 0.85, ⅔ annular illumination, Cr mask), post-exposure baked (PEB) at 110° C. for 90 seconds, and developed with a 2.38 wt % aqueous solution of tetramethylammonium hydroxide (TMAH) for 60 seconds.

An optimal exposure dose (sensitivity Eop, mJ/cm$^2$) was the exposure which provided a 1:1 resolution at the top and bottom of a 0.12-μm group line-and-space pattern. The minimum line width (μm) of a line-and-space pattern which was ascertained separate at this dose was the resolution of a test resist. The formulation and test results of the resist compositions are shown in Tables 1 and 2.

The solvents and basic compounds in Tables 1 and 2 are shown below as well as the photoacid generators in Comparative Examples.

Solvent A: propylene glycol methyl ether acetate
Solvent B: cyclohexanone
Basic Compound A: tri-n-octylamine
Basic Compound B: triethanolamine
Basic Compound C: trismethoxymethoxyethylamine
Basic Compound D: tris(2-acetoxyethyl)amine
TPS-NfO: triphenylsulfonium perfluoro-1-butanesulfonate
TPS—PFOS: triphenylsulfonium perfluoro-1-octanesulfonate

TABLE 1

| Formulation (pbw) | Example | | | | | | | | | |
|---|---|---|---|---|---|---|---|---|---|---|
| | 1 | 2 | 3 | 4 | 5 | 6 | 7 | 8 | 9 | 10 |
| Polymer 1 | 80 | | | | | | | | 80 | |
| Polymer 2 | | 80 | | | | | | | | 80 |
| Polymer 3 | | | 80 | | | | | | | |
| Polymer 4 | | | | 80 | | | | | | |
| Polymer 5 | | | | | 80 | | | | | |
| Polymer 6 | | | | | | 80 | | | | |
| Polymer 7 | | | | | | | 80 | | | |
| Polymer 8 | | | | | | | | 80 | | |
| PAG1 | 4 | 4 | 4 | 4 | 4 | 4 | 4 | 4 | | |
| PAG2 | | | | | | | | | 5 | |
| PAG3 | | | | | | | | | | 5 |
| PAG4 | | | | | | | | | | |
| PAG7 | | | | | | | | | | |
| PAG10 | | | | | | | | | | |
| PAG13 | | | | | | | | | | |
| TPS-NfO | | | | | | | | | | |
| TPS-PFOS | | | | | | | | | | |
| Basic Compound A | 0.5 | 0.5 | 0.5 | 0.5 | | | | | | |
| Basic Compound B | | | | | 0.5 | 0.5 | 0.5 | | | |
| Basic Compound C | | | | | | | | 0.5 | 0.5 | 0.5 |
| Basic Compound D | | | | | | | | | | |

TABLE 1-continued

| Formulation (pbw) | Example | | | | | | | | | |
|---|---|---|---|---|---|---|---|---|---|---|
| | 1 | 2 | 3 | 4 | 5 | 6 | 7 | 8 | 9 | 10 |
| DRR1 | | | | | | | | | | |
| DRI1 | | | | | | | | | | |
| Solvent A | 800 | 800 | 800 | 800 | | 800 | 800 | 800 | 800 | 800 |
| Solvent B | | | | | 800 | | | | | |
| Tests | | | | | | | | | | |
| Sensitivity (mJ/cm$^2$) | 25 | 23 | 21 | 23 | 20 | 21 | 21 | 20 | 30 | 35 |
| Resolution (μm) | 0.11 | 0.11 | 0.11 | 0.11 | 0.12 | 0.11 | 0.11 | 0.12 | 0.11 | 0.11 |

TABLE 2

| Formulation (pbw) | Example | | | | | | Comparative Example | | |
|---|---|---|---|---|---|---|---|---|---|
| | 11 | 12 | 13 | 14 | 15 | 16 | 1 | 2 | 3 |
| Polymer 1 | 40 | | | | | | 80 | | |
| Polymer 2 | | 40 | 40 | 60 | | 80 | | 80 | 40 |
| Polymer 3 | | 40 | | | | | | | 40 |
| Polymer 4 | | | 40 | | 80 | | | | |
| Polymer 5 | 40 | | | 20 | | | | | |
| Polymer 6 | | | | | | | | | |
| Polymer 7 | | | | | | | | | |
| Polymer 8 | | | | | | | | | |
| PAG1 | | | | | 4 | | | | |
| PAG2 | | | | | | | | | |
| PAG3 | | | | | | 4 | | | |
| PAG4 | 5 | | | | | | | | |
| PAG7 | | 6 | | | | | | | |
| PAG10 | | | 6 | | | | | | |
| PAG13 | | | | 6 | | | | | |
| TPS-NfO | | | | | 1 | | 4 | | 2 |
| TPS-PFOS | | | | | | 1 | | 4 | 3 |
| Basic Compound A | | | | | | | 0.5 | 0.5 | 0.5 |
| Basic Compound B | | | | | | | | | |
| Basic Compound C | | | | 0.5 | 0.5 | 0.5 | | | |
| Basic Compound D | 0.5 | 0.5 | 0.5 | | | | | | |
| DRR1 | | | | | 10 | | | | |
| DRI1 | | | | | | 10 | | | |
| Solvent A | 600 | 800 | 800 | 800 | 800 | 800 | 800 | 800 | 800 |
| Solvent B | 200 | | | | | | | | |
| Tests | | | | | | | | | |
| Sensitivity (mJ/cm$^2$) | 38 | 36 | 35 | 40 | 25 | 35 | 26 | 30 | 28 |
| Resolution (μm) | 0.11 | 0.11 | 0.1 | 0.11 | 0.11 | 0.11 | 0.11 | 0.11 | 0.11 |

Examples 17-27

Evaluation of Resist Resolution

Using the photoacid generators in Synthesis Examples, resist compositions having the formulation shown in Table 3 were prepared as in Examples 1-16. They were similarly evaluated for resolution. The formulation and test results of the resist compositions are shown in Table 3.

TABLE 3

| Formulation (pbw) | Example | | | | | | | | | | |
|---|---|---|---|---|---|---|---|---|---|---|---|
| | 17 | 18 | 19 | 20 | 21 | 22 | 23 | 24 | 25 | 26 | 27 |
| Polymer 1 | 80 | 80 | | | | | | | | 40 | |
| Polymer 2 | | | 80 | 80 | | | | | 40 | | |
| Polymer 3 | | | | | 80 | 80 | | | | | |
| Polymer 4 | | | | | | | 80 | 80 | | | |
| Polymer 5 | | | | | | | | | 40 | 40 | |
| Polymer 8 | | | | | | | | | | | 80 |
| PAG1 | | | | | | 2 | | | | | |
| PAG17 | 6 | | | | 5 | 4 | | | | | |

TABLE 3-continued

| Formulation (pbw) | Example | | | | | | | | | | |
|---|---|---|---|---|---|---|---|---|---|---|---|
| | 17 | 18 | 19 | 20 | 21 | 22 | 23 | 24 | 25 | 26 | 27 |
| PAG18 | | 6 | | | | | | | | | |
| PAG20 | | | 6 | | | | 6 | 6 | | | 6 |
| PAG22 | | | | 5 | | | | | | | |
| PAG25 | | | | | | | | | 5 | | |
| PAG26 | | | | | | | | | | 6 | |
| TPS-NfO | | | | | | | | | | | |
| TPS-PFOS | | | | | | | | | | | |
| Basic Compound A | 0.5 | 0.5 | 0.5 | 0.5 | | | | | | | |
| Basic Compound B | | | | | 0.5 | 0.5 | 0.5 | | | | |
| Basic Compound C | | | | | | | | 0.5 | 0.5 | 0.5 | 0.5 |
| Basic Compound D | | | | | | | | | | | |
| Solvent A | 800 | 720 | 800 | 800 | 560 | 800 | 800 | 800 | 720 | 800 | 560 |
| Solvent B | | 80 | | | 240 | | | | 80 | | 240 |
| Tests | | | | | | | | | | | |
| Sensitivity (mJ/cm²) | 24 | 27 | 23 | 21 | 21 | 20 | 22 | 24 | 26 | 28 | 35 |
| Resolution (μm) | 0.11 | 0.11 | 0.11 | 0.11 | 0.12 | 0.11 | 0.11 | 0.12 | 0.11 | 0.11 | 0.12 |

Next, simulative immersion photolithography was carried out using the resist compositions of Examples 1, 4, 17, 19 and Comparative Example 1. Specifically, a resist film of 1250 nm thick was formed on a wafer by a procedure as described above and exposed by means of an ArF excimer laser microstepper model S307E (Nikon Corp., NA 0.85, dipole, 6% HTPSM). Immediately after the exposure, deionized water was fed over the entire surface of the wafer, whereby the exposed surface of resist was immersed in deionized water for 60 seconds (puddle). The wafer was rotated to spin off the water, followed by ordinary PEB and development. The number of defects in the pattern formed after development was counted by a wafer inspection system WINWIN 50-1200L (Tokyo Seimitsu Co., Ltd.). A defect density was computed therefrom.

Defect density(/cm²)=
(total number of detected defects)/(test area).
Pattern formed: repetitive pattern of 80 nm/pitch 160 nm line-and-space
Defect detection: light source UV, detection pixel size 0.125 μm, cell-to-cell mode Additionally, the pattern profile in resist cross-section was observed under a scanning electron microscope. The results are shown in Table 4.

TABLE 4

| | Pattern profile | Defect density (/cm²) |
|---|---|---|
| Example 1 | rectangular | <0.05 |
| Example 4 | rectangular | <0.05 |
| Example 17 | rectangular | 0.35 |
| Example 19 | rectangular | <0.05 |
| Comparative Example 1 | extreme T-top | 10 |

As is evident from Tables 1 to 4, the resist compositions of the invention have a high sensitivity and high resolution and invite neither profile changes nor defects during a long term of water rinsing as compared with the prior art composition, suggesting an ability to comply with the immersion photolithography. As demonstrated in Synthesis Example 42, the photoacid generator capable of generating a sulfonic acid having formula (1a) can be converted into lower molecular weight compounds as a result of its ester moiety being decomposed by hydrolysis, especially alkaline hydrolysis. The load to the environment is thus reduced as compared with prior art photoacid generators capable of generating perfluoroalkylsulfonic acids or partially fluorinated alkylsulfonic acids.

Japanese Patent Application Nos. 2005-109903 and 2005-316096 are incorporated herein by reference.

Although some preferred embodiments have been described, many modifications and variations may be made thereto in light of the above teachings. It is therefore to be understood that the invention may be practiced otherwise than as specifically described without departing from the scope of the appended claims.

The invention claimed is:

1. A sulfonate salt having the general formula (1):

$$CF_3—CH(OCOR)—CF_2SO_3^-M^+ \qquad (1)$$

wherein R is a substituted or unsubstituted, straight, branched or cyclic $C_1$-$C_{20}$ alkyl group or a substituted or unsubstituted $C_6$-$C_{14}$ aryl group, and M⁺ is a lithium, sodium, potassium, ammonium or tetramethylammonium ion.

2. A sulfonium salt having the general formula (2):

$$R^1R^2R^3S^+CF_3—CH(OCOR)—CF_2SO_3^- \qquad (2)$$

wherein R is a substituted or unsubstituted, straight, branched or cyclic $C_1$-$C_{20}$ alkyl group or a substituted or unsubstituted $C_6$-$C_{14}$ aryl group, $R^1$, $R^2$ and $R^3$ are each independently selected from the class consisting of substituted or unsubstituted, straight or branched $C_1$-$C_{10}$ alkyl, alkenyl and oxoalkyl groups, and substituted or unsubstituted $C_6$-$C_{18}$ aryl, aralkyl and aryloxoalkyl groups, or any two or more of $R^1$, $R^2$ and $R^3$ may bond together to form a ring with the sulfur atom.

3. A sulfonium salt having the general formula (2a):

$$R'—(O)_n-PhS^+Ph_2CF_3—CH(OCOR)—CF_2SO_3^- \qquad (2a)$$

wherein R is a substituted or unsubstituted, straight, branched or cyclic $C_1$-$C_{20}$ alkyl group or a substituted or unsubstituted $C_6$-$C_{14}$ aryl group, R' is a substituted or unsubstituted, straight, branched or cyclic $C_1$-$C_{20}$ alkyl or alkenyl group or a substituted or unsubstituted $C_6$-$C_{14}$ aryl group, Ph is phenyl, and n is 0 or 1.

4. A iodonium salt having the general formula (2b):

$$R'(O)_n\text{-PhI}^+\text{Ph}(O)_n\text{-R'CF}_3\text{---CH(OCOR)---CF}_2\text{SO}_3^- \quad (2b)$$

wherein R is a substituted or unsubstituted, straight, branched or cyclic $C_1$-$C_{20}$ alkyl group or a substituted or unsubstituted $C_6$-$C_{14}$ aryl group, R' is a substituted or unsubstituted, straight, branched or cyclic $C_1$-$C_{20}$ alkyl or alkenyl group or a substituted or unsubstituted $C_6$-$C_{14}$ aryl group, Ph is phenyl, and n is 0 or 1.

* * * * *